(12) United States Patent
De Graff et al.

(10) Patent No.: US 9,186,060 B2
(45) Date of Patent: Nov. 17, 2015

(54) SYSTEMS, METHODS AND DEVICES HAVING STRETCHABLE INTEGRATED CIRCUITRY FOR SENSING AND DELIVERING THERAPY

(71) Applicant: MC10, Inc., Cambridge, MA (US)

(72) Inventors: Bassel De Graff, San Juan (TT); Roozbeh Ghaffari, Cambridge, MA (US); William J. Arora, Bellevue, WA (US)

(73) Assignee: MC10, Inc., Lexington, MA (US)

( * ) Notice: Subject to any disclaimer, the term of this patent is extended or adjusted under 35 U.S.C. 154(b) by 0 days.

(21) Appl. No.: 13/963,778

(22) Filed: Aug. 9, 2013

(65) Prior Publication Data

US 2014/0039290 A1    Feb. 6, 2014

Related U.S. Application Data

(60) Division of application No. 13/336,518, filed on Dec. 23, 2011, now Pat. No. 8,536,667, which is a continuation of application No. 12/723,475, filed on Mar. 12, 2010, now Pat. No. 8,097,926, which is a (Continued)

(51) Int. Cl.
*H01L 21/46*     (2006.01)
*H01L 29/40*     (2006.01)

(Continued)

(52) U.S. Cl.
CPC .............. *A61B 5/0031* (2013.01); *A61B 5/01* (2013.01); *A61B 5/03* (2013.01); *A61B 5/053* (2013.01);

(Continued)

(58) Field of Classification Search
CPC ................................ H01L 27/14618
USPC .................. 257/291, 773–786; 438/455–457; 607/118, 122
See application file for complete search history.

(56) References Cited

U.S. PATENT DOCUMENTS 3,716,861 A    2/1973   Root
3,805,427 A    4/1974   Epstein (Continued)

FOREIGN PATENT DOCUMENTS

WO    WO 2005/122285 A2    12/2005
WO    WO 2008/030960 A2     3/2008

(Continued)

OTHER PUBLICATIONS

Demura et al., "Immobilization of Glucose Oxidase with Bombyx Mori Silk Fibroin by Only Stretching Treatment and its Application to Glucose Sensor," Biotechnology and Bioengineering, vol. 33, 598-603 (6 pages) (1989).

(Continued)

*Primary Examiner* — Calvin Lee
(74) *Attorney, Agent, or Firm* — Nixon Peabody LLP

(57) ABSTRACT

System, devices and methods are presented that integrate stretchable or flexible circuitry, including arrays of active devices for enhanced sensing, diagnostic, and therapeutic capabilities. The invention enables conformal sensing contact with tissues of interest, such as the inner wall of a lumen, a the brain, or the surface of the heart. Such direct, conformal contact increases accuracy of measurement and delivery of therapy. Further, the invention enables the incorporation of both sensing and therapeutic devices on the same substrate allowing for faster treatment of diseased tissue and fewer devices to perform the same procedure.

20 Claims, 81 Drawing Sheets

Related U.S. Application Data continuation-in-part of application No. 12/686,076, filed on Jan. 12, 2010, now Pat. No. 8,372,726, which is a continuation-in-part of application No. 12/636,071, filed on Dec. 11, 2009, now Pat. No. 8,886,334, which is a continuation-in-part of application No. 12/616,922, filed on Nov. 12, 2009, now Pat. No. 8,389,862, which is a continuation-in-part of application No. 12/575,008, filed on Oct. 7, 2009.

(60) Provisional application No. 61/164,920, filed on Mar. 31, 2009, provisional application No. 61/160,185, filed on Mar. 13, 2009, provisional application No. 61/144,149, filed on Jan. 12, 2009, provisional application No. 61/156,906, filed on Mar. 3, 2009, provisional application No. 61/121,541, filed on Dec. 11, 2008, provisional application No. 61/121,568, filed on Dec. 11, 2008, provisional application No. 61/140,169, filed on Dec. 23, 2008, provisional application No. 61/113,622, filed on Nov. 12, 2008, provisional application No. 61/103,361, filed on Oct. 7, 2008, provisional application No. 61/113,007, filed on Nov. 10, 2008.

(51) Int. Cl.
| | |
|---|---|
| *A61B 5/00* | (2006.01) |
| *H01L 27/146* | (2006.01) |
| *A61B 5/01* | (2006.01) |
| *A61B 5/03* | (2006.01) |
| *A61B 5/053* | (2006.01) |
| *A61B 18/02* | (2006.01) |
| *A61B 18/14* | (2006.01) |
| *A61B 18/18* | (2006.01) |
| *A61B 18/20* | (2006.01) |
| *A61N 7/02* | (2006.01) |

(52) U.S. Cl.
CPC .............. *A61B 5/683* (2013.01); *A61B 5/6847* (2013.01); *A61B 18/02* (2013.01); *A61B 18/14* (2013.01); *A61B 18/1815* (2013.01); *A61B 18/20* (2013.01); *A61N 7/022* (2013.01); *H01L 27/14618* (2013.01); *H01L 27/14632* (2013.01); *H01L 27/14645* (2013.01); *H01L 27/14687* (2013.01); *H01L 27/14692* (2013.01); *H01L 2924/1433* (2013.01); *H01L 2924/19041* (2013.01); *H01L 2924/19042* (2013.01); *H01L 2924/19043* (2013.01); *H01L 2924/30105* (2013.01)

(56) References Cited

U.S. PATENT DOCUMENTS

| | | | | |
|---|---|---|---|---|
| 5,907,477 | A | 5/1999 | Tuttle et al. | |
| 6,063,046 | A | 5/2000 | Allum | |
| 6,360,128 | B2 * | 3/2002 | Kordis et al. | 607/122 |
| 6,784,844 | B1 | 8/2004 | Boakes et al. | |
| 7,265,298 | B2 | 9/2007 | Maghribi | |
| 7,302,751 | B2 | 12/2007 | Hamburgen | |
| 7,337,012 | B2 | 2/2008 | Maghribi | |
| 7,487,587 | B2 | 2/2009 | Vanfleteren | |
| 7,491,892 | B2 | 2/2009 | Wagner | |
| 7,521,292 | B2 | 4/2009 | Rogers | |
| 7,557,367 | B2 | 7/2009 | Rodgers | |
| 7,618,260 | B2 | 11/2009 | Daniel et al. | |
| 7,622,367 | B1 | 11/2009 | Nuzzo | |
| 7,759,167 | B2 | 7/2010 | Vanfleteren | |
| 7,769,472 | B2 * | 8/2010 | Gerber | 607/118 |
| 7,960,246 | B2 | 6/2011 | Flamand | |
| 7,982,296 | B2 | 7/2011 | Nuzzo | |
| 8,097,926 | B2 | 1/2012 | De Graff et al. | |
| 8,198,621 | B2 | 6/2012 | Rogers | |
| 8,207,473 | B2 | 6/2012 | Axisa | |
| 8,217,381 | B2 | 7/2012 | Rodgers | |
| 8,372,726 | B2 * | 2/2013 | de Graff et al. | 438/457 |
| 8,389,862 | B2 | 3/2013 | Arora et al. | |
| 8,431,828 | B2 | 4/2013 | Vanfleteren | |
| 8,440,546 | B2 | 5/2013 | Nuzzo | |
| 8,536,667 | B2 | 9/2013 | De Graff et al. | |
| 8,552,299 | B2 | 10/2013 | Rodgers | |
| 8,664,699 | B2 | 3/2014 | Nuzzo | |
| 8,679,888 | B2 | 3/2014 | Rodgers | |
| 8,729,524 | B2 | 5/2014 | Rodgers | |
| 8,754,396 | B2 | 6/2014 | Rodgers | |
| 8,865,489 | B2 | 10/2014 | Rodgers | |
| 8,886,334 | B2 | 11/2014 | Ghaffari et al. | |
| 8,905,772 | B2 | 12/2014 | Rodgers | |
| 2002/0094701 | A1 | 7/2002 | Biegelsen et al. | |
| 2002/0113739 | A1 | 8/2002 | Howard | |
| 2003/0214408 | A1 | 11/2003 | Grajales | |
| 2003/0236455 | A1 * | 12/2003 | Swanson et al. | 600/374 |
| 2004/0243204 | A1 | 12/2004 | Maghribi | |
| 2006/0038182 | A1 | 2/2006 | Rodgers | |
| 2006/0286785 | A1 | 12/2006 | Rogers | |
| 2008/0046080 | A1 | 2/2008 | Vanden Bulcke | |
| 2008/0157235 | A1 | 7/2008 | Rodgers | |
| 2008/0204021 | A1 | 8/2008 | Leussler et al. | |
| 2008/0249576 | A1 | 10/2008 | Johnson et al. | |
| 2009/0000377 | A1 | 1/2009 | Shipps et al. | |
| 2009/0107704 | A1 | 4/2009 | Vanfleteren | |
| 2009/0261828 | A1 | 10/2009 | Nordmeyer-Massner | |
| 2009/0294803 | A1 | 12/2009 | Nuzzo | |
| 2009/0322480 | A1 | 12/2009 | Benedict et al. | |
| 2010/0002402 | A1 | 1/2010 | Rodgers | |
| 2010/0059863 | A1 | 3/2010 | Rogers | |
| 2010/0072577 | A1 | 3/2010 | Nuzzo | |
| 2010/0087782 | A1 | 4/2010 | Ghaffari et al. | |
| 2010/0090824 | A1 | 4/2010 | Rowell et al. | |
| 2010/0116526 | A1 | 5/2010 | Arora et al. | |
| 2010/0178722 | A1 | 7/2010 | De Graff et al. | |
| 2010/0245011 | A1 | 9/2010 | Chatzopoulos et al. | |
| 2010/0271191 | A1 | 10/2010 | De Graff et al. | |
| 2010/0298895 | A1 | 11/2010 | Ghaffari et al. | |
| 2010/0317132 | A1 | 12/2010 | Rodgers | |
| 2010/0321161 | A1 | 12/2010 | Isabell | |
| 2011/0034912 | A1 | 2/2011 | De Graff et al. | |
| 2011/0054583 | A1 | 3/2011 | Litt | |
| 2011/0121822 | A1 | 5/2011 | Parsche | |
| 2011/0140897 | A1 | 6/2011 | Purks et al. | |
| 2011/0184320 | A1 | 7/2011 | Shipps | |
| 2011/0215931 | A1 | 9/2011 | Callsen et al. | |
| 2011/0218756 | A1 | 9/2011 | Callsen et al. | |
| 2011/0218757 | A1 | 9/2011 | Callsen et al. | |
| 2011/0220890 | A1 | 9/2011 | Nuzzo | |
| 2011/0277813 | A1 | 11/2011 | Rodgers | |
| 2012/0016258 | A1 | 1/2012 | Webster et al. | |
| 2012/0051005 | A1 | 3/2012 | Vanfleteren | |
| 2012/0052268 | A1 | 3/2012 | Axisa | |
| 2012/0065937 | A1 | 3/2012 | De Graff et al. | |
| 2012/0087216 | A1 | 4/2012 | Keung et al. | |
| 2012/0092178 | A1 | 4/2012 | Callsen et al. | |
| 2012/0092222 | A1 | 4/2012 | Kato et al. | |
| 2012/0157804 | A1 | 6/2012 | Rodgers | |
| 2012/0172697 | A1 | 7/2012 | Urman | |
| 2012/0226130 | A1 | 9/2012 | De Graff et al. | |
| 2012/0244848 | A1 | 9/2012 | Ghaffari et al. | |
| 2012/0256308 | A1 | 10/2012 | Helin | |
| 2012/0316455 | A1 | 12/2012 | Rahman et al. | |
| 2012/0327608 | A1 | 12/2012 | Rodgers | |
| 2013/0041235 | A1 | 2/2013 | Rogers et al. | |
| 2013/0099358 | A1 | 4/2013 | Elolampi et al. | |
| 2013/0100618 | A1 | 4/2013 | Rogers | |
| 2013/0118255 | A1 | 5/2013 | Callsen et al. | |
| 2013/0150693 | A1 | 6/2013 | D'angelo et al. | |
| 2013/0185003 | A1 | 7/2013 | Carbeck et al. | |
| 2013/0192356 | A1 | 8/2013 | De Graff et al. | |
| 2013/0200268 | A1 | 8/2013 | Rafferty et al. | |
| 2013/0225965 | A1 | 8/2013 | Ghaffari | |
| 2013/0245388 | A1 | 9/2013 | Rafferty | |

(56) References Cited

U.S. PATENT DOCUMENTS

| | | |
|---|---|---|
| 2013/0274562 A1 | 10/2013 | Ghaffari |
| 2013/0313713 A1 | 11/2013 | Arora |
| 2013/0316487 A1 | 11/2013 | De Graff |
| 2013/0320503 A1 | 12/2013 | Nuzzo |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora |
| 2015/0099976 A1 | 4/2015 | Ghaffari |
| 2015/0100135 A1 | 4/2015 | Ives |

FOREIGN PATENT DOCUMENTS

| | | |
|---|---|---|
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/049716 A1 | 4/2013 |
| WO | WO 2013/052919 A2 | 4/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |

OTHER PUBLICATIONS

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

International Search Report for International Application No. PCT/US2014/067026 dated Feb. 23, 2015, 2 pages.

Written Opinion for International Application No. PCT/US2014/067026 dated Feb. 23, 2015, 5 pages.

* cited by examiner

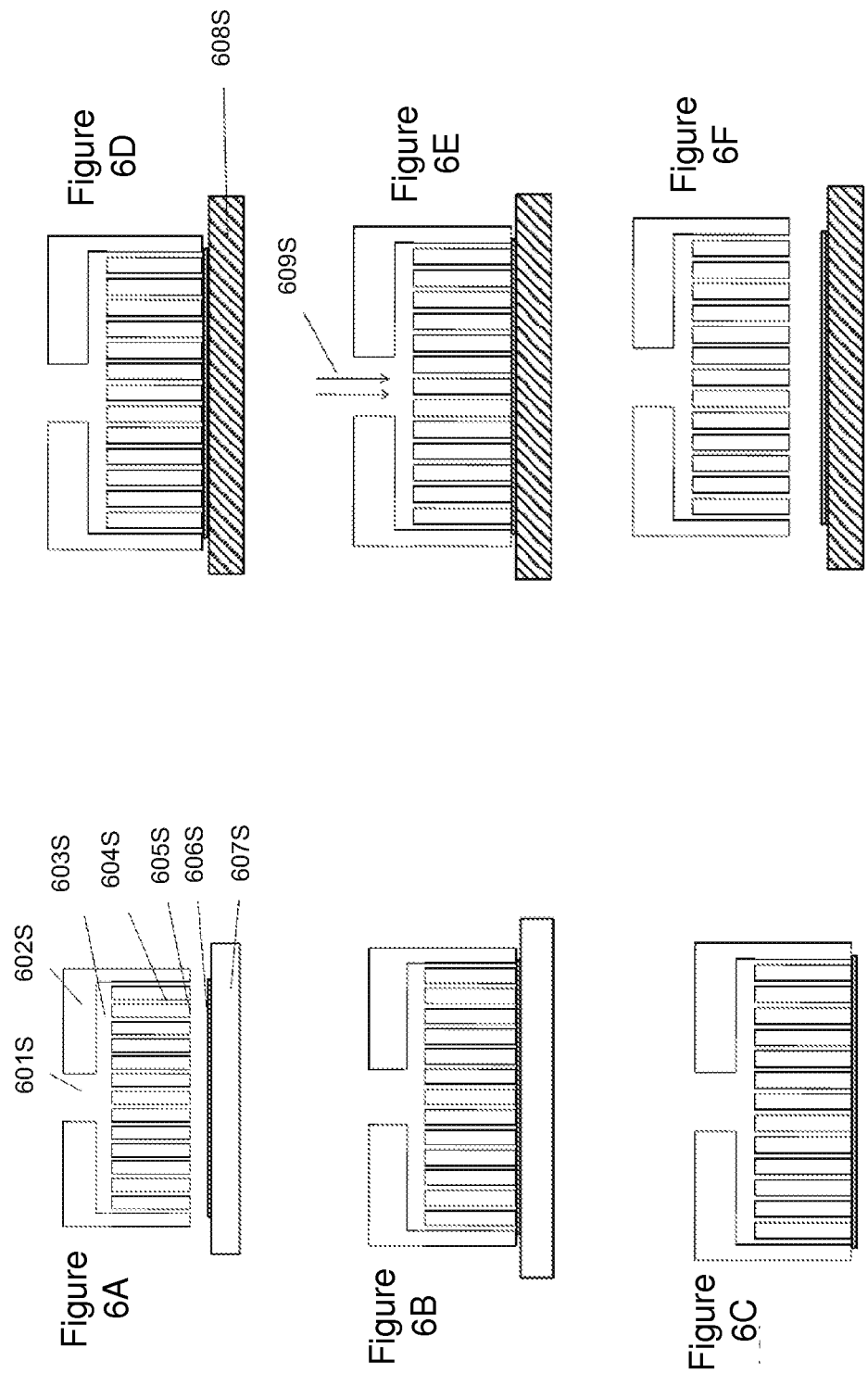

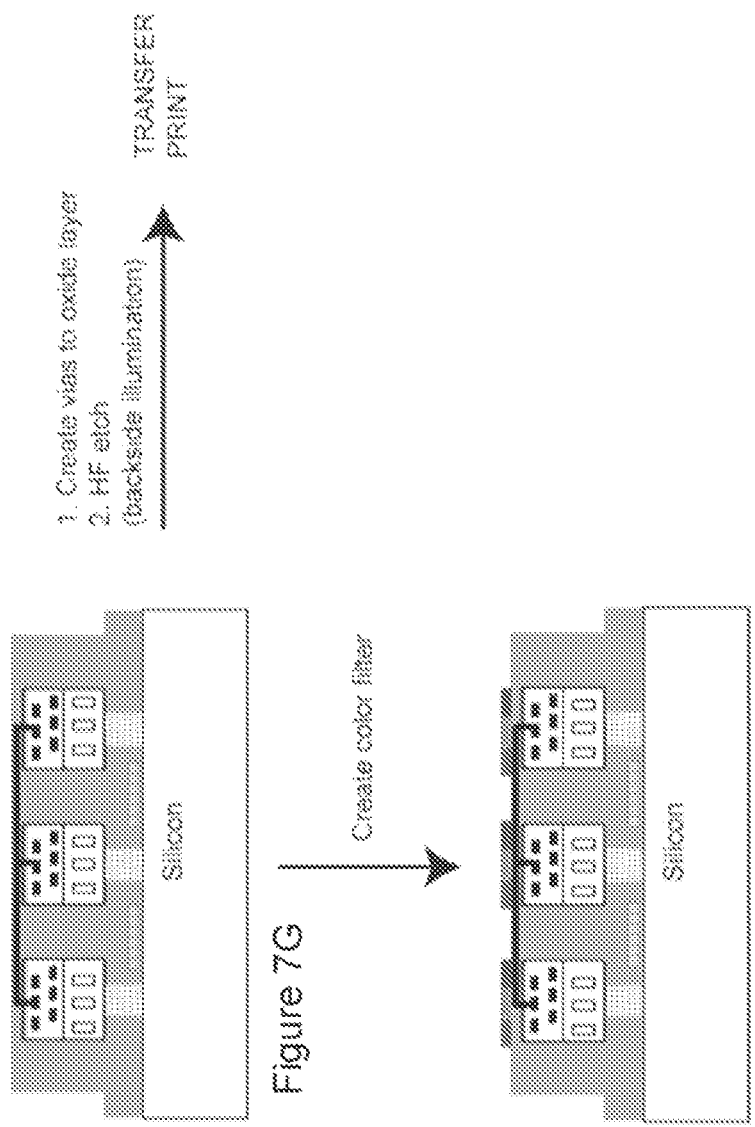

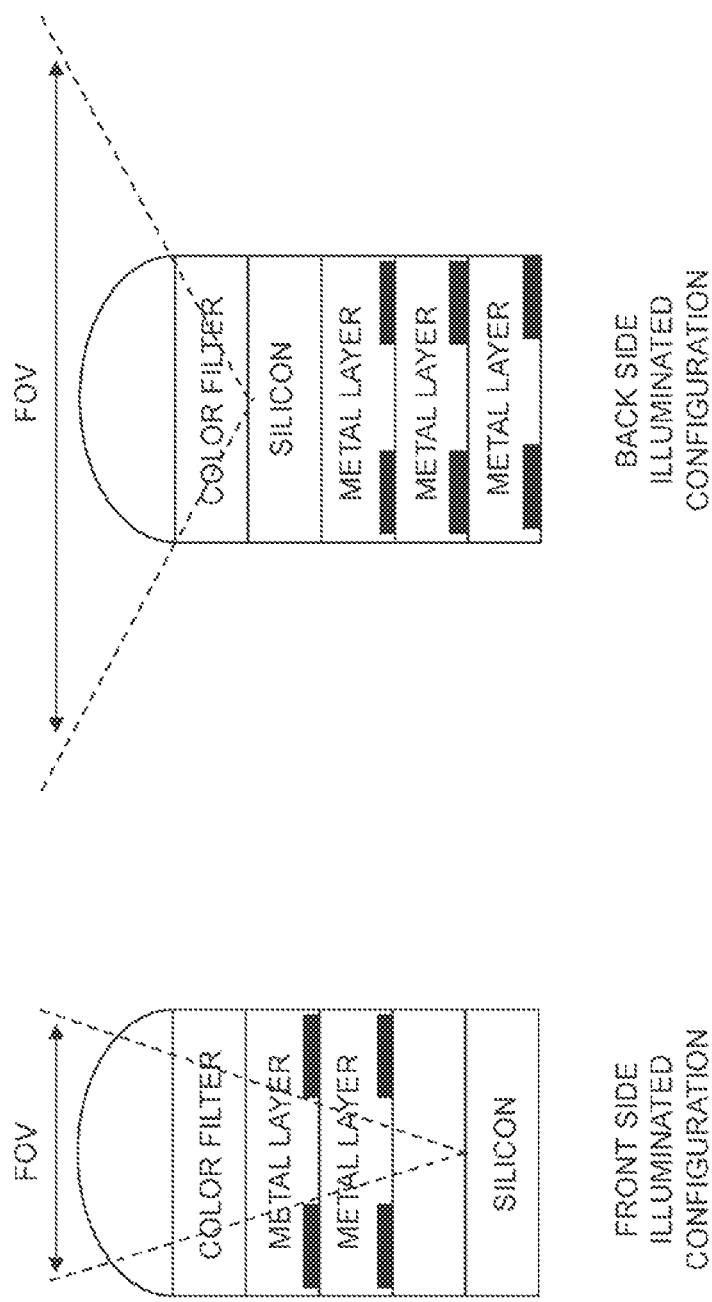

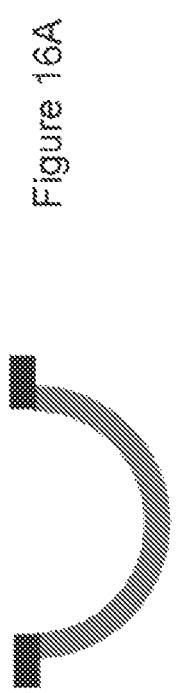
Figure 16A
Non-planar elastomeric stamp
Introduce strain by gentle heating or mechanical tool
Figure 16B
Planar, pre-strained elastomeric stamp

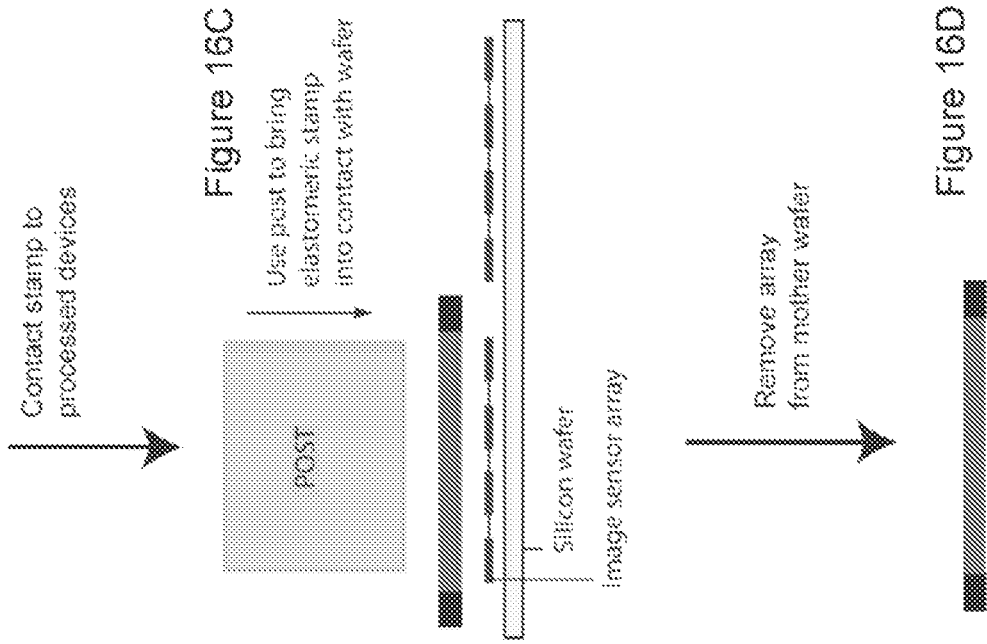

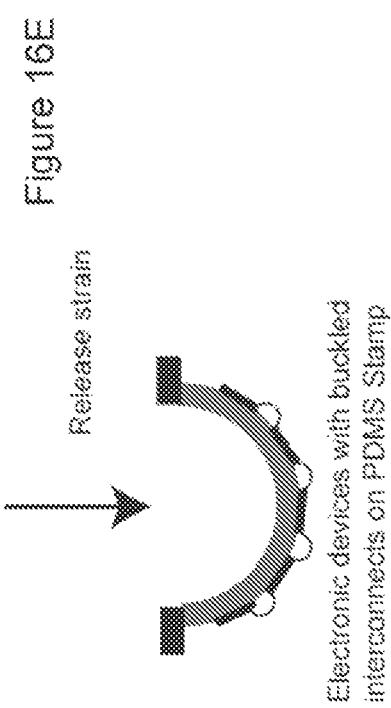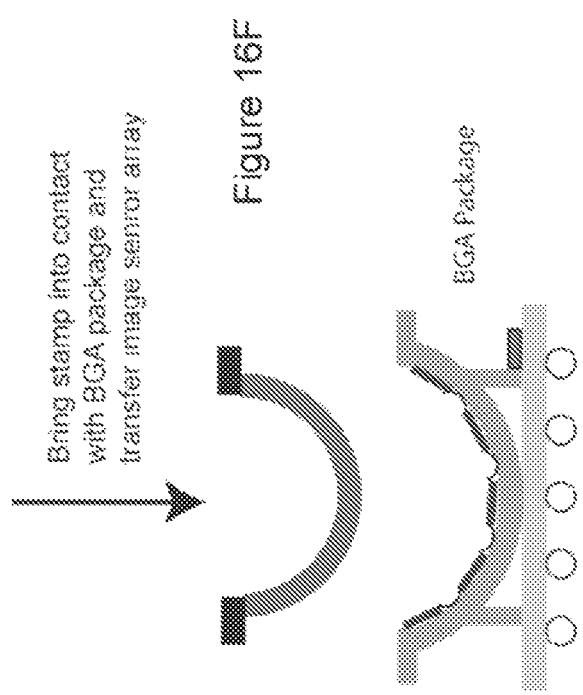

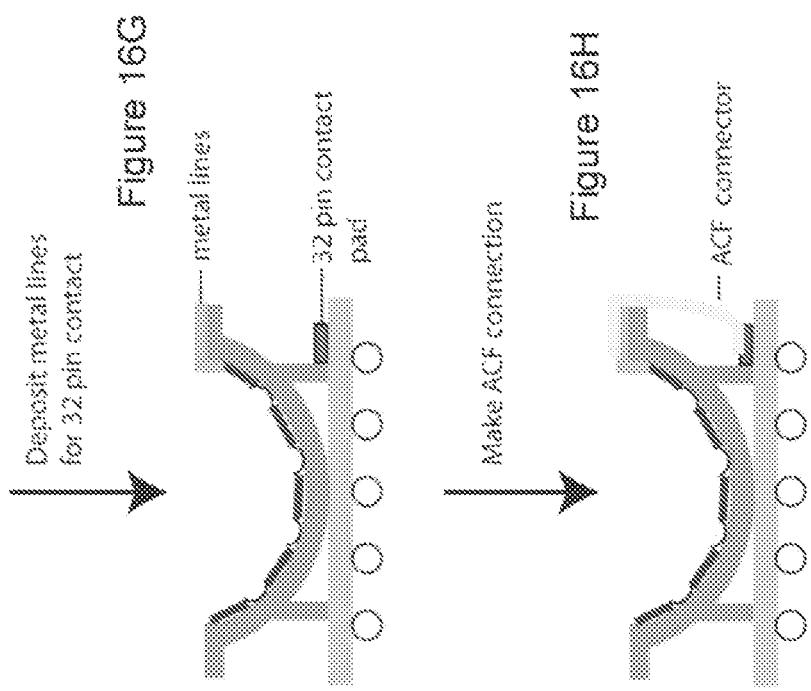

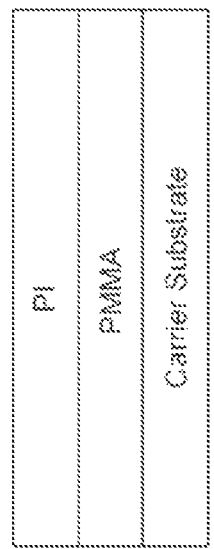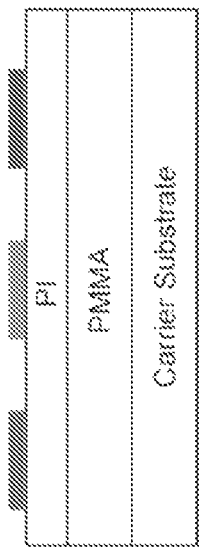

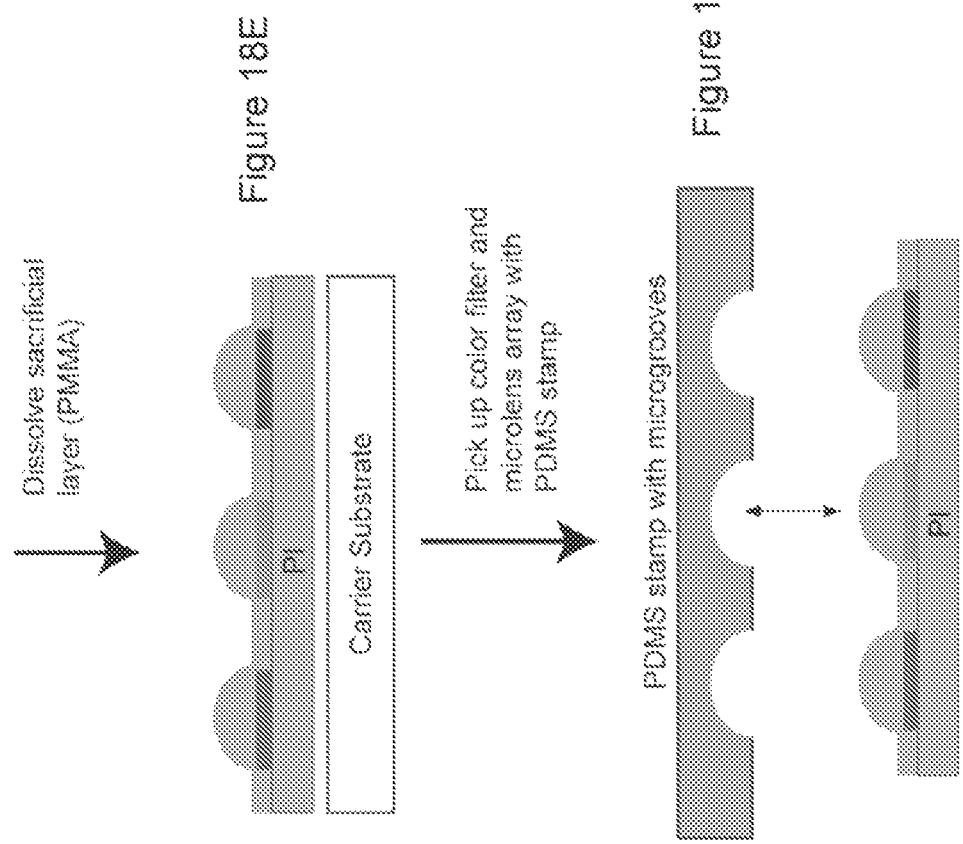

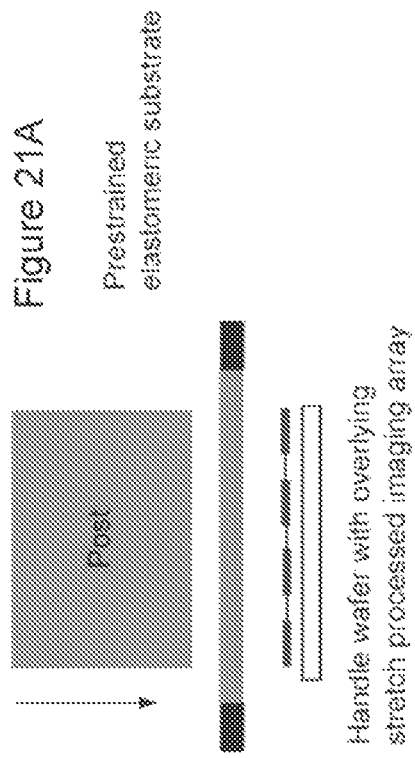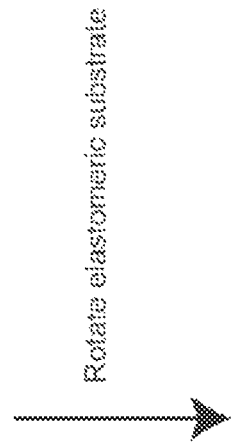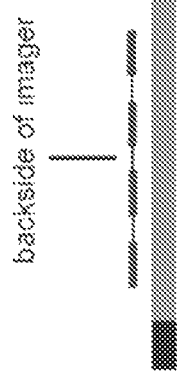
Figure 21A
Figure 21B

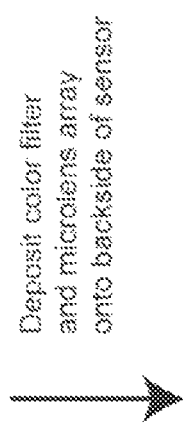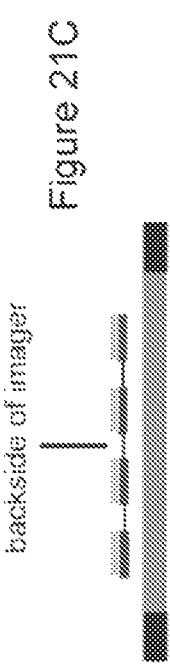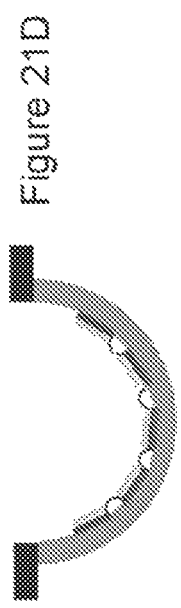

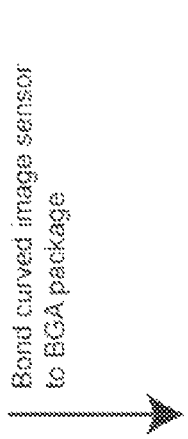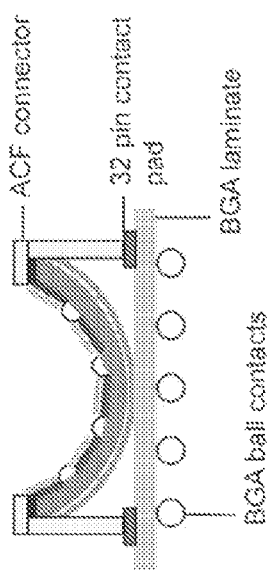

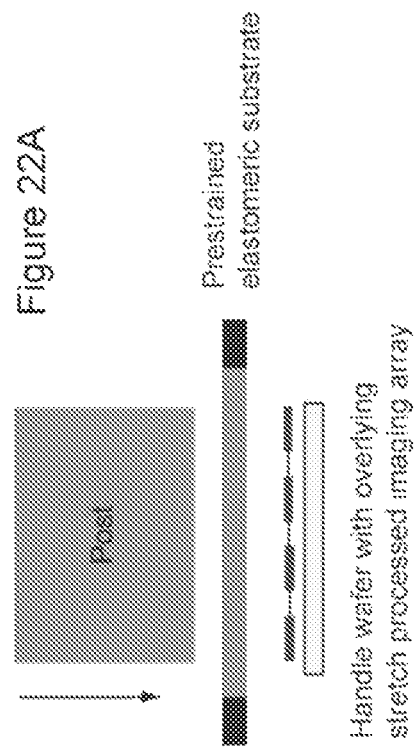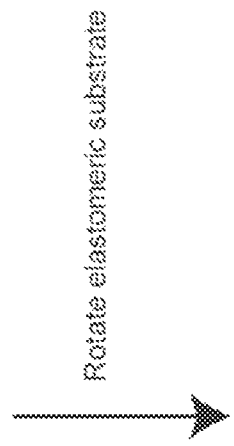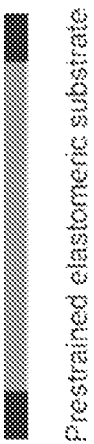

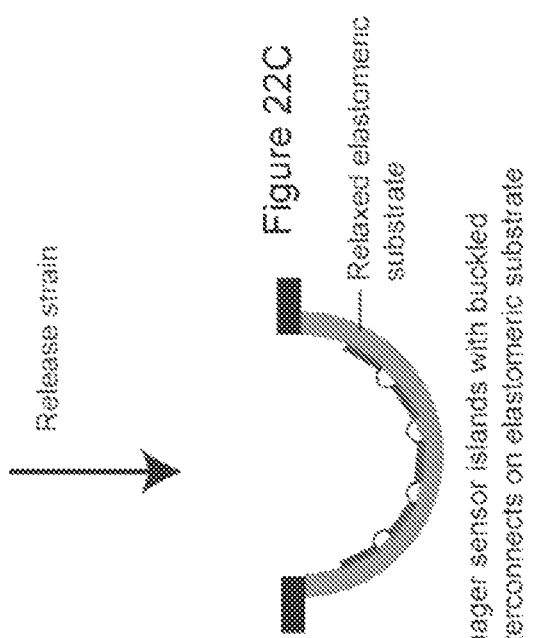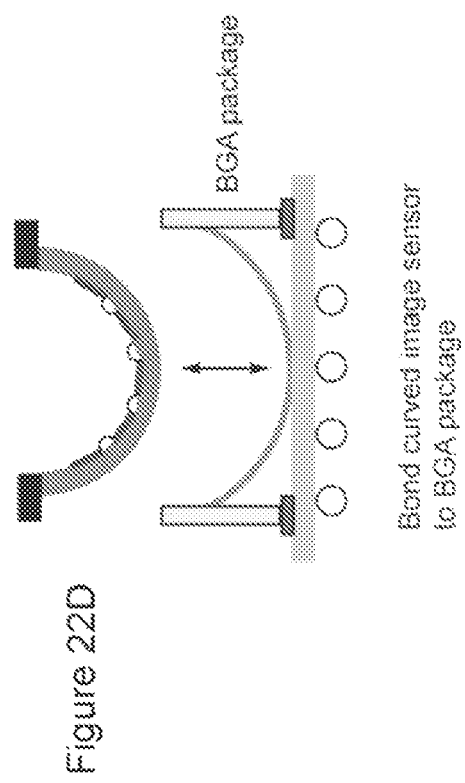

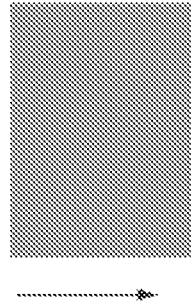
Figure 23A
Figure 23B

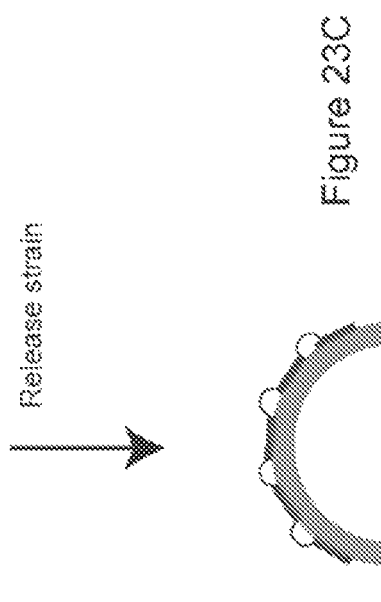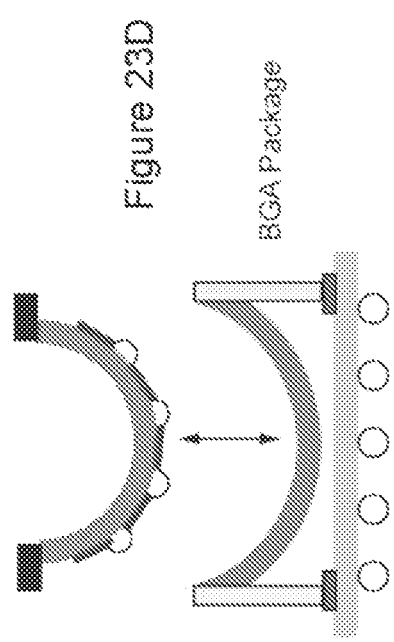

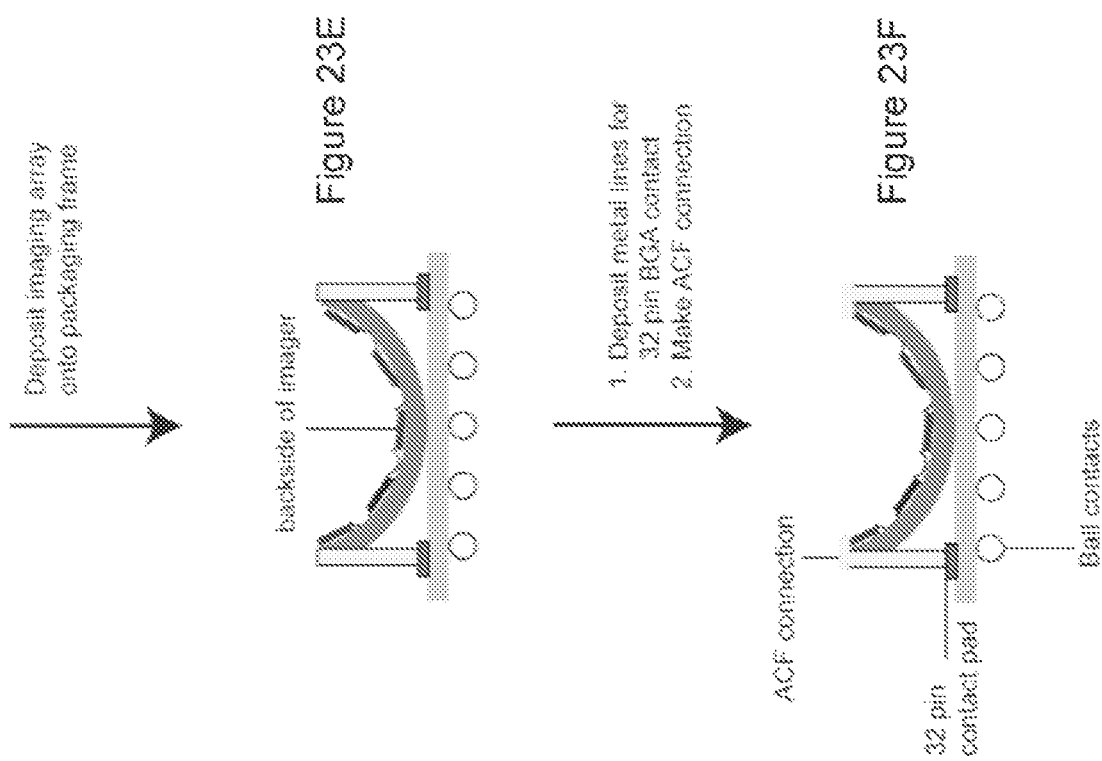

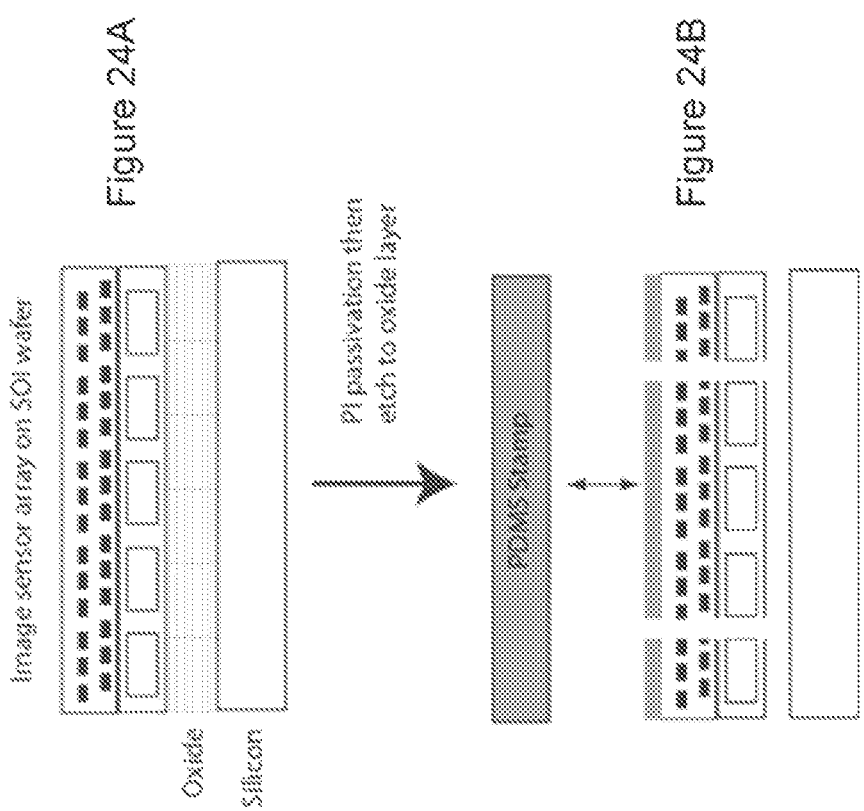

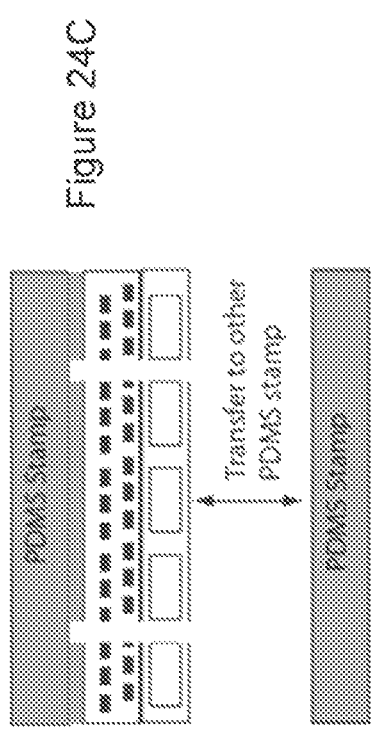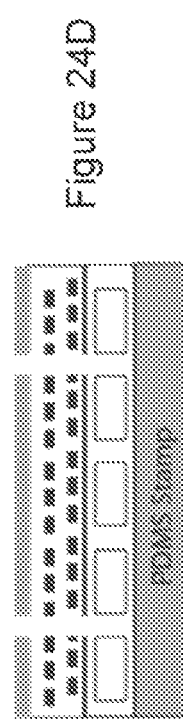

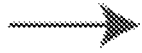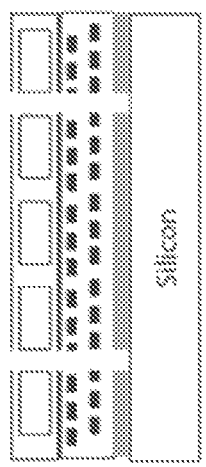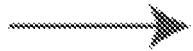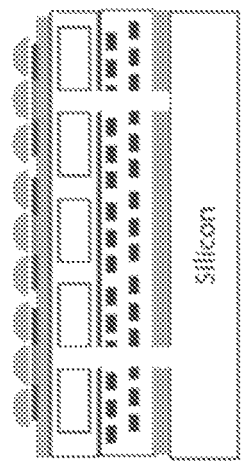

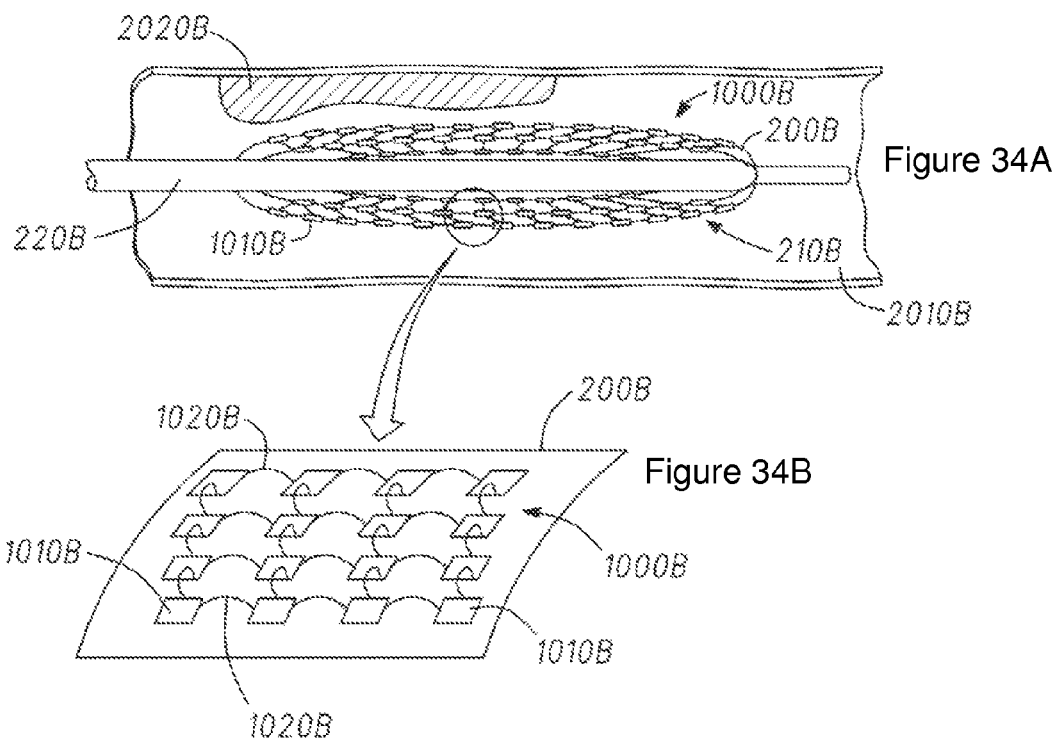
Figure 34A
Figure 34B
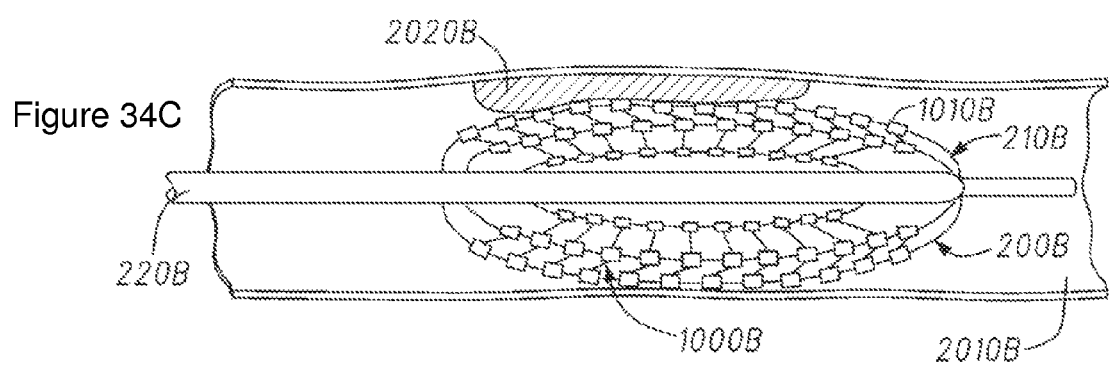
Figure 34C

SYSTEMS, METHODS AND DEVICES HAVING STRETCHABLE INTEGRATED CIRCUITRY FOR SENSING AND DELIVERING THERAPY

CROSS REFERENCE TO RELATED APPLICATIONS

This application is a division of U.S. Non-provisional application Ser. No. 13/336,518, entitled "Systems, Methods, and Devices Having Stretchable Integrated Circuitry for Sensing and Delivering Therapy," filed Dec. 23, 2011, now U.S. Pat. No. 8,536,667, issued Sep. 17, 2013, which is a continuation of U.S. Non-provisional application Ser. No. 12/723,475, entitled "Systems, Methods, and Devices Having Stretchable Integrated Circuitry for Sensing and Delivering Therapy," filed Mar. 12, 2010, now U.S. Pat. No. 8,097,926, issued Jan. 17, 2012, the entirety of which is hereby incorporated herein by reference.

U.S. Non-provisional application Ser. No. 12/723,475 claims the benefit of U.S. Provisional Application Ser. No. 61/160,185, entitled "Device for Monitoring Internal and External Heart Surface," filed Mar. 13, 2009, the entirety of which is hereby incorporated herein by reference. U.S. Non-provisional application Ser. No. 12/723,475 also claims the benefit of U.S. Provisional Application Ser. No. 61/164,920, entitled "Stretchable and Flexible Thin Film Electronic Devices," filed Mar. 31, 2009, the entirety of which is hereby incorporated herein by reference.

Also, U.S. Non-provisional application Ser. No. 12/723,475 is a continuation-in-part of U.S. Non-provisional application Ser. No. 12/686,076, entitled "Methods and Applications of Non-Planar Imaging Arrays," filed Jan. 12, 2010, now U.S. Pat. No. 8,372,726, issued Feb. 12, 2013, the entirety of which is incorporated herein by reference in its entirety. U.S. Non-provisional application Ser. No. 12/686,076 claims the benefit of the following U.S. Provisional Applications, each of which is incorporated herein by reference in its entirety: U.S. Provisional Application Ser. No. 61/144,149, entitled "Non-Planar Imaging Arrays," filed Jan. 12, 2009; and U.S. Provisional Application Ser. No. 61/156,906, entitled "Curved Imaging Array," filed Mar. 3, 2009. U.S. Non-provisional application Ser. No. 12/686,076 is a continuation-in-part of U.S. Non-provisional application Ser. No. 12/636,071, entitled "Systems, Methods, and Devices Using Stretchable or Flexible Electronics for Medical Applications," filed Dec. 11, 2009, now U.S. Pat. No. 8,886,334, issued Nov. 11, 2014, the entirety of which is hereby incorporated herein by reference. U.S. Non-provisional application Ser. No. 12/636,071 claims the benefit of the following U.S. Provisional Applications, the entirety of each of which is incorporated herein by reference: U.S. Provisional Application Ser. No. 61/121,568, entitled "Endoscopy Device," filed Dec. 11, 2008; U.S. Provisional Application Ser. No. 61/121,541, entitled "Nerve Bundle Prosthesis," filed Dec. 11, 2008; and U.S. Provisional Application Ser. No. 61/140,169, entitled "Body Tissue Screener," filed Dec. 23, 2008. U.S. Non-provisional application Ser. No. 12/636,071 is a continuation-in-part of U.S. Non-provisional application Ser. No. 12/616,922, entitled "Extremely Stretchable Electronics," filed Nov. 12, 2009, now U.S. Pat. No. 8,389,862, issued Mar. 5 2013, the entirety of which is incorporated herein by reference. U.S. Non-provisional patent application Ser. No. 12/616,922 claims the benefit of U.S. Provisional Application No. 61/113,622, entitled "Extremely Stretchable Interconnects," filed on Nov. 12, 2008, the entirety of which is incorporated herein by reference. Also, U.S. Non-provisional application Ser. No. 12/616,922 is a continuation-in-part of U.S. Non-provisional application Ser. No. 12/575,008, entitled "Catheter Balloon Having Stretchable Integrated Circuitry and Sensor Array," filed on Oct. 7, 2009, the entirety of which is incorporated herein by reference. U.S. Non-provisional application Ser. No. 12/575,008 claims the benefit to U.S. Provisional Application Ser. No. 61/103,361, entitled "Catheter Balloon Sensor and Imaging Arrays," filed Oct. 7, 2008, the entirety of which is incorporated herein by reference; and U.S. Provisional Application No. 61/113,007, entitled "Catheter Balloon with Sensor and Imaging Array," filed Nov. 10, 2008, the entirety of which is incorporated herein by reference.

FIELD OF THE INVENTION

The present invention relates to systems, apparatuses, and methods utilizing expandable or stretchable integrated circuitry comprising sensor or effector arrays on expandable, flexible or stretchable substrates in or on sensing or treatment devices.

BACKGROUND OF THE INVENTION

High quality medical sensing and imaging data has become important in the diagnoses and treatment of a variety of medical conditions include those related to conditions associated with the digestive system, conditions related to the cardiocirculatory system, injuries to the nervous system, cancer, and the like. Current sensing and therapeutic devices suffer from various disadvantages due to a lack of sophistication related to the sensing, imaging, and therapeutic functions. One of these disadvantages is that such devices are unable to achieve direct or conformal contact with the part of the body being measured or treated. The inability to achieve direct or conformal contact of such devices is partially attributable to the rigid nature of the devices and accompanying circuitry. This rigidity prevents devices from coming into conforming and/or direct contact with human tissue, which as is readily apparent, may change shape and size, and may be soft, pliable, curved, and/or irregularly shaped. Such rigidity thus compromises accuracy of measurements and effectiveness of treatment. Thus, devices, systems and methods that employ flexible and/or stretchable systems would be desirable.

Examples of categories that are amenable to such flexible and/or stretchable approaches include, endoscopy, vascular examination and treatment, neurological treatment and examination, tissue screening, cardiac ablation and mapping, conformal external tissue sensing and mapping among others. Controlled drug delivery as well a controlled delivery therapy such as ablation would also benefit from highly integrated stretchable electronics as will be demonstrated herein.

SUMMARY OF THE INVENTION

Stretchable and/or flexible electronics can mitigate or resolve many of the shortcomings described above and herein. Such techniques can be applied to the areas above, or to any area of physiological sensing, medical diagnostics, or treatment that would be improved by an integrated sensing and actuating facility. The invention applies to both treatment of humans and animals alike. In certain embodiments, the invention may apply in nonmedical areas as well.

Methods, systems, and devices are disclosed herein, which employ stretchable/and or flexible circuitry for improved sensing, including physiological sensing, detection of health-related parameters, and delivery of therapeutic measures. In embodiments, the circuitry is disposed on a stretchable, flexible, expandable, and/or inflatable substrate. In embodiments, circuitry comprises electronic devices, which may be active devices, in electronic communication with one another and programmed or configured to generate output and cause an output facility to display such output, deliver therapeutic measures, generate data regarding physiological parameters and/or make determinations of a health-related condition. Embodiments of the invention may include a storage facility in communication with the processing facility. The processing facility may cause at least one of data generated by the active devices and the output data to be stored in the storage facility and may generate output data related to the stored data. The processing facility may cause at least one of data generated by the active devices and the output data to be aggregated and may generate output data related to the aggregated data.

Some but not all embodiments are summarized below:

In embodiments of the invention, methods and systems include an apparatus for detecting and measuring aspects of a tissue of a subject's body that includes an expandable substrate on which is disposed stretchable circuitry configured to remain functional upon conforming to a surface of said tissue and including devices, which may be sensing devices to detect data indicative of a parameter of said tissue when said circuitry is in conformal contact with said tissue, and an array of imaging devices generating visual data; and a processing facility in electronic communication with said circuitry, receiving data indicative of a parameter of said tissue and visual data; and an output facility in electronic communication with said processing facility. The processing facility is configured to generate and display output data from the data indicative of a parameter of said tissue.

In embodiments of invention, methods and systems include an apparatus for measuring and detecting aspects of a tissue of a subject's body. The apparatus includes a stretchable substrate which contains circuitry configured to remain functional upon conforming to a surface of tissue. The circuitry contains a first array of sensing devices that contain contact sensors that generate data indicating that the array is in contact with tissue and generate data indicative of an area of the contact. The circuitry further contains a second array of sensing devices that detect data indicative of a parameter of the tissue. The apparatus also includes a processing facility that electronically communicates with the circuitry to receive data and activate sensing devices in the second array.

In an aspect of the invention, methods and systems include an apparatus to deliver therapy to a tissue. The apparatus contains a stretchable substrate that contains circuitry that can deliver therapy and is configured to remain functional upon conforming to a surface of the tissue. The apparatus contains a user interface configured to accept commands from an operator to activate the facility to deliver therapy and a processing facility in electronic communication with the circuitry and the user interface that receives a command from the operator and activates the facility to deliver therapy based on that command.

In an aspect of the invention, methods and systems include an apparatus to deliver ablative therapy to a tissue. The apparatus contains a stretchable substrate that contains stretchable circuitry that contains a facility to deliver ablative therapy and an array of sensors generating data indicative of electrical conduction of the tissue and is configured to remain functional upon conforming to a surface of the tissue. The apparatus contains an output facility that contains a user interface that is configured to accept a command from an operator to activate the facility to deliver ablative therapy. The apparatus contains a processing facility for generating and causing the output facility to display a map of conductive pathways in the tissue based on data indicative of electrical conduction of the tissue. The processing facility is in electronic communication with the circuitry and the output facility.

In embodiments, the processing facility is further configured to activate the facility to deliver ablative therapy based on a command from an operator to activate said facility to deliver ablative therapy. In embodiments, the processing facility is further configured to determine areas of tissue having an abnormal property. Further in embodiments, the tissue is cardiac tissue and the abnormal property comprises an arrhythmic region of the cardiac tissue.

In embodiments, the processing facility is further configured to suggest an area of the tissue on which to deliver ablative therapy. Further in embodiments, the suggestion is based, in part, on the data indicative of electrical conduction of the tissue. In embodiments, the suggestion is based, in part, on the areas of tissue having an abnormal property. Further in embodiments, the user interface provides the suggestion to an operator. In embodiments, the user interface comprises a facility to select an area on the tissue in which to deliver the ablative therapy. In embodiments, the facility to select an area on the tissue in which to deliver the ablative therapy is a graphical depiction of a suggested area in which to deliver ablative therapy.

In an aspect of the invention, methods and systems include a device to monitor physiological parameters of an individual that contains a sheet-like substrate provided with an adhesive for attachment to the individual's body and able to conform to the contours of the individual's body. The substrate contains stretchable circuitry that contains an array of devices that contains sensing devices configured to remain functional upon the substrate confirming to the contours of the individual's body. The device contains a processing facility in communication with the sensing devices and generating output based on data received from the sensing devices.

In an aspect of the invention, methods and systems include a flexible ECG monitoring device that contains a tape-like substrate provided with an adhesive for attachment to the individual's body and able to conform to the contours of the individual's body. The substrate contains electrodes for generating data relating to an ECG signal of an individual's heart. The device contains a transmitter to wirelessly transmit the data relating to an ECG signal of an individual's heart and a remote processing unit receiving the data relating to an ECG signal of an individual's heart.

In another aspect of the invention, methods and systems include a method to ablate tissue. The method consists of placing stretchable circuitry comprising an ablation facility into conformal contact with the tissue and activating the ablation facility while the ablation facility is in conformal contact with the tissue.

In another aspect of the invention, methods and systems include a method to accurately ablate a tissue. The method consists of placing device containing an array of electrical conductance sensors and an ablation facility in conformal contact with the tissue, determining an abnormality in the tissue with the data from the electrical conductance sensors, and activating said ablation facility to ablate abnormal tissue.

In another aspect of the invention, methods and systems include a method to accurately ablate a tissue. The method consists of placing a device containing an array of electrical conductance sensors and an ablation facility in conformal contact with the tissue, determining an abnormality in the tissue with the data from the electrical conductance sensors, providing a suggestion on an area of tissue to ablate based upon the determination of an abnormality in the tissue, providing an interface to select an area of the tissue to ablate, and activating the ablation facility to ablate abnormal tissue based on an area selected with the interface.

These and other inventions will become apparent in the disclosure below.

BRIEF DESCRIPTION OF THE DRAWINGS

The present invention will become more fully apparent from the following description and appended claims, taken in conjunction with the accompanying figures. Understanding that these figures merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying figures in which:

FIGS. 6A-F depict a method for controlled adhesion on an elastomeric stamp;

FIGS. 7A-K illustrates the process of creating an image sensor via stretch processing;

FIGS. 15A-B depict an illustration of the backside illumination concept;

FIGS. 16A-H outlines a method for transfer printing of "stretch processed" imaging arrays onto the curved surface of a BGA and the subsequent steps required to fabricate a BGA packaged curved image sensor;

FIGS. 18A-18F outlines steps in a method for fabricating curved backside illuminated imagers from stretch processed image sensors an incorporating it into a BGA package;

FIGS. 21A-F is a summary of a process for fabricating curved backside illuminated imagers from stretch processed image sensors and then incorporating them into a BGA package;

FIGS. 22A-E illustrates a process of creating a backside illuminated imager with no color filter or micro-lens;

FIGS. 23A-F illustrates a second method for creating a backside illuminated imager with no color filter or lens;

FIGS. 24A-F illustrates a method for creating a planar backside illuminated image sensor;

FIG. 34A depicts an embodiment of the invention wherein stretchable circuitry is applied to a balloon catheter, in which the balloon catheter is deflated;

FIG. 34B is a expanded view of the circuitry shown in FIG. 34A;

FIG. 34C depicts an embodiment of the invention wherein stretchable circuitry is applied to a balloon catheter, in which the balloon catheter is inflated;

DETAILED DESCRIPTION OF THE INVENTION

Figure 1A:
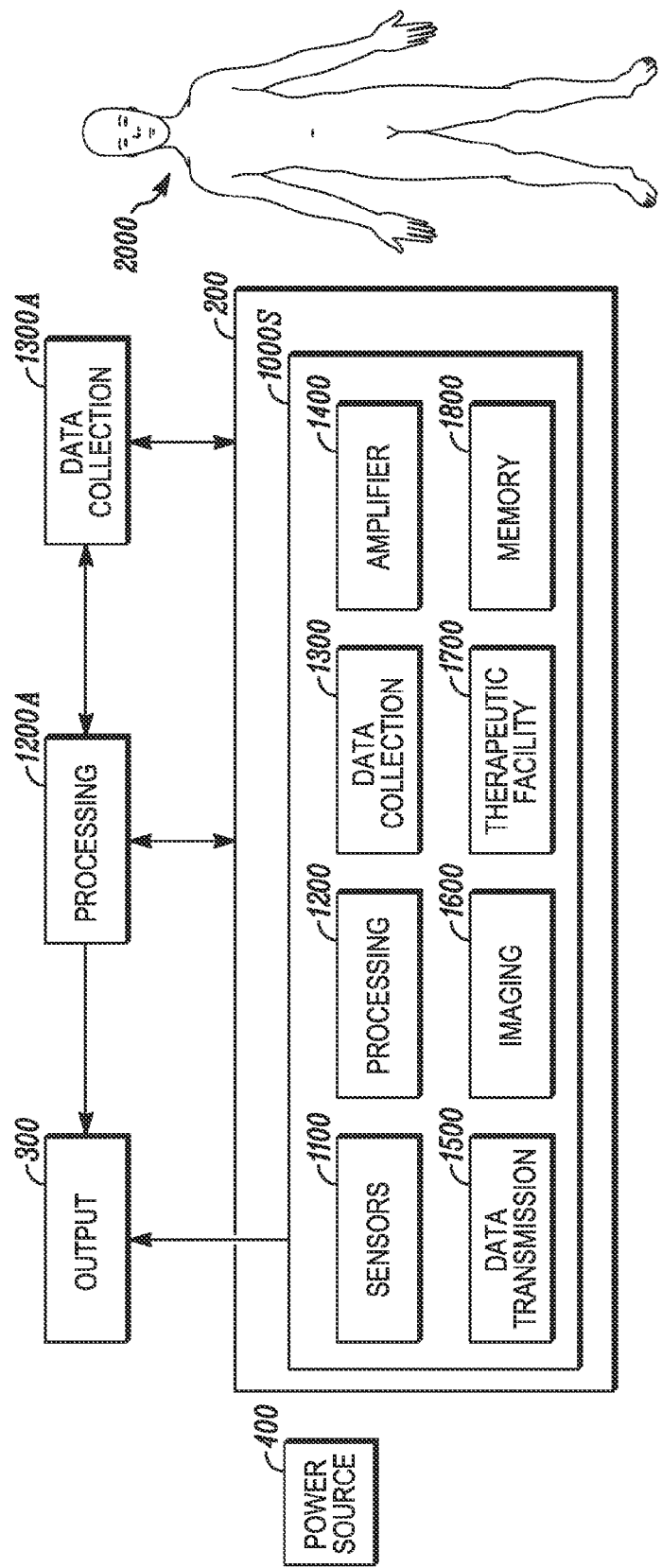
FIG. 1A is a schematic depiction of embodiments of the invention.

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "a" or "an," as used herein, are defined as one or more than one. The term "another," as used herein, is defined as at least a second or more. The terms "including" and/or "having" as used herein, are defined as comprising (i.e., open transition). The term "coupled" or "operatively coupled," as used herein, is defined as connected, although not necessarily directly and not necessarily mechanically or physically. "Electronic communication" is the state of being able to convey or otherwise transmit data either through a physical connection, wireless connection, or combinations thereof.

As described herein, the present invention comprises devices, systems, and methods utilizing flexible and/or stretchable electronic circuits on flexible, expandable, or inflatable surfaces. With reference to the present invention, the term "stretchable", and roots and derivations thereof, when used to modify circuitry or components thereof describes circuitry and/or components thereof having soft or elastic properties capable of being made longer or wider without tearing or breaking, and it is also meant to encompass circuitry having components (whether or not the components themselves are individually stretchable as stated above) that are configured in such a way so as to accommodate a stretchable, inflatable, or expandable surface and remain functional when applied to a stretchable, inflatable, or otherwise expandable surface that is stretched, inflated, or otherwise expanded respectively. The term "expandable," and roots and derivations thereof, when used to modify circuitry or components thereof is also meant to have the meaning ascribed above. Thus, "stretch" and "expand," and all derivations thereof, may be used interchangeably when referring to the present invention. The term "flexible", and roots and derivations thereof, when used to modify circuitry or components thereof describes circuitry and/or components thereof capable of bending without breaking, and it is also meant to encompass circuitry having components (whether or not the components themselves are individually flexible as stated above) that are configured in such a way so as to accommodate a flexible surface and remain functional when applied to a flexible surface that is flexed or otherwise bent. In embodiments, at the low end of 'stretchable,' this may translate into material strains greater than 0.5% without fracturing, and at the high end to structures that may stretch 100,000% without a degradation of electrical performance. "Bendable" and roots and derivations thereof, when used to modify circuitry or components thereof describes circuitry and/or components thereof able to be shaped (at least in part) into a curve or angle, and may sometimes be used synonymously herein with "flexible".

FIG. 1A is a schematic depiction of embodiments of the invention. Further description of each of the components of FIG. 1A will be included throughout the specification. Circuitry 1000S is applied, secured, or otherwise affixed to substrate 200. In embodiments, substrate 200 is stretchable and/or expandable as described herein. As such the substrate 200 can be made of a plastic material or can be made of an elastomeric material, or combinations thereof. Note that the term "plastic" may refer to any synthetic or naturally occurring material or combination of materials that can be molded or shaped, generally when heated, and hardened into a desired shape. The term "elastomer" may refer to a naturally occurring material or a synthetic material, and also to a polymeric material which can be stretched or deformed and return to its original shape without substantial permanent deformation. Such elastomers may withstand substantial elastic deformations. Examples of elastomers used in substrate material include polymeric organosilicon compounds (commonly referred to as "silicones"), including Polydimethylsiloxane (PDMS).

Other materials suitable for the substrate include polyimide; photopatternable silicone; SU8 polymer; PDS polydustrene; parylene and its derivatives and copolymers (parylene-N); ultrahigh molecular weight polyethylene; poly ether ether ketones (PEEK); polyurethanes (PTG Elasthane®, Dow Pellethane®); polylactic acid; polyglycolic acid; polymer composites (PTG Purisil PTG Bionate®, PTG Carbosil®); silicones/siloxanes (RTV 615®, Sylgard 184®); polytetrafluoroethylene (PTFE, Teflon®); polyamic acid; polymethyl acrylate; stainless steel; titanium and its alloys; platinum and its alloys; and gold. In embodiments, the substrate is made of a stretchable or flexible biocompatible material having properties which may allow for certain devices to be left in a living organism (referred to as the human body 2000) for a period of time without having to be retrieved. It should be noted that the invention applies to other living organisms, particularly mammals and should not be understood to be limited to humans.

Some of the materials mentioned above, specifically parylene and its derivatives and copolymers (parylene-N); ultrahigh molecular weight polyethylene; poly ether ether ketones (PEEK); polyurethanes (PTG Elasthane®, Dow Pellethane®); polylactic acid; polyglycolic acid; polymer composites (PTG Purisil PTG Bionate®, PTG Carbosil); silicones/siloxanes (RTV 615®, Sylgard 184®); polytetrafluoroethylene (PTFE, Teflon®); polyamic acid; polymethyl acrylate; stainless steel; titanium and its alloys; platinum and its alloys; and gold, are biocompatible. Coatings for the substrate to increase its biocompatibility may include, PTFE, polylactic acid, polyglycolic acid, and poly (lactic-co-glycolic acid).

The materials disclosed for substrate 200 herein may be understood to apply to any of the embodiments disclosed herein that require substrate. It should also be noted that materials can be chosen based on their properties which include degree of stiffness, degree of flexibility, degree of elasticity, or such properties related to the material's elastic moduli including Young's modulus, tensile modulus, bulk modulus, shear modulus, etc., and or their biodegradability.

The substrate 200 can be one of any possible number of shapes or configurations. In embodiments, the substrate 200 is substantially flat and in some embodiments configured to be a sheet or strip. Yet it should be noted that such flat configurations of substrate 200 could be any number of geometric shapes. Other embodiments of flat substrates will be described below including substrates having a tape-like or sheet configuration. Flexible and/or stretchable substrate 200 having a sheet or otherwise substantially flat configuration may be configured such that substrate 200 can be folded, furled, bunched, wrapped or otherwise contained. In embodiments, a substrate 200 configured as such can be folded, furled, bunched, collapsed (such as in an umbrella-like configuration), wrapped, or otherwise contained during delivery through narrow passageways in the subject's body 2000 and then deployed into an unfolded, unfurled, un-collapsed, etc. state once in position for deployment. As a non-limiting example, a furled substrate 200 carrying circuitry 100S comprising sensing device 1100 could be delivered via a catheter, then unfurled at such point when it is desired for the sensing device to contact the tissue of interest, such as the surface of the heart (inner or outer), or the inner surface of a lumen such as the pulmonary vein. In embodiments, substrates 200 may also be formed into concave and convex shapes, such as lenses. Such convex and concave substrates can be made of material suitable for contact with the eye, such as a contact lens, or for implantation into the eye, such a retinal or corneal implant.

Substrate 200 may also be three-dimensional. The three-dimensional substrate 200 can be any number of shapes. Such three-dimensional substrates may be a solid or substantially solid. In embodiments, the three-dimensional substrate may be pliable, flexible and stretchable while still comprising homogeneous or substantially homogenous material throughout its form, such as a foam or a flexible/stretchable polymeric sphere, ovoid, cylinder, disc, or other three-dimensional object. In embodiments, the three-dimensional substrate 200 may be made from several materials. In the presently preferred embodiment for the three-dimensional substrate 200, the substrate is an inflatable body (also referred to herein as an elastomeric vessel). Inflatable bodies of this type may be stretchable, such as a balloon or the like; however, in other embodiments, the inflatable body inflates without stretching. In embodiments, inflation can be achieved via a gas or liquid. In certain embodiments, inflation with a viscous fluid is preferable, but it should be clear that a variety of gases, fluids or gels may be employed for such inflation. Embodiments comprising balloon-like and disc-like inflatable substrates will be discussed in further detail below. The systems to achieve inflation discussed in connection with those embodiments apply to all inflatable embodiments of substrate herein.

In embodiments where the substrate 200 is stretchable, circuitry 1000S is configured in the applicable manners described herein to be stretchable and/or to accommodate such stretching of the substrate 200. Similarly, in embodiments where the substrate 200 is flexible, but not necessarily stretchable, circuitry 1000S is configured in the applicable manners described herein to be flexible and/or accommodate such flexing of the substrate 200. Circuitry 1000S can be applied and/or configured using applicable techniques described below, including those described in connection with exemplary embodiments.

As mentioned above, the present invention may employ one or more of a plurality of flexible and/or stretchable electronics technologies in the implementation thereof. Traditionally, electronics have been fabricated on rigid structures, such as on integrated circuits, hybrid integrated circuits, flexible printed circuit boards, and on printed circuit boards. Integrated circuits, also referred to as ICs, microcircuits, microchips, silicon chips, or simple chips, have been traditionally fabricated on a thin substrate of semiconductor material, and have been constrained to rigid substrates mainly due to the high temperatures required in the step of inorganic semiconductor deposition. Hybrid integrated circuits and printed circuit boards have been the main method for integrating multiple ICs together, such as through mounting the ICs onto a ceramic, epoxy resin, or other rigid non-conducting surface. These interconnecting surfaces have traditionally been rigid in order to ensure that the electrical interconnection methods, such as solder joints to the board and metal traces across the boards, do not break or fracture when flexed. In addition, the ICs themselves may fracture if flexed. Thus, the field of electronics has been largely constrained to rigid electronics structures, which then tend to constrain electronics applications that may require flexibility and or stretchability necessary for the embodiments disclosed herein.

Advancements in flexible and bendable electronics technologies have emerged that enable flexible electronics applications, such as with organic and inorganic semiconductors on flexible plastic substrates, and other technologies described herein. Further, stretchable electronics technologies have emerged that enable applications that require the electronics to be stretchable, such as through the use of mounting ICs on flexible substrates and interconnected through some method of stretchable electrical interconnect, and other technologies as described herein. The present invention may utilize one or more of these flexible, bendable, stretchable, and like technologies, in applications that require the electronics to operate in configurations that may not be, or remain, rigid and planar, such as applications that require electronics to flex, bend, expand, stretch and the like.

In embodiments, the circuitry of the invention may be made in part or in full by utilizing the techniques and processes described below. Note that the below description of the various ways to achieve stretchable and/or flexible electronics is not meant to be limiting, and encompasses suitable variants and or modifications within the ambit of one skilled in the art. As such, this application will refer to the following U.S. patents and patent applications, each of which is incorporated by reference herein in its entirety: U.S. Pat. No. 7,557,367 entitled "Stretchable Semiconductor Elements and Stretchable Electrical Circuits", issued Jul. 7, 2009 (the "'367 patent"); U.S. Pat. No. 7,521,292 entitled "Stretchable Form of Single Crystal Silicon for High Performance Electronics on Rubber Substrates", issued Apr. 29, 2009 (the "'292 patent"); United States Published Patent Application No. 20080157235 entitled "Controlled Buckling Structures in Semiconductor Interconnects and Nano membranes for Stretchable Electronics", filed Sep. 6, 2007 (the "'235 application"); U.S. patent application having Ser. No. 12/398,811 entitled "Stretchable and Foldable Electronics", filed Mar. 5, 2009 (the "'811 application"); United States Published Patent Application No. 20040192082 entitled "Stretchable and Elastic Interconnects" filed Mar. 28, 2003 (the "'082 application"); United States Published Patent Application No. 20070134849 entitled "Method For Embedding Dies", filed Nov. 21, 2006 (the "'849 application"); United States Published Patent Application No. 20080064125 entitled "Extendable Connector and Network, filed Sep. 12, 2007 (the "'125 application"); U.S. Provisional patent application having Ser. No. 61/240,262 (the "'262 application") "Stretchable Electronics", filed Sep. 7, 2009; U.S. patent application having Ser. No. 12/616,922 entitled "Extremely Stretchable Electronics", filed Nov. 12, 2009 (the "'922 application"); U.S. Provisional patent application having Ser. No. 61/120,904 entitled "Transfer Printing", filed Dec. 9, 2008 (the "'904 application"); United States Published Patent Application No. 20060286488 entitled "Methods and Devices for Fabricating Three-Dimensional Nanoscale Structures", filed Dec. 1, 2004; U.S. Pat. No. 7,195,733 entitled "Composite Patterning Devices for Soft Lithography" issued Mar. 27, 2007; United States Published Patent Application No. 20090199960 entitled "Pattern Transfer Printing by Kinetic Control of Adhesion to an Elastomeric Stamp" filed Jun. 9, 2006; United States Published Patent Application. No. 20070032089 entitled "Printable Semiconductor Structures and Related Methods of Making and Assembling" filed Jun. 1, 2006; United States Published Patent Application No. 20080108171 entitled "Release Strategies for Making Transferable Semiconductor Structures, Devices and Device Components" filed Sep. 20, 2007; and United States Published Patent Application No. 20080055581 entitled "Devices and Methods for Pattern Generation by Ink Lithography", filed Feb. 16, 2007.

"Electronic device" a/k/a "device" is used broadly herein to encompass an integrated circuit(s) having a wide range of functionality. In embodiments, the electronic devices may be devices laid out in a device island arrangement, as described herein including in connection to exemplary embodiments. The devices can be, or their functionality can include, integrated circuits, processors, controllers, microprocessors, diodes, capacitors, power storage elements, antennae, ASICs, sensors, image elements (e.g. CMOS, CCD imaging elements), amplifiers, A/D and D/A converters, associated differential amplifiers, buffers, microprocessors, optical collectors, transducer including electro-mechanical transducers, piezo-electric actuators, light emitting electronics which include LEDs, logic, memory, clock, and transistors including active matrix switching transistors, and combinations thereof. The purpose and advantage of using standard ICs (in embodiments, CMOS, on single crystal silicon) is to have and use high quality, high performance, and high functioning circuit components that are also already commonly mass-produced with well known processes, and which provide a range of functionality and generation of data far superior to that produced by a passive means. Components within electronic devices or devices are described herein, and include those components described above. A component can be one or more of any of the electronic devices described above and/or may include a photodiode, LED, TUFT, electrode, semiconductor, other light-collecting/detecting components, transistor, contact pad capable of contacting a device component, thin-film devices, circuit elements, control elements, microprocessors, interconnects, contact pads, capacitors, resistors, inductors, memory element, power storage element, antenna, logic element, buffer and/or other passive or active components. A device component may be connected to one or more contact pads as known in the art, such as metal evaporation, wire bonding, application of solids or conductive pastes, and the like.

Components incapable of controlling current by means of another electrical signal are called passive devices. Resistors, capacitors, inductors, transformers, and diodes are all considered passive devices For purposes of the invention, an active device is any type of circuit component with the ability to electrically control electron flow. Active devices include, but are not limited to, vacuum tubes, transistors, amplifiers, logic gates, integrated circuits, semiconducting sensors and image elements, silicon-controlled rectifiers (SCRs), and triode for alternating current (TRIACs).

"Ultrathin" refers to devices of thin geometries that exhibit flexibility.

"Functional layer" refers to a device layer that imparts some functionality to the device. For example, the functional layer may be a thin film, such as a semiconductor layer. Alternatively, the functional layer may comprise multiple layers, such as multiple semiconductor layers separated by support layers. The functional layer may comprise a plurality of patterned elements, such as interconnects running between device-receiving pads.

Semiconductor materials which may be used to make circuits may include amorphous silicon, polycrystalline silicon, single crystal silicon, conductive oxides, carbon annotates and organic materials.

In some embodiments of the invention, semiconductors are printed onto flexible plastic substrates, creating bendable macro-electronic, micro-electronic, and/or nano-electronic devices. Such bendable thin film electronics devices on plastic may exhibit field effect performance similar to or exceeding that of thin film electronics devices fabricated by conventional high temperature processing methods. In addition, these flexible semiconductor on plastic structures may provide bendable electronic devices compatible with efficient high throughput processing on large areas of flexible substrates at lower temperatures, such as room temperature processing on plastic substrates. This technology may provide dry transfer contact printing techniques that are capable of assembling bendable thin film electronics devices by depositing a range of high quality semiconductors, including single crystal Si ribbons, GaAs, INP wires, and carbon nano-tubes onto plastic substrates. This high performance printed circuitry on flexible substrates enables an electronics structure that has wide ranging applications. The '367 patent and associated disclosure illustrates an example set of steps for fabricating a bendable thin film electronics device in this manner. (See FIG. 26A of the '367 patent for Example).

In addition to being able to fabricate semiconductor structures on plastic, it has been demonstrated that metal-semiconductor electronics devices may be formed with printable wire arrays, such as GaAs micro-wires, on the plastic substrate. Similarly, other high quality semiconductor materials have been shown to transfer onto plastic substrates, including Si nano-wires, micro-ribbons, platelets, and the like. In addition, transfer-printing techniques using elastomeric stamps may be employed. The '367 patent provides an example illustration of the major steps for fabricating, on flexible plastic substrates, electronics devices that use arrays of single wires (in this instance GaAs wires) with epitaxial channel layers, and integrated holmic contacts. (See FIG. 41 of the '367 patent). In an example, a semi-insulating GaAs wafer may provide the source material for generating the microwires. Each wire may have multiple ohmic stripes separated by a gap that defines the channel length of the resultant electronic device. Contacting a flat, elastomeric stamp of PDMS to the wires forms a van der Waals bond. This interaction enables removal of all the wires from the wafer to the surface of the PDMS when the stamp is peeled back. The PDMS stamp with the wires is then placed against an uncured plastic sheet. After curing, peeling off the PDMS stamp leaves the wires with exposed ohmic stripes embedded on the surface of the plastic substrate. Further processing on the plastic substrate may define electrodes that connect the ohmic stripes to form the source, drain, and gate electrodes of the electronics devices. The resultant arrays are mechanically flexible due to the bendability of the plastic substrate and the wires.

In embodiments, and in general, stretchable electronics may incorporate electrodes, such as connected to a multiplexing chip and data acquisition system. In an example, an electrode may be fabricated, designed, transferred, and optionally encapsulated. In an embodiment, the fabrication may utilize and/or include an SI wafer; spin coating an adhesion layer (e.g. an HMDS adhesion layer); spin coating (e.g. PMMA) patterned by shadow mask, such as in oxygen RIE; spin coating Polyimide; depositing PECVD SiO2; spin 1813 Resist, photolithography patterning; metal evaporation (e.g. Ti, Pt, Au, and the like, or combination of the aforementioned); gold etchant, liftoff in hot acetone; spin Polyimide; PECVD SiO2; spin 1813 Resist, photolithography patterning; RIE etch, and the like. In this embodiment, the fabrication step may be complete with the electrodes on the Si wafer. In embodiments, the Si wafer may then be bathed in a hot acetone bath, such as at 100 C for approximately one hour to release the adhesion layer while PI posts keep electrode adhered to the surface of the Si wafer. In embodiments, electrodes may be designed in a plurality of shapes and distributed in a plurality of distribution patterns. Electrodes may be interconnected to electronics, multiplexing electronics, interface electronics, a communications facility, interface connections, and the like including any of the facilities/elements described on connection with FIG. 1A and/or the exemplary embodiments herein. In embodiments, the electrodes may be transferred from the Si wafer to a transfer stamp, such as a PDMS stamp, where the material of the transfer stamp may be fully cured, partially cured, and the like. For example, a partially cured PDMS sheet may be ~350 nm, where the PDMS was spun on at 300 rpm for 60 s, cured 65 C for 25 min, and used to lift electrodes off of the PDMS sheet. In addition, the electrodes may be encapsulated, such as wherein the electrodes are sandwiched between a supporting PDMS layer and second PDMS layer while at least one of the PDMS layers is partially cured.

In embodiments, stretchable electronics configurations may incorporate flex PCB design elements, such as flex print, chip-flip configurations (such as bonded onto the PCB), and the like, for connections to electrodes and/or devices, and for connections to interface electronics, such as to a data acquisition system (DAQ). For example, a flex PCB may be joined to electrodes by an anisotropic conductive film (ACF) connection, solder joints may connect flex PCB to the data acquisition system via conductive wires, and the like. In embodiments, the electrodes may be connected onto a surface by employing a partially cured elastomer (e.g. PDMS) as an adhesive.

In embodiments, stretchable electronics may be formed into sheets of stretchable electronics. In embodiments, stretchable sheets may be thin, such as approximately 100 μm. Optionally, amplification and multiplexing may be implemented without substantially heating the contact area, such as with micro-fluidic cooling.

In embodiments, a sheet having arrays of electronic devices comprising electrodes may be cut into different shapes and remain functional, such as through communicating electrode islands which determine the shape of the electrode sheet. Electrodes are laid out in a device island arrangement (as described herein) and may contain active circuitry designed to communicate with each other via inter-island stretchable interconnects so that processing facility (described herein) in the circuitry can determine in real-time the identity and location of other such islands. In this way, if one island becomes defective, the islands can still send out coordinated, multiplexed data from the remaining array. Such functionality allows for such arrays to be cut and shaped based on the size constraints of the application. A sheet, and thus circuitry, may be cut to side and the circuitry will poll remaining electrodes and/or devices to determine which are left and will modify the calibration accordingly. An example of a stretchable electronics sheet containing this functionality, may include electrode geometry, such as a 20×20 array of platinum electrodes on 1 mm pitch for a total area of 20×20 $mm^2$; an electrode impedance, such as 5 kohm at 1 khz (adjustable); a configuration in a flexible sheet, such as with a 50 μm total thickness, and polyimide encapsulated; a sampling rate, such as 2 kHz per channel; a voltage dynamic range, such as +/−6 mV; a dc voltage offset range, such as −2.5 to 5 V, with dc rejection; a voltage noise, such as 0.002 mV, a maximum signal-to-noise ratio, such as 3000; a leakage current, such as 0.3 μA typical, 10 μA maximum, as meets IEC standards, and the like; an operating voltage of 5 V; an operating power per channel, such as less than 2 mW (adjustable); a number of interface wires, such as for power, ground, low impedance ground, data lines, and the like; a voltage gain, such as 150; a mechanical bend radius, such as 1 mm; a local heating capability, such as heating local tissue by up to 1° C.; biocompatibility duration, such as 2 weeks; active electronics, such as a differential amplifier, a multiplexer (e.g. 1000 transistors per channel); a data acquisition system, such as with a 16 bit A/D converter with a 500 kHz sampling rate, less than 2 μV noise, data login and real-time screen display; safety compliance, such as to IEC10601; and the like.

In embodiments of the invention, mechanical flexibility may represent an important characteristic of devices, such as on plastic substrates, for many applications. Micro/nano-wires with integrated ohmic contacts provide a unique type of material for high performance devices that can be built directly on a wide range of device substrates. Alternatively, other materials may be used to connect electrical components together, such as connecting electrically and/or mechanically by thin polymer bridges with or without metal interconnects lines.

In embodiments, an encapsulation layer may be utilized. An encapsulating layer may refer to coating of the device, or a portion of the device. In embodiments, the encapsulation layer may have a modulus that is inhomogeneous and/or that spatially varies. Encapsulation layers may provide mechanical protection, device isolation, and the like. These layers may have a significant benefit to stretchable electronics. For example, low modulus PDMS structures may increase the range of stretchability significantly (described at length in the '811 application). The encapsulation layer may also be used as a passivation later on top of devices for the protection or electrical isolation. In embodiments, the use of low modulus strain isolation layers may allow integration of high performance electronics. The devices may have an encapsulation layer to provide mechanical protection and protection against the environment. The use of encapsulation layers may have a significant impact at high strain. Encapsulants with low moduli may provide the greatest flexibility and therefore the greatest levels of stretchability. As referred to in the '811 application, low modulus formulations of PDMS may increase the range of stretchability at least from 60%. Encapsulation layers may also relieve strains and stresses on the electronic device, such as on a functional layer of the device that is vulnerable to strain induced failure. In embodiments, a layering of materials with different moduli may be used. In embodiments, these layers may be a polymer, an elastomer, and the like. In embodiments, an encapsulation may serve to create a biocompatible interface for an implanted stretchable electronic system, such as Silk encapsulation of electronic devices in contact with tissue.

Returning to flexible and stretchable electronics technologies that may be utilized in the present invention, it has been shown that buckled and wavy ribbons of semiconductor, such as GaAs or Silicon, may be fabricated as part of electronics on elastomeric substrates. Semiconductor ribbons, such as with thicknesses in the submicron range and well-defined, 'wavy' and/or 'buckled' geometries have been demonstrated. The resulting structures, on the surface of, or embedded in, the elastomeric substrate, have been shown to exhibit reversible stretchability and compressibility to strains greater than 10%. By integrating ohmic contacts on these structured GaAs ribbons, high-performance stretchable electronic devices may be achieved. The '292 patent illustrates steps for fabricating stretchable GaAs ribbons on an elastomeric substrate made of PDMS, where the ribbons are generated from a high-quality bulk wafer of GaAs with multiple epitaxial layers (See FIG. 22 in the '292 patent). The wafer with released GaAs ribbons is contacted to the surface of a pre-stretched PDMS, with the ribbons aligned along the direction of stretching. Peeling the PDMS from the mother wafer transfers all the ribbons to the surface of the PDMS. Relaxing the prestrain in the PDMS leads to the formation of large-scale buckles/wavy structures along the ribbons. The geometry of the ribbons may depend on the prestrain applied to the stamp, the interaction between the PDMS and ribbons, and the flexural rigidity of the ribbons, and the like. In embodiments, buckles and waves may be included in a single ribbon along its length, due for example, to thickness variations associated with device structures. In practical applications, it might be useful to encapsulate the ribbons and devices in a way that maintains their stretchability. The semiconductor ribbons on an elastomeric substrate may be used to fabricate high-performance electronic devices, buckled and wavy ribbons of semiconductor multilayer stacks and devices exhibiting significant compressibility/stretchability. In embodiments, the present invention may utilize a fabrication process for producing an array of devices utilizing semiconductor ribbons, such as an array of CMOS inverters with stretchable, wavy interconnects. Also, a strategy of top layer encapsulation may be used to isolate circuitry from strain, thereby avoiding cracking.

In embodiments, a neutral mechanical plane (NMP) in a multilayer stack may define the position where the strains are zero. For instance, the different layers may include a support layer, a functional layer, a neutral mechanical surface adjusting layer, an encapsulation layer with a resultant neutral mechanical surface such as coincident with the functional layer, and the like. In embodiments, the functional layer may include flexible or elastic device regions and rigid island regions. In embodiments, an NMP may be realized in any application of the stretchable electronics as utilized in the present invention.

In embodiments, semiconductor ribbons (also, micro-ribbons, nano-ribbons, and the like) may be used to implement integrated circuitry, electrical interconnectivity between electrical/electronic components, and even for mechanical support as a part of an electrical/electronic system. As such, semiconductor ribbons may be utilized in a great variety of ways in the configuration/fabrication of flexible and stretchable electronics, such as being used for the electronics or interconnection portion of an assembly leading to a flexible and/or stretchable electronics, as an interconnected array of ribbons forming a flexible and/or stretchable electronics on a flexible substrate, and the like. For example, nano-ribbons may be used to form a flexible array of electronics on a plastic substrate. The array may represent an array of electrode-electronics cells, where the nano-ribbons are pre-fabricated, and then laid down and interconnected through metallization and encapsulation layers. Note that the final structure of this configuration may be similar to electronic device arrays as fabricated directly on the plastic, as described herein, but with the higher electronics integration density enabled with the semiconductor ribbons. In addition, this configuration may include encapsulation layers and fabrication steps which may isolate the structure from a wet environment. This example is not meant to limit the use of semiconductor ribbons in any way, as they may be used in a great variety of applications associated with flexibility and stretchability. For example, the cells of this array may be instead connected by wires, bent interconnections, be mounted on an elastomeric substrate, and the like, in order to improve the flexibility and/or stretchability of the circuitry.

Wavy semiconductor interconnects is only one form of a broader class of flexible and stretchable interconnects that may (in some cases) be referred to as 'bent' interconnects, where the material may be semiconductor, metal, or other conductive material, formed in ribbons, bands, wire, traces, and the like. A bent configuration may refer to a structure having a curved shape resulting from the application of a force, such as having one or more folded regions. These bent interconnections may be formed in a variety of ways, and in embodiments, where the interconnect material is placed on an elastomeric substrate that has been pre-strained, and the bend form created when the strain is released. In embodiments, the pre-strain may be pre-stretched or pre-compressed, provided in one, two, or three axes, provided homogeneously or heterogeneously, and the like. The wavy patterns may be formed along pre-strained wavy patterns, may form as 'pop-up' bridges, may be used with other electrical components mounted on the elastomer, or transfer printed to another structure. Alternately, instead of generating a 'pop-up' or buckled components via force or strain application to an elastomeric substrate, a stretchable and bendable interconnect may be made by application of a component material to a receiving surface. Bent configurations may be constructed from microwires, such as transferred onto a substrate, or by fabricating wavy interconnect patterns either in conjunction with electronics components, such as on an elastomeric substrate.

Figure 2:
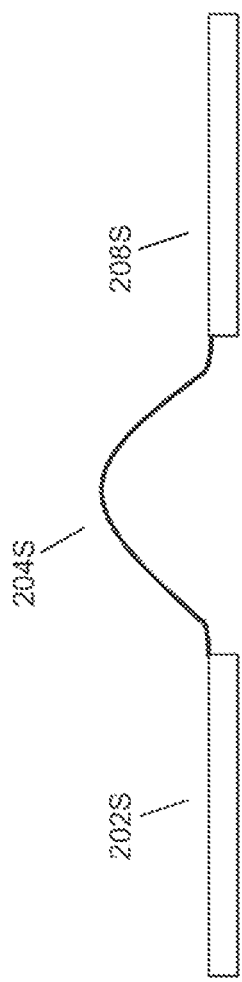
FIG. 2 depicts a buckled interconnection.

Semiconductor nanoribbons, as described herein, may utilize the method of forming wavy 'bent' interconnections through the use of forming the bent interconnection on a pre-strained elastomeric substrate, and this technique may be applied to a plurality of different materials. Another general class of wavy interconnects may utilize controlled buckling of the interconnection material. In this case, a bonding material may be applied in a selected pattern so that there are bonded regions that will remain in physical contact with the substrate (after deformation) and other regions that will not. The pre-strained substrate is removed from the wafer substrate, and upon relaxation of the substrate, the unbounded interconnects buckle ('pop-up') in the unbonded (or weakly bonded) regions. Accordingly, buckled interconnects impart stretchability to the structure without breaking electrical contact between components, thereby providing flexibility and/or stretchability. FIG. 2 shows a simplified diagram showing a buckled interconnection 204S between two components 202S and 208S.

In embodiments, any, all, or combinations of each of the interconnection schemes described herein may be applied to make an electronics support structure more flexible or bendable, such as applying bent interconnects to a flexible substrate, such as plastic or elastomeric substrates. However, these bent interconnect structures may provide for a substantially more expandable or stretchable configuration in another general class of stretchable electronic structures, where rigid semiconductor islands are mounted on an elastomeric substrate and interconnected with one of the plurality of bent interconnect technologies. This technology is presented here, and also in the '262 application, which has been incorporated by reference in its entirety. This configuration also uses the neutral mechanical plane designs, as described herein, to reduce the strain on rigid components encapsulated within the system. These component devices may be thinned to the thickness corresponding to the desired application or they may be incorporated exactly as they are obtained. Devices may then be interconnected electronically and encapsulated to protect them from the environment and enhance flexibility and stretchability.

Figure 3:
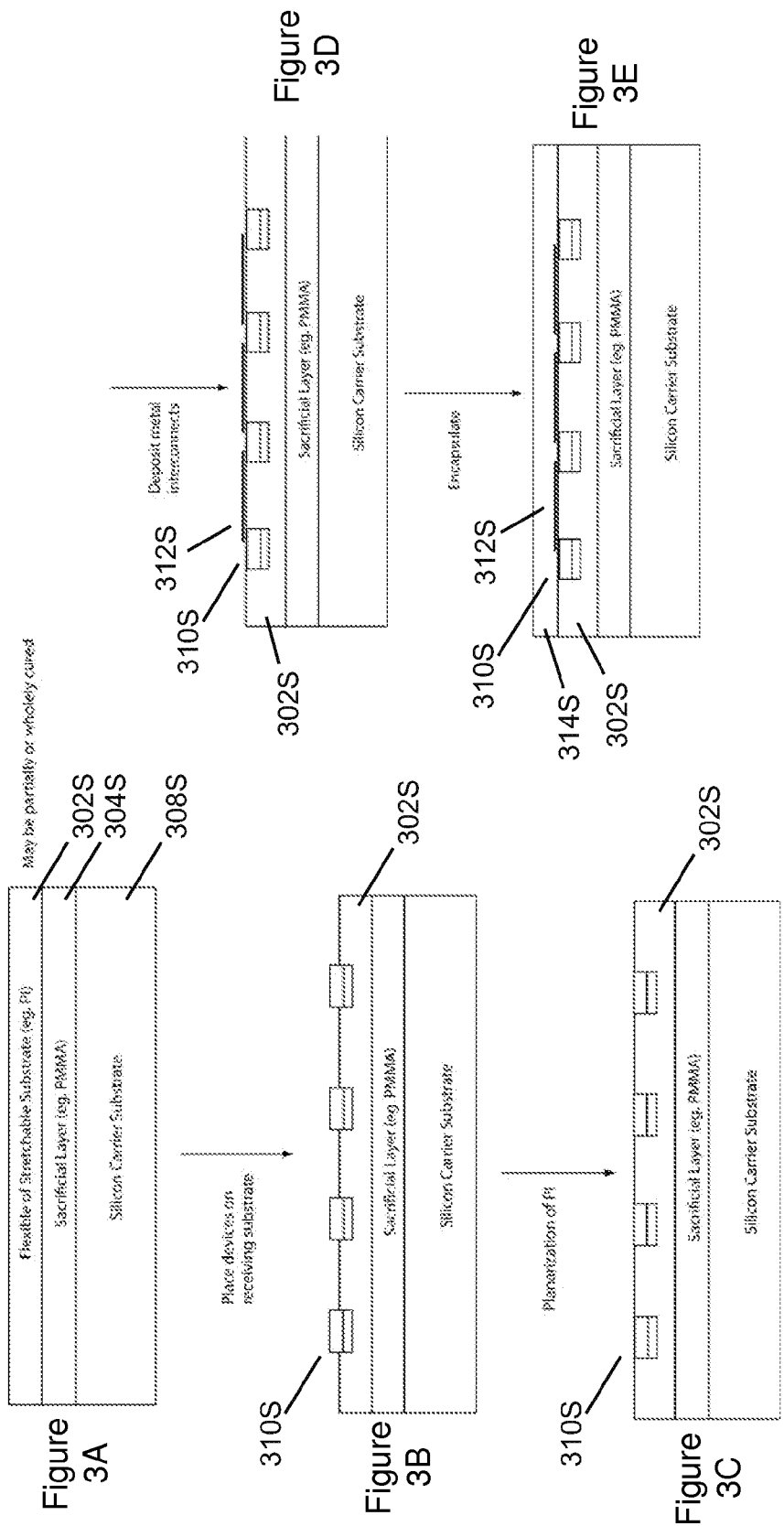
FIGS. 3A-E depict a stretchable electronics configuration with semiconductor islands mounted on an elastomeric substrate with stretchable interconnects.

In an embodiment, the first step in a process to create stretchable and flexible electronics as described herein involves obtaining required electronic devices and components and conductive materials for the functional layer. The electronics are then thinned (if necessary) by using a back grinding process. Many processes are available that can reliably take wafers down to 50 microns. Dicing chips via plasma etching before the grinding process allows further reduction in thickness and can deliver chips down to 20 microns in thickness. For thinning, typically a specialized tape is placed over the processed part of the chip. The bottom of the chip is then thinned using both mechanical and/or chemical means. After thinning, the chips may be transferred to a receiving substrate, wherein the receiving substrate may be a flat surface on which stretchable interconnects can be fabricated. FIG. 3 illustrates an example process, which begins by creating a flexible substrate 302S on the carrier 308S coated with a sacrificial layer 304S (FIG. 3A), placing devices 310S on the flexible substrate (FIG. 3B), and performing a planarization step in order to make the top surface of the receiving substrate the same height as that of the die surface (FIG. 3C). The interconnect fabrication process follows. The devices 310S deposited on the receiving substrate are interconnected 312S which join bond pads from one device to another (FIG. 3D). In embodiments, these interconnects 312S may vary from 10 microns to 10 centimeters. A polymeric encapsulating layer 314S may then be used to coat the entire array of interconnected electronic devices and components (FIG. 2E). The interconnected electronic devices are then released from the substrate by etching away sacrificial materials with a solvent. The devices are then ready to undergo stretch processing. They are transferred from the rigid carrier substrate to an elastomeric substrate such as PDMS. Just before the transfer to the new substrate, the arrays are pre-treated such that the device/component islands preferentially adhere to the surface leaving the encapsulated interconnects free to be displaced perpendicular to the receiving substrate.

In embodiments, the interconnect system is a straight metal line connecting two or more bond pads. In this case the electronic array is transferred to a pre-strained elastomeric substrate. Upon relaxation of this substrate the interconnects will be displaced perpendicular to the substrate, thus producing outward buckling. This buckling enables stretching of the system.

In another embodiment, the interconnects are a serpentine pattern of conductive metal. These types of interconnected arrays need not be deposited on a pre-strained elastomeric substrate. The stretchability of the system is enabled by the winding shape of the interconnects.

Stretchable/flexible circuits may be formed on paper, plastic, elastomeric, or other materials with the aid of techniques including but not limited to conventional photolithographic techniques, sputtering, chemical vapor deposition, ink jet printing, or organic material deposition combined with patterning techniques. Semiconductor materials which may be used to make circuits may include amorphous silicon, polycrystalline silicon, single-crystal silicon, conductive oxides, carbon nanotubes and organic materials. In embodiments, the interconnects may be formed of electrically conducting film, stripe, pattern, and the like, such as on an elastomer or plastic material, where the film may be made to buckle, deform, stretch, and the like, as described herein. In embodiments, the interconnect may be made of a plurality of films, such as on or embedded in the flexible and/or a stretchable substrate or plastic.

Figure 4:
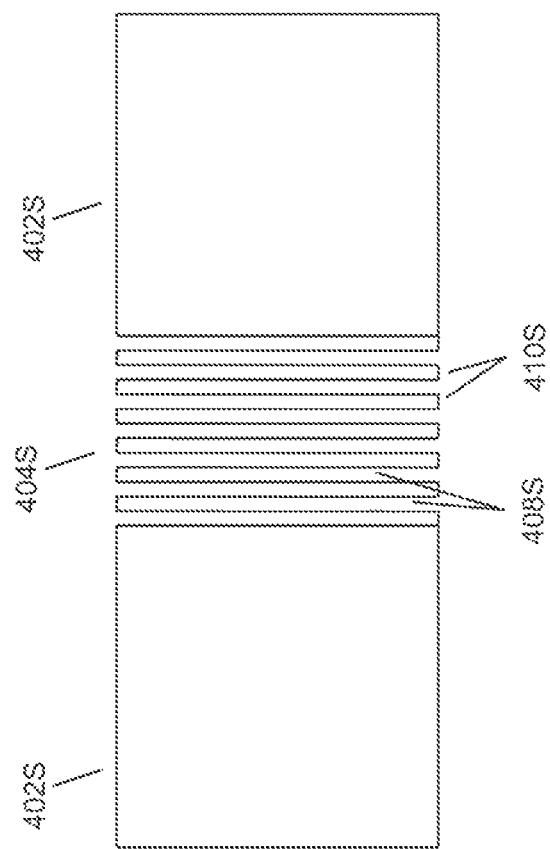
FIG. 4 depicts an extremely stretchable interconnect.

In embodiments, the interconnection of device islands 402S may utilize an extremely stretchable interconnect 404S, such as shown in FIG. 4, and such as the various configurations disclosed in the '922 application. The geometry and the dimension of the interconnects 404S is what makes them extremely compliant. Each interconnect 404S is patterned and etched so that its structural form has width and thickness dimensions that may be of comparable size (such as their ratio or inverse ratio not exceeding about a factor of 10); and may be preferably equal in size. In embodiments, the interconnect may be formed in a boustrophedonic style such that it effectively comprises long bars 408S and short bars 410S. This unique geometry minimizes the stresses that are produced in the interconnect when subsequently stretched because it has the effective form of a wire, and behaves very differently than interconnect form factors having one dimension greatly exceeding the other two (for example plates). Plate type structures primarily relieve stress only about a single axis via buckling, and withstand only a slight amount of shear stress before cracking. This invention may relieve stress about all three axes, including shears and any other stress. In addition, because the interconnect may be formed out of rigid materials, after being stretched it may have a restorative force which helps prevent its wire-like form from getting tangled or knotted when re-compressing to the unstretched state. Another advantage of the boustrophedonic geometry is that it minimizes the initial separation distance between the islands. In embodiments, the interconnects may be formed either monolithically (i.e., out of the same semiconductor material as the device islands) or may be formed out of another material.

Figure 5:
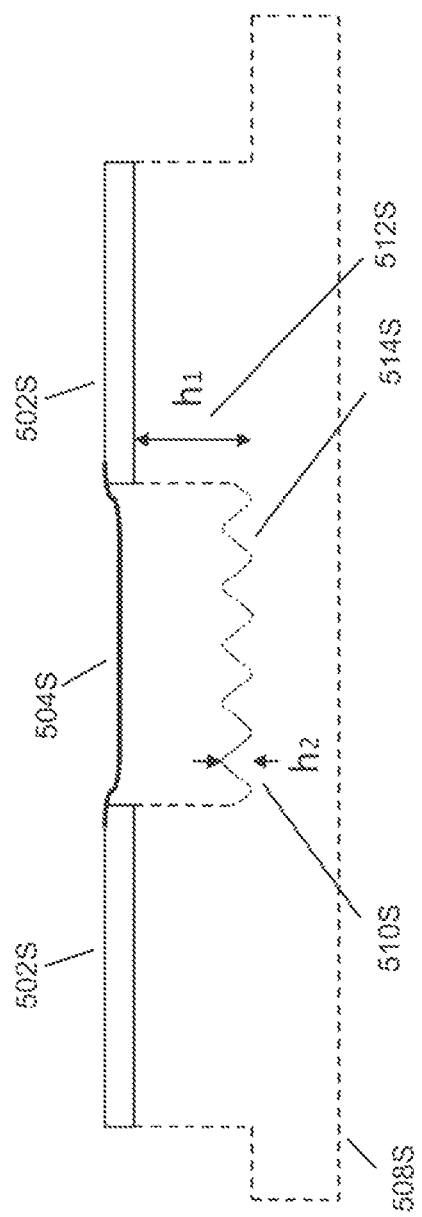
FIG. 5 depicts a raised stretchable interconnect with expandable elastomeric substrate.

In another embodiment the elastomeric substrate may comprise two layers separated by a height 512S, such as shown in FIG. 5. The top "contact" layer contacts the device island 502S, where the device islands 502S are interconnected 504S with one of the interconnection schemes described herein. In addition, the bottom layer may be a "wavy" layer containing ripples 514S or square waves molded into the substrate 508S during elastomer fabrication. These waves enable additional stretching, whose extent may depend on the amplitude 510S and wavelength of the waves pattern-molded in the elastomer.

In embodiments, the device island may be any prefabricated integrated circuit (IC), where the IC may be mounted on, inside, between, and the like, a flexible and/or stretchable substrate. For example, an additional elastomeric layer may be added above the structure as shown in FIG. 5, such as to encapsulate the structure for protection, increased strength, increase flexibility, and the like. Electrical contacts to embedded electrical components may be provided across the embedded layer, through the elastomeric layer(s) from a second electrical interconnection layer, and the like. For example, an IC may be encapsulated in a flexible material where the interconnects are made accessible as described in the '849 application. (See FIG. 1 of the '849 application for example). In this example the embedded IC is fabricated by first placing the IC onto a carrier, such as a rigid carrier, and where the IC may be a thinned IC (either thinned before the mounting on the carrier, or thinned while on the carrier). A second step may involve a coating of the IC with some adhesive, elastomer, or other insulating material that can be flowed onto the IC. A third step may be to gain access to the electrical contacts of the IC, such as by laser drilling or other method known to the art. A fourth step may be to flow electrical conductor into the openings, thus establishing a electrical access to the electrical connections of the IC. Finally, the IC thus encased may be freed from the carrier. Now the structure may be more easily embedded into a flexible substrate while maintaining electrical connectivity. In embodiments, this structure may be a flexible structure, due to the thinness of the IC, the elastic character of the surrounding structure, the elastic configuration of the extended electrical contacts, and the like.

It should be noted that many of the stretchable electronics techniques utilize the process of transfer printing, for example, with a PDMS stamp. In embodiments, the present invention may include a method of dynamically controlling the surface adhesion of a transfer printing stamp, such as described here, and disclosed in the '904 application. Transfer printing stamps have many uses, one of which is to pick up thin films of materials ("targets") from one surface ("initial surface") and deposit them onto another surface ("final surface"). The pickup may be achieved by pressing the transfer printing stamp into contact with the targets, applying some pressure to create Van der Waals bonds between the stamp and the targets, peeling off the stamp with the targets, and then placing the stamp with targets into contact with another surface, applying pressure, and peeling off the stamp without the targets so they remain on the final surface. If the final surface has a higher bonding strength with the targets than the transfer stamp, they will remain on the final surface when the transfer stamp is peeled off. Alternately, the rate of peeling the transfer stamp can be adjusted to vary the target to stamp and target to final surface bonding force ratio. The present invention describes a novel method of depositing the targets, by changing the surface adhesion of the transfer stamp after the targets have been picked up. This may be done while the stamp with targets is in contact with the final surface. In embodiments, the adhesion control can be done by introducing micro-fluidic channels into the transfer stamp, so that water or other fluid can be pumped to the surface of the stamp from within it, thereby changing the surface adhesion from sticky to non-sticky.

In embodiments, the present invention may accomplish transfer printing by using a transfer-printing stamp that has been formed with micro-fluidic channels such that a fluid (liquid or gas) can be pumped to the surface of the stamp to wet or chemically functionalize the surface and therefore change the surface adhesion of the stamp surface. The transfer-printing stamp may be made out of any material, including but not limited to poly-dimethyl-siloxane (PDMS) and derivatives thereof. In one non-limiting embodiment, the stamp is a piece of PDMS formed into a cuboid, which may have dimensions ranging from about 1 micrometer to 1 meter. For this example, the cuboid is 1 cm×1 cm×0.5 cm (length, width, thickness). One 1 cm×1 cm surface of the cuboid is designated as the stamping face. By using a photolithography mask, or a stencil mask, a pattern of vertical holes (channels) is etched from the stamping face through to the opposing face of the stamp. This may be done with an oxygen reactive ion etch. These holes are the micro-fluidic channels, and may be about 0.1-10 micrometers in diameter. They may be spaced apart by about 1-50 micrometers. Another piece of PDMS may be formed into a reservoir shape (e.g. a 1 cm×1 cm×0.5 cm cuboid with a smaller cuboid (about 0.8 cm×0.8 cm×0.3 cm) cut out from one surface). This shape may be formed by pouring the PDMS into a mold, curing it, and removing it from the mold. This additional piece of PDMS may then be placed into contact with the first piece of PDMS and bonded (this may be done via ultraviolet ozone exposure or oxygen plasma exposure of the PDMS prior to contacting the two pieces) such that the two pieces form the shape shown in FIG. 6, step A. Then, one or more holes may be punctured into the top of the reservoir so that a fluidic pipe can be fitted for pumping water into the stamp. In another non-limiting embodiment, the stamp is constructed as described above, except that the first piece of PDMS is formed to have micro-fluidic channels by means of molding. PDMS molding is a well-known art. First, a mold is created that is the inverse of the desired shape. In this case, that is an array of vertical posts on a base with four walls. This mold is then filled with PDMS by pouring in the PDMS, allowing it to cure (which may be at elevated temperature), and then removing the PDMS. In another non-limiting embodiment, the stamping surface is also patterned with an array of shallow-etched surface channels. In embodiments, these channels may be about 100-10000 nm wide, and 100-10000 nm etched-into the PDMS. They may form a linear array or a checkerboard grid. The purpose of the channels is to help distribute a liquid from the vertical micro-fluidic channels around the surface of the stamp. In addition, these channels serve to allow an exit for the air that must be displaced to push the liquid to the surface of the stamp. An example of a liquid that may be used includes, but is not limited to, water (which will wet the surface of the stamp and decrease its adhesivity). In the case of a gas fluid, these surface channels may not be necessary. Examples of gasses that can lower the surface adhesion of PDMS are dimethyldichlorosilane (DDMS), perfluorooctyl-trichlorosilane (FOTS), perfluorodecyltris (dimethylamino) silane (PF10TAS), and perfluorodecanoic acid (PFDA), and the like.

In embodiments, the stamp may be operated as shown in FIGS. 6A-6F. First, it is pressed into contact with a substrate that has the target material or devices to be picked up. (FIG. 6A). The target material is picked up by Van der Waal's forces between itself and the stamp as is well known (FIG. 6B,C). Target material is placed in contact with the final substrate, and pressed into contact (FIG. 6D). The fluid (for example, water) is pumped to the stamp surface, to reduce adhesion (FIG. 6E). The stamp may be left in this state (of contact with water) for as long as necessary for the water to fully wet the stamp surface. Finally, the stamp is removed, leaving the target material behind on the final substrate (FIG. 6F). In FIGS. 6A-F, the following labels are made for clarity: fluid inlet 601S; PDMS stamp 602S; fluid distribution reservoir 603S; micro-fluidic channels to stamp surface 604S; adhesive stamp surface 605S; devices to be picked up and transfer printed 6; initial substrate 607S; final substrate 608S; pump in water 609S so it reaches the end of the micro-fluidic channels to alter the surface adhesion of the transfer stamp and release the devices. Note that any surface channels on the stamp surface are not shown in the Figure, and the Figure is not drawn to scale.

Another example of configurations to enable stretchable circuitry are as described in the '125 application in connection with an extendable interconnect. (See FIG. 3 of the '125 application). The electrical component may be considered as one of a plurality of interconnected nodes, whose interconnections expand/extend as the underlying flexible substrate expands. In embodiments, flexible and stretchable electronics may be implemented in a great variety of ways, including configurations involving the substrate, the electrical components, the electrical interconnects, and the like, and involve electrical, mechanical, and chemical processes in their development and implementation.

While techniques for assembling stretchable or flexible circuitry will be discussed in connection with exemplary embodiments below, the above-described techniques should be understood to apply alone or in combination to achieve stretchable or flexible circuitry with any embodiment described herein.

As amply discussed herein, CMOS devices offer a variety sophisticated functionality including sensing, imaging, processing, logic, amplifiers, buffers, A/D converters, memory, clock and active matrix switching transistors. The electronic devices or the "device islands" of the stretchable/flexible circuitry of the present invention may be devices and are themselves capable of performing the functionality described herein, or portions thereof.

In embodiments, devices and device islands, devices may be "active" as described above.

In embodiments, the electronic devices are optionally laid out in a device island arrangement, as described herein. The functionality described herein with respect to circuitry 1000S and thus electronic devices may thus be present in an electronic device itself, spread across arrays of electronic devices and/or device components, or achieved via electronic communication and cooperation with other electronic devices and/or device components, each electronic device (or electronic device and device component combination) having separate or additive, but complementary functions that will become apparent from this disclosure. In embodiments, such electronic communication could be wireless. Therefore, said devices may comprise a transducer, transmitter, or receiver capable of such wireless transmission.

Returning to FIG. 1A, this figure schematically depicts the functionality of the circuitry 1000S (and thus the electronic devices, device components, or combinations thereof). Elements 1100-1700 and their sub-elements and components including electronic devices, device components, or combinations thereof may be present in the circuitry 1000S individually or in any combination as applicable. Certain combinations will be discussed below; however, the below discussions merely depict exemplary embodiments of the present invention and thus they are therefore not to be considered limiting of its scope. It will be readily appreciated that the elements of circuitry 1000S, as generally described herein, could be arranged and designed in a wide variety of different configurations. Nonetheless, the invention will be described and explained with additional specificity and detail.

Circuitry 1000S comprises sensors (also termed "sensor devices" herein) 1100 to detect various parameters of the subject's body including, thermal parameters such as temperature, and infrared; optical parameters; electrochemical and biochemical parameters such as, pH, enzymatic activity, blood components including blood gas and blood glucose, ion concentrations, protein concentrations; electrical parameters such as resistance, conductivity, impedance, EKG, EEG, and EMG; sound, and pressure, tactile, surface characteristics, or other topographic features of the subject material, including tissue. Thus, to achieve the detection of the above-mentioned parameters, sensors may include thermistors, thermocouples, silicon band gap temperature sensors, thin-film resistance temperature devices, LED emitters, optical sensors including photodetectors, electrodes, piezoelectric sensors, ultrasonic sensor including ultrasound emitters and receivers; ion sensitive field effect transistors, and microneedles. In embodiments, array of fluorescence detectors (e.g. CMOS imagers) for detecting the presence of proteins, enzymes, and other biological markers including indicators of a particular state, including disease state of an organism. Exemplary embodiments using one or more of the above sensors, or detecting and/or measuring one or more of the above parameters will be discussed below.

The separation distance between sensors (e.g., sensor device islands) can be any that is manufacturable, a useful range may be, but is not limited to, 10 μm-10000 μm. In embodiments, sensors 1100 can be characterized as sensor circuits. Individual sensors may be coupled to a differential amplifier, and/or a buffer and/or an analog to digital converter. The resulting sensor circuits may be formed on the same, or different, devices than the sensors themselves. The circuits may be laid out in such a way that the readings from multiple sensors 1100 can be switched into and processed by one or a few amplifier/logic circuits, which in embodiments is an active array or matrix fashion. Signals from the array of sensors 1100 can be processed using multiplexing techniques, including those described in published international patent application WO2009/114689 filed Mar. 12, 2009 the entirety of which is hereby incorporated herein by reference. Multiplexor component circuitry may be located on or within the circuitry 1000S on the substrate 200, or at a location that avoids interference with the operation of the device such as for example at the base of a catheter guide wire or balloon (which is relevant in embodiments where the substrate is a catheter balloon; although other areas that avoid interference with operation will be apparent.)

An advantage of the invention lies in the ability to utilize CMOS and microelectromechanical systems (MEMS) based sensor and imaging arrays. MEMS and CMOS based circuitry enable the use of a variety of sensing and imaging applications beyond just the sensing and application of electrical energy. These types of transistor-based components employ active feedback mechanisms and high performance processing speeds (nanosecond resolution) advanced beyond the performance of simple arrays of passive electrodes.

As discussed above, multiple sensors 1100 can be switched on and off and/or selectively operated, and the readings and processed by one or a few amplifier/logic circuits which may be comprised within the processing facility 1200 or 1200A. Similarly, any element of the circuitry including therapeutic facility 1700 described herein, including but not limited to sensors, effectors, drug delivery mechanisms, and stimulating electrodes may be switched on and off or otherwise operated selectively. In this way, devices, and device components of the circuitry can be selectively and dynamically activated/actuated. The selectively activated/operated elements of the circuitry may be viewed as functional nodes. Thus the processing facility 1200, 1200A may be programmed in such a way, e.g., comprising drivers, which may have the capability to selectively operate nodes based on user-input commands via an interface, or in closed-loop systems after processing data from other functional nodes in the circuitry, such nodes including but not limited to sensors or other electronic devices. Based on the capability to selectively operate multiple nodes, the system will thus have the ability to effectively change or select the number of electrical devices being operated in the circuitry, change or select the number of electronic devices being operated in an area of the circuitry, or change or select the spatial pattern of electrical devices being operated in the circuitry (e.g., sensing and/or effecting). In doing so, the operative density may be altered or selected. For example, density could be increased by increasing the number of nodes that are active per unit area. Further, the capability to selectively operate nodes enables the selection of specific functional nodes to operate. For example, circuitry could be configured to deliver ablative therapy to only those locations on the circuitry where the device is in conformal contact with the tissue of interest, such areas of conformal contact being determined based on data that the sensors have detected or generated. control (as an alternative or with density control). Another example, in an embodiment, comprises methods and to enable a sensing node (in combination with processing facility) to signal to a therapeutically active node whether to undertake activity in proximity to a region of interest. For example, a sensing node could indicate whether ablation is complete and signal for a cryo- or heating node to stop activity, while leaving other nodes active where those nodes are associated with regions where associated sensor nodes do not indicate completion of the activity.

The above may be useful for conserving energy and processing power which varies for every application.

Figure 1B:
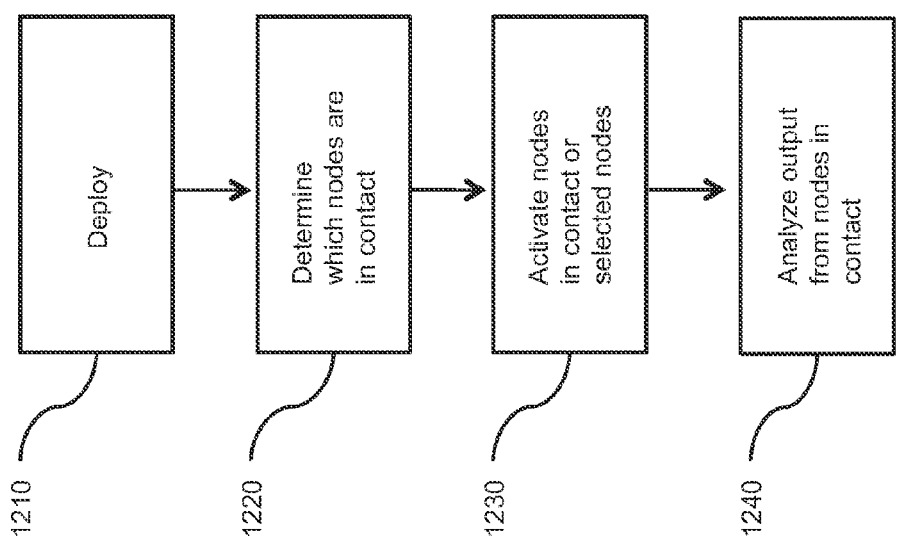
FIG. 1B depicts an embodiment of the invention wherein certain nodes on in the circuitry are activated based on their contact with a subject tissue.

FIG. 1B illustrates an embodiment of that which has been described above. At step 1210, the circuitry is deployed. Various methods of deployment (such as catheter-based delivery) will be described below and apply; however, deployment of the device is to place the device in contact with the tissue of interest. The contact may be partial. Contact may also be conformal with the tissue, which is enabled by the stretchable circuitry configurations described herein. Contact may also be electrical contact, which is described herein and which is enabled by the particular implementations of circuitry described herein. Contact may also be sensing contact, which is when the sensors of the devices are oriented relative to the tissue of interest such that consistent detection of the parameters of the tissue of interest may be obtained. Once deployed, processing facility 1200 or 1200A determines which of the nodes of the device are in contact with the tissue of interest, which is shown at step 1220. In closed loop systems, the device may activate nodes in contact, which is shown at 1230. Activation may comprise activating particular sensors at the locations in contact, or portions of the therapeutic facility determined to be in contact with said tissue of interest. In systems designed for a device operator, e.g., a clinician, the processing facility may be configured to provide the ability of the device operator to select, via a user interface, which nodes to activate (shown at 1230). Such selection may be informed by the nodes in contact, which in embodiments are communicated to the device operator. In embodiments, data detected from nodes in contact may be analyzed, including in any of the various manners described herein (shown at step 1240). The above capability applies to all embodiments herein, including all sensing, effecting, stimulating, and therapeutic facility embodiments. Certain exemplary embodiments utilizing this capability will be discussed below, but are not limiting in nature.

Another example of sensing capabilities involves the use of a fluorescence ELISA (Enzyme-linked immunosorbent assay) test. In embodiments, circuitry may comprise sensors to measure the intensity of fluorescence at each node to produce a map (in manners described herein) of enzymatic activity over a unit of space.

Circuitry 1000S comprises processing facility 1200 (alternatively referred to herein as "processor", "processing", and the terms mentioned immediately below) which may include a signal processor, digital processor, embedded processor, microcontroller, microprocessor, ASIC, or the like that may directly or indirectly facilitate execution of program code or program instructions stored thereon or accessible thereto. In addition, the processing facility 1200 may enable execution of multiple programs, threads, and codes. The threads may be executed simultaneously to enhance the performance of the processing facility 1200 and to facilitate simultaneous operations of the application. By way of implementation, methods, program codes, program instructions and the like described herein may be implemented in one or more thread. The thread may spawn other threads that may have assigned priorities associated with them; the processing facility 1200 may execute these threads based on priority or any other order based on instructions provided in the program code. The processing facility 1200 (and/or the circuitry 1000S in general) may include or be in electronic communication memory that stores methods, codes, instructions and programs as described herein and elsewhere. The processing facility 1200 may access a storage medium through an interface that may store methods, codes, and instructions to perform the methods and functionality described herein and elsewhere. Processing facility 1200 is comprised in or is in electronic communication with the other elements of the circuitry 1000S including the electronic devices and/or device components. Off-board processing facility 1200A comprises some or the functionality described above; however, is physically separate from circuitry 1000S yet in electronic communication thereto.

Processing facility is in communication with memory 1800 which may be within the circuitry or remote and in electrical communication with circuitry, or some combination thereof. Memory may perform all storage functions described herein including the storage of detected data and analytical data generated by the various embodiments herein, which may be used by the processing facility for historical analysis and tracking (as described in the embodiments herein).

Data collection facility 1300 (and off-board data collection facility 1300A) are configured to each independently or both collect and store data generated by the circuitry 1000S and the elements thereof including imaging facility 1600 (discussed below), and therapeutic facility 1700 (discussed below). Data transmission facility 1500 includes a means of transmitting (RF and/or wired) the sensor information to processing facility 1200 or off-board processing facility 1200A. Each of the elements 1100-1700 is also configured to be in electronic communication with one another and need not necessarily communicate through the data transmission facility 1500. In embodiments, circuitry 1000S and/or data transmission facility 1500 is in electronic communication with output facility 300 which, in embodiments, can be in electronic communication with processing facility 1200A or a separate processing facility. The various outputs described herein, such as visual maps based on sensed parameters, should be understood to emanate from the output facility 300, which in embodiments may be the display of a computing device.

Figure 1C:
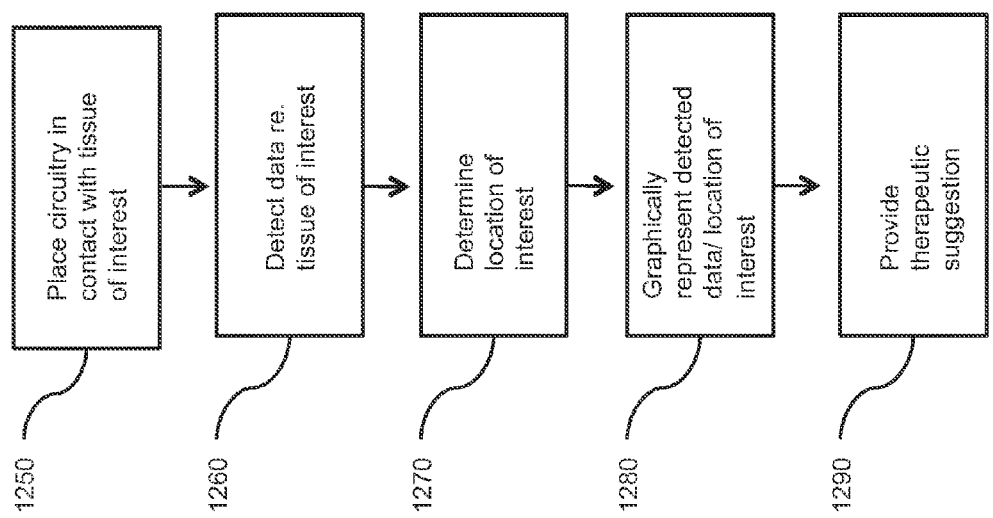
FIG. 1C depicts and embodiment of the invention to graphically represent areas of interest on a tissue and to provide therapeutic suggestions.

The invention's graphical presentation and mapping functionality will be described in connection with other embodiments herein and should be understood, in all embodiments, to comprise placing the circuitry into contact with the tissue of interest, shown as 1250 in FIG. 1C. The contact may be partial. Contact may also be conformal with the tissue, which is enabled by the stretchable circuitry configurations described herein. Contact may also be electrical contact, which is described herein and which is enabled by the particular implementations of circuitry described herein. Contact may also be sensing contact, which is when the sensors of the devices are oriented relative to the tissue of interest such that consistent detection of the parameters of the tissue of interest may be obtained. In embodiments for mapping, the circuitry will comprise sensors 1100, and will also comprise processing facility 1200 or be in communication with processing facility 1200A. Sensors 1100 may comprise any of the sensors disclosed herein in any combination and detect data from the tissue of interest (shown at step 1260). Processing facility receives data from the sensors. At step 1270, the processing facility is programmed to generate a graphical depiction comprising the detected data which may comprise a graphical depiction of an area of therapeutic interest, such as an area of abnormal electrical activity in the heart. The graphical depiction may comprise plots, charts, or graphs of historically sensed data for any measure of time. Data regarding sensed parameters may comprise data relating to which device and or which location on the circuitry generated the sensed data. In embodiments, the sensors are identified in a way such that their location on the substrate is known. In this way, sensed parameters can be correlated with locations in the circuitry or on the substrate. Combined with data regarding location of the circuitry (and components thereof) relative to the tissue of interest, such data can be stored and used by the processing facility, which when so programmed, can generate a visual depiction of the data associated with the sensed parameters in the form of a map. The map may be two or three-dimensional. Such maps may comprise maps of the electrical conductivity, the impedance, or the resistance of the tissue of interest. Such maps may comprise maps of the thermal properties of the tissue of interest. In other embodiments, utilizing contact, pressure or tactile sensors, the map may represent mechanical or topographical properties of the tissue and items including but not limited, temperature, pressure, electrical conductivity, pH, chemical, and/or enzymatic activity of a tissue of interest. In embodiments where an area of therapeutic interest is displayed, the processing facility may provide a therapeutic suggestion, for example, markers indicating where to direct ablative therapy (shown) generally at step 1290. Other specific aspects of the mapping and therapeutically suggestive capabilities of the invention, and/or of the nature of such maps will be discussed in connection with specific embodiments below.

Circuitry 1000S may be connected or otherwise in electronic communication with external/separate devices and systems by physical connection, including the methods described above and by providing conductive pads on the circuitry 1000S in an accessible location or location that avoids interference with the operation of the device and interfacing anisotropic conductive film (ACF) connectors to the conductive pads. Also, the circuitry 1000S and/or associated devices 10105 may comprise a transducer, transmitter, transceiver, or receiver capable of wireless transmission and thus wireless communication with external/separate devices and systems. In addition, circuitry 1000S islands may be made to perform optical data communication down a waveguide, such as the one described below.

Power source 400 can supply power to circuitry 1000S in any number of ways, including externally optically, with a waveguide and having PV cells made in a stretchable/flexible format in addition to the rest of the circuitry. In other embodiments, thin film batteries may be used to power the circuitry 1000S, which could enable an apparatus to be left in the body and communicate with the operator. Alternately, RF communication circuits on the apparatus may not only be used to facilitate wirelessly communication between devices within the circuitry and/or to external/separate systems, but they may also receive RF power to power the circuits. Using such approaches, the need for external electrical interfaces may be eliminated.

Circuitry 1000S includes therapeutic facility 1700, which in embodiments of the invention, includes various elements to effect a desired therapy. In embodiments, circuitry can comprise heat or light activated drug-delivery polymers that when activated could release chemical agents, such as anti-inflammatory drugs, to local sites in the body. Therefore, in embodiments, heat or light-emitting electronics (such as LED) could be utilized to activate a drug delivery polymer. In embodiments, therapeutic facility may activate light-activated drug release from polymers by using LED arrays to break down polymer linkages (de-polymerization reaction), and release stored drugs from polymer matrices. Further, therapeutic facility may employ mechano-electric modulation of polymers, gels and other applicable drug-loadable materials. In embodiments, electrical stimulus from electrodes in the therapeutic facility generates a modulation of pore size in materials, such as peptide based nano-fiber hydrogels having drugs incorporated therein. Physical changes then result, for example in the pore size, which causes the drug to be delivered into surrounding tissue.

In other embodiments, therapeutic facility 1700 may employ iontophoresis. Therapeutic facility of the invention may be embedded or integrated on or within semi-permeable substrate. The electronics of the therapeutic facility may comprise controllable electrodes (controlled in the manners described herein) that create an electric field. Electric field induces a force on charged or ionic fluids placed in or near the semi-permeable substrate. The strength of electric field may be altered to control flow rates across the semi-permeable substrate. In embodiments, varying pore sizes and/or the physical design of substrate may be used to further control the ionic fluid crossing the substrate. The fluids either contain drugs or caused the drugs to be controllably released once the fluid contacts them.

Such drug-delivery embodiments of the therapeutic facility may be passive (e.g. release of drugs by time based degradation of polymer matrices) or active (use of actuators to open reservoirs, light activation, mechano-electric reservoirs, iontophoresis, evaporation of metal foils to open reservoir). Exemplary drug delivery embodiments will be described below, but should not be considered limiting in nature.

Other therapies can be administered/effected by circuitry 1000S having therapeutic facility 1700 such as circuitry configured to deliver ablative therapy to cardiac tissue during deployment. Embodiments delivering ablation therapy may be termed an "ablative facility" or an "ablation facility." Other exemplary embodiments of therapeutic facility 1700 will be described herein. Those, exemplary configurations and methods for the therapeutic facility are not to be considered limiting of scope as such should not be considered as uniquely and exclusively applying to the particular exemplary embodiments being described but rather to all embodiments utilizing a therapeutic facility 1700.

In embodiments of the invention, circuitry 1000S comprises imaging circuitry 1600. Imaging circuitry 1600 in embodiments comprises a packed array of active pixel sensors. Each pixel in the array may contain a photodetector, a pn junction blocking diode, an active amplifier, and an analog to digital converter, formed in a single piece of single crystalline silicon (50×50 µm2; 1.2 µm thick). In embodiments, imaging circuitry 16000 may be encapsulated with a polymer layer such as PDMS to prevent contact stress induced damage. Imaging circuitry 1600 can comprise an array of photodetectors on the substrate 200 positioned in close proximity to the site of interest within the subject's body 2000 can provide high spatial resolution imaging without the need for a lens-based focusing due to the proximity of the photodetectors to the tissue. Imaging circuitry 1600 comprise a light source comprising or connected to an optical fiber or an LED to provide illumination to the photodetectors for imaging the tissue of interest.

Thus, the above configuration, designs, and techniques enables the circuitry to be in direct contact with and in some cases conform to the tissues in the body. Such conformal contact with tissues enhances the capabilities of the medical devices, methods, and systems disclosed herein.

Exemplary configurations for the circuitry 1000S including sensor 1100, processing 1200 and 1200A, output 300, and therapeutic facility 1700 methods, as well as fabrication techniques will be described below and referred to in the following discussion with reference 1000B, 1000N, 1000T, and 1000E. However, it should be understood that any embodiment of circuitry (and therefore its electronic devices, components, and other functional elements) described herein in shall apply to any of the exemplary embodiments. The exemplary configurations and techniques are not to be considered limiting of scope. It will be readily appreciated that the circuitry elements, configurations, and fabrication techniques of the present invention, as generally described herein, could be utilized, arranged or otherwise implemented in a wide variety of different ways. Also, and by way of clarification, the circuitry configurations and functional elements as well as the fabrication techniques described for and all exemplary embodiments described herein shall be considered to apply to each or any of the embodiments disclosed herein and as such should not be considered as uniquely and exclusively applying to the particular exemplary embodiments being described.

Embodiments of the imaging facility 1600 will now be discussed. It should be noted that the imaging facility 1600 may be incorporated into the circuitry or otherwise used in conjunction with any of the embodiments described herein. Such embodiments may involve a non-planar electronic imaging array composed of flexible and stretchable electronic components. The flexibility and stretchability of the array enables curved configurations. The stretchable electronic components are primarily in the form of active and/or passive pixel arrays which can be incorporated into the imaging systems detailed above. The electronic components may be arranged in islands (i.e., a device island arrangements), which house required circuitry and are interconnected mechanically and electronically via interconnects. The interconnects, in turn, preferentially absorb strain and thus channel destructive forces away from the device islands. They provide a mechanism by which the integrated circuits can stretch and flex when a force is applied. The present invention primarily references the device islands which consist of one or more pixel units for imaging purposes. However, stretchable electronic devices and device components which may be incorporated into an "island" are not limited to this description. The device islands and interconnects may be integrated into the structure of the end product or system level device by transfer printing. This is described further herein. Encapsulation of electronic devices and system/device interconnect integration may be performed at any of a number of stages in this process.

The circuitry used in the imaging array and accompanying electronic devices may comprise standard IC sensors, transducers, interconnects and computation/logic elements. These devices are typically made on a silicon-on-insulator (SOI) wafer in accordance with a circuit design implementing the desired functionality. Alternatively, the semiconductor devices may be processed on suitable carrier wafers which provide a top layer of ultrathin semiconductor supported by an easily removed layer (e.g. Polymethyl methacrylate, PMMA). These wafers are used to fabricate flex/stretch ICs by standard processes, with island and interconnect placement being tailored to the requirements of a particular application.

A representative, non-limiting example of fabrication steps utilized in creating an electronic device in accordance with the present invention is as follows. It will be appreciated by one skilled in the art that other stretchable electronics methods as described herein may be alternately applied in the creating a non-planar imaging device in accordance with the present invention.

In embodiments, electrical devices may be laid out in a device "island" arrangement. In, one embodiment of the invention, the device islands may typically be 1 µm×1 µm-1000 µm×1000 µm in area. However, other feature sizes may be utilized as required. These islands can accommodate at least one pixel which may include a photo sensing material and associated circuitry (e.g. transistors, in the case of active pixel arrays). Larger islands may have the capacity to hold more than one component or pixel. The islands may be connected to a buffer and/or an amplifier. Islands may accommodate active matrix switches, A/D converters, logic circuitry capable of reading in digital signals and processing them, and are capable of outputting data or storing data in memory cells. Additionally, some islands are simply designed and used as metal contact pads. At least one electrical and/or mechanical interconnection is found between each island.

Figures 7A, 7B:
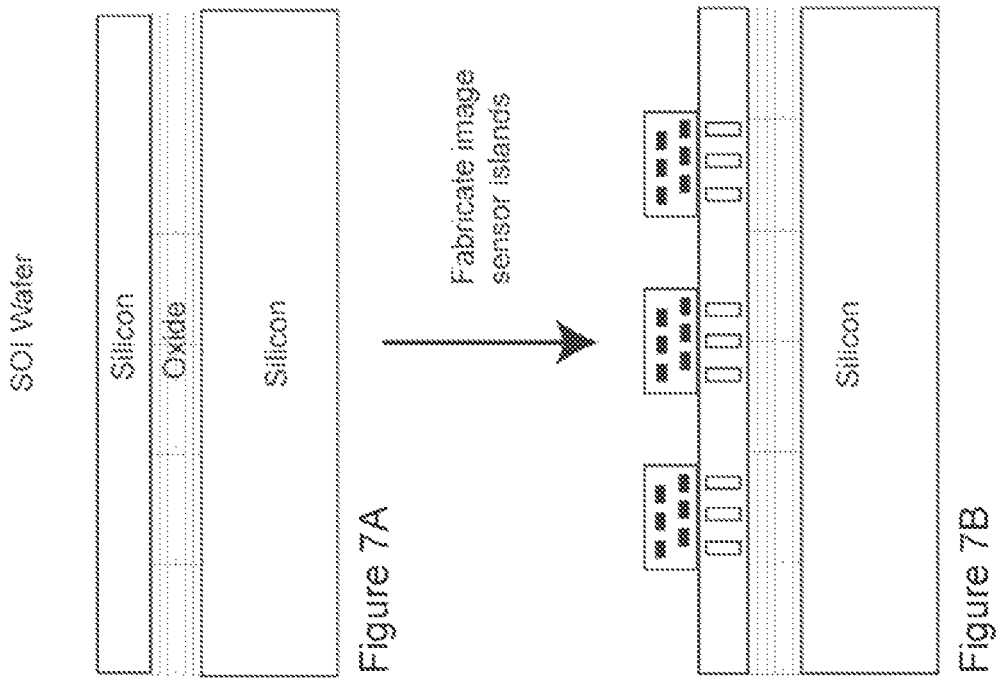

As shown in FIG. 7A, the image sensors may be fabricated on a planar SOI wafer (e.g. thickness from 100 nm to 100 µm thick; this example is a 1.2 µm thick top Si, 1 µm thick buried oxide) using standard CMOS fabrication technology. The image sensors may also be fabricated using non-silicon material such as germanium, gallium arsenide, indium phosphide, lead sulphide, and the like.

Figure 8:
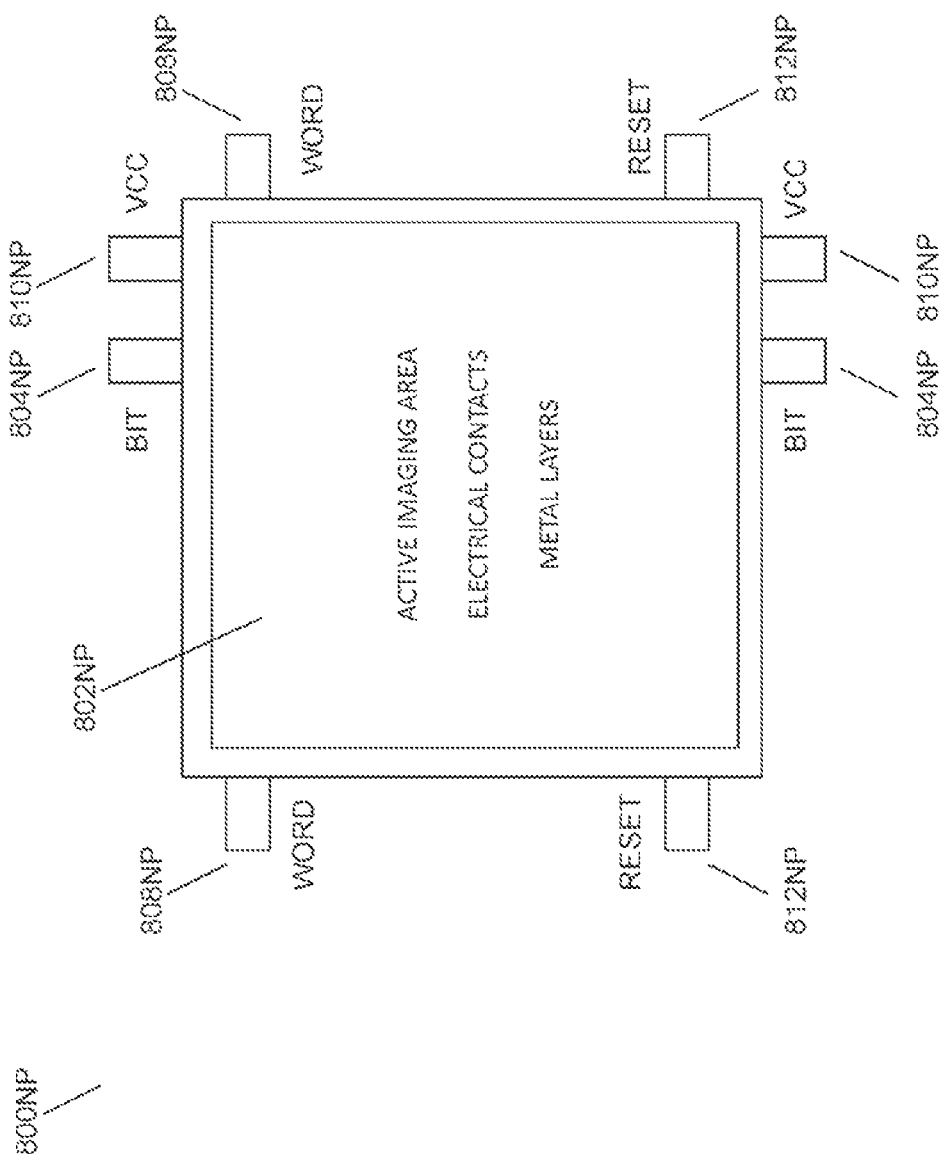
FIG. 8 is an illustration of a CMOS active pixel.
Figure 9:
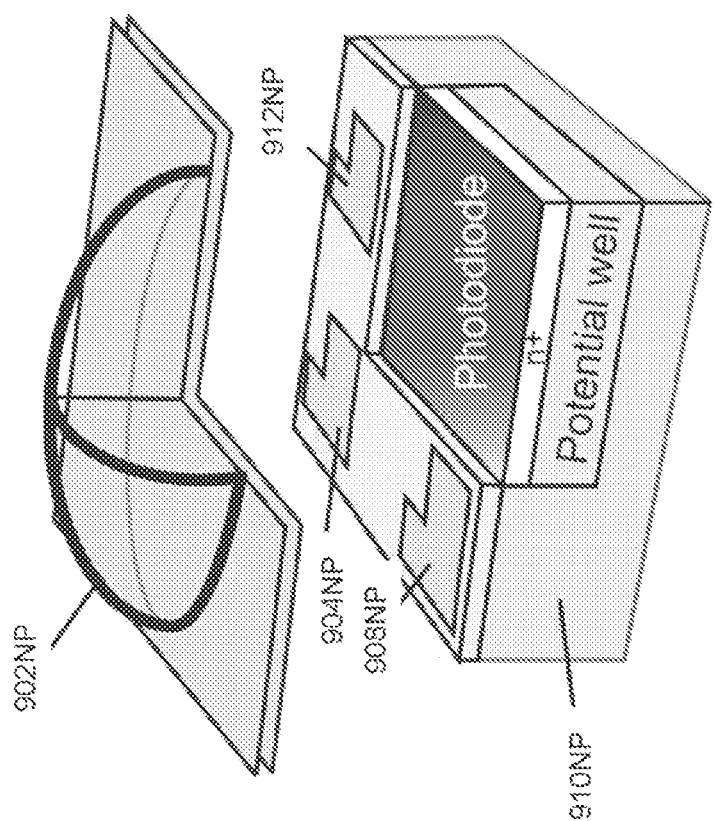
FIG. 9 is an illustration of a second CMOS active pixel.

As shown in FIG. 8, each pixel 800NP may be laid out in an array 802NP. As shown, the pixel may have control and power contacts, such as for bit 804NP and word 808NP selection, and power (Vcc) 810NP and reset 812NP. The array may be laid out such as in a 1 μm×1 μm island array, such as spaced apart by 1-100 μm from any adjacent island, and the like. After stretch processing, this inter island gap may be shrunk due to contraction of the entire array. Pixel dimensions may vary within the limits of island size (e.g. 1 μm×1 μm-1000 μm×1000 μm in area with an exemplary pixel pitch around 2 μm and thus an island of 100 μm2 will contain about 25 pixels). FIG. 9 shows an additional active pixel design that may be used, including a micro-lens 902NP, amplifier transistor 904NP, bus transistor 908NP, silicon substrate 910NP, reset transistor 912NP, and the like.

Figure 7C:
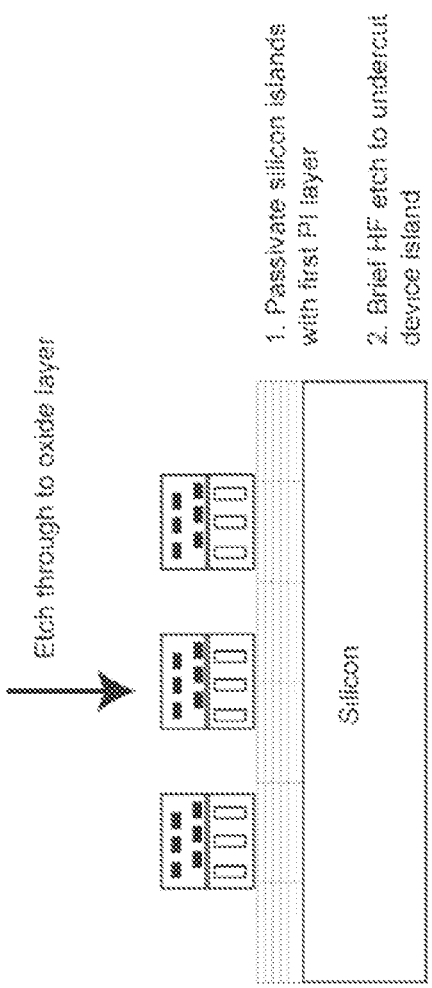

One embodiment of the imaging array is a CMOS active pixel array made using a 2 metal layer process. The array is designed using rules specified for the integration of mechanical bridges and electrical interconnects into the system. Image sensor grids are fabricated on an SOI wafer separated by gaps (FIG. 7B). These gaps facilitate the formation of stretchable interconnects at a later stage. The silicon under each gap is then etched away to isolate image sensor islands (FIG. 7C). This space may be important when considering the final non-planar shape of the imaging array. In order for the pixels to be evenly spaced in the final non-planar shape, the pixels/island separation may need to be unequal in the planar layout. Hence, the interconnect between islands may be of different lengths. Calculations are done on a case-by-case basis to determine the optimal layout of islands in the planar design in order to achieve uniform density of pixels in the non-planar imaging array. For instance, the spaces between image sensors may range from 100 nm to 100 μm.

Figure 7D:
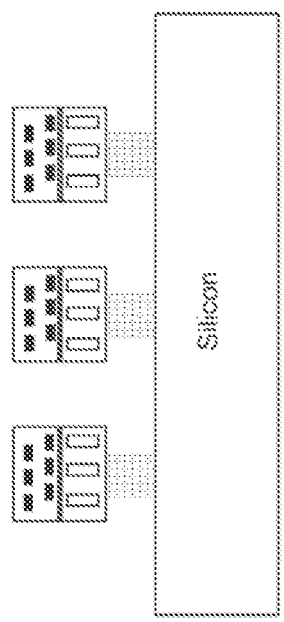
Figures 7E, 7F:
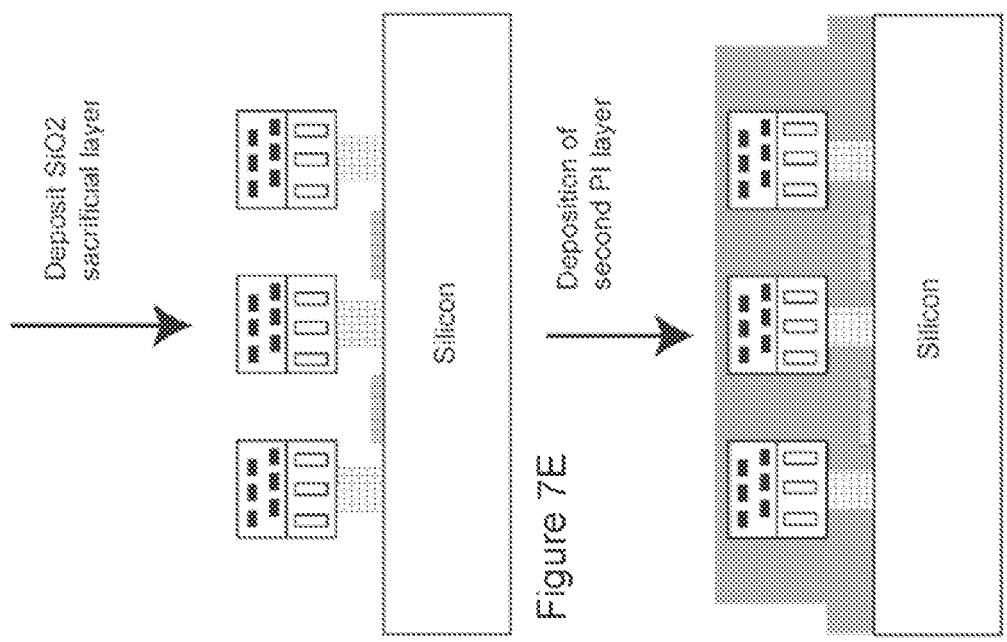

In an example, the image sensor islands are protected by a first polyimide (PI) passivation layer, then a short HF etch step is applied to partially undercut the islands (FIG. 7D). The first passivation layer is removed, and then a thin film of SiO2 (100 nm thick) may be deposited and patterned by PECVD or other deposition technique combined with a lift-off procedure, such that the oxide layer covers most of the space between device islands except for a region that is about 5 μm wide (FIG. 7E). The purpose of this oxide layer is to act as a sacrificial layer during the final etch step so that the PI that is deposited in the next step only adheres to the underlying silicon in a small ~5 m wide region that has sufficient adhesive force to prevent the devices from floating away in the HF etch but not too much adhesive force to prevent high yield transfer printing.

A second polyimide layer is spun on and patterned to form the shape of the interconnect wires/bridges between the islands (FIG. 7F). Typically one bridge may extend from the center of one island edge to the center of another island edge. This design was used in a passive matrix imaging array. Alternately, two bridges may extend from each corner of the device island to two different device island corners. Other bridge configurations may also be utilized especially for designs which aim to reduce the overall mechanical strain in the final stretchable system (determined by mechanical modeling). One exemplary interconnect design has a tightly packed serpentine layout and connects from one corner of an island to the corner of an adjacent island. In embodiments, interconnect bridges may be about 100 nm to 500 μm wide and may accommodate multiple electrical lines.

Figure 10:
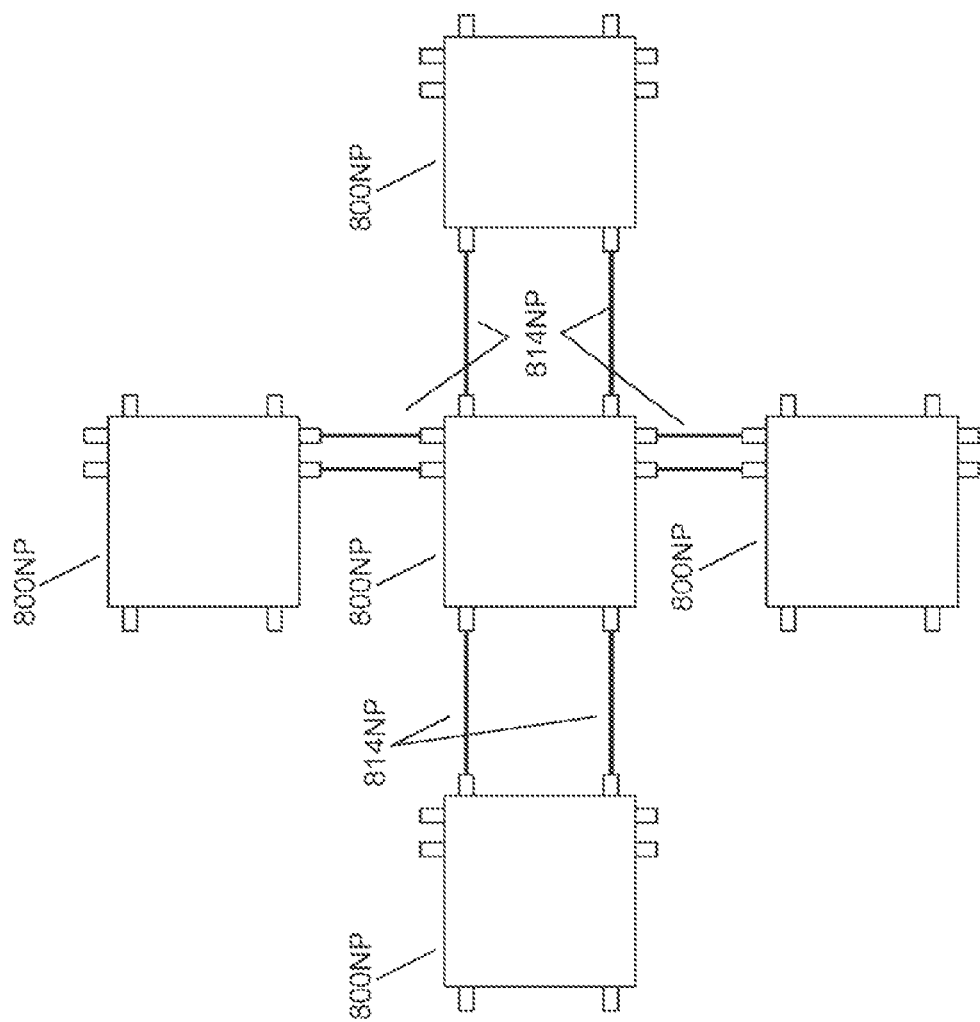
FIG. 10 is an illustration of an interconnected pixel array with one pixel per island.
Figure 11:
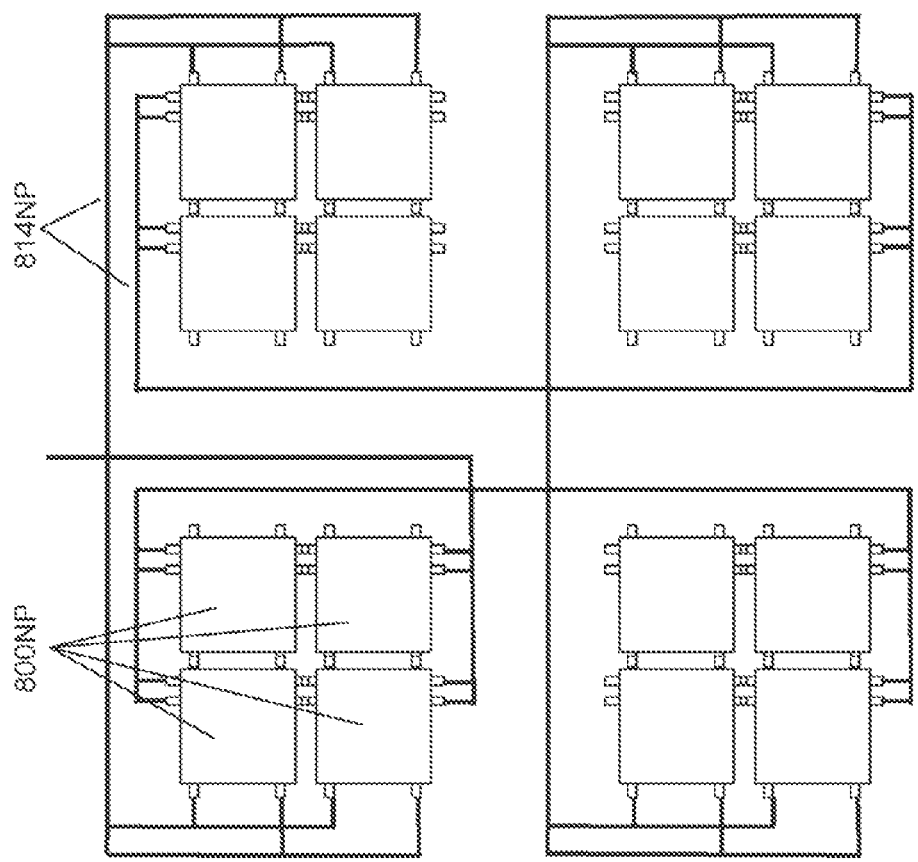
FIG. 11 is an illustration of one example of an interconnected pixel array with 4 pixels per island.
Figure 12:
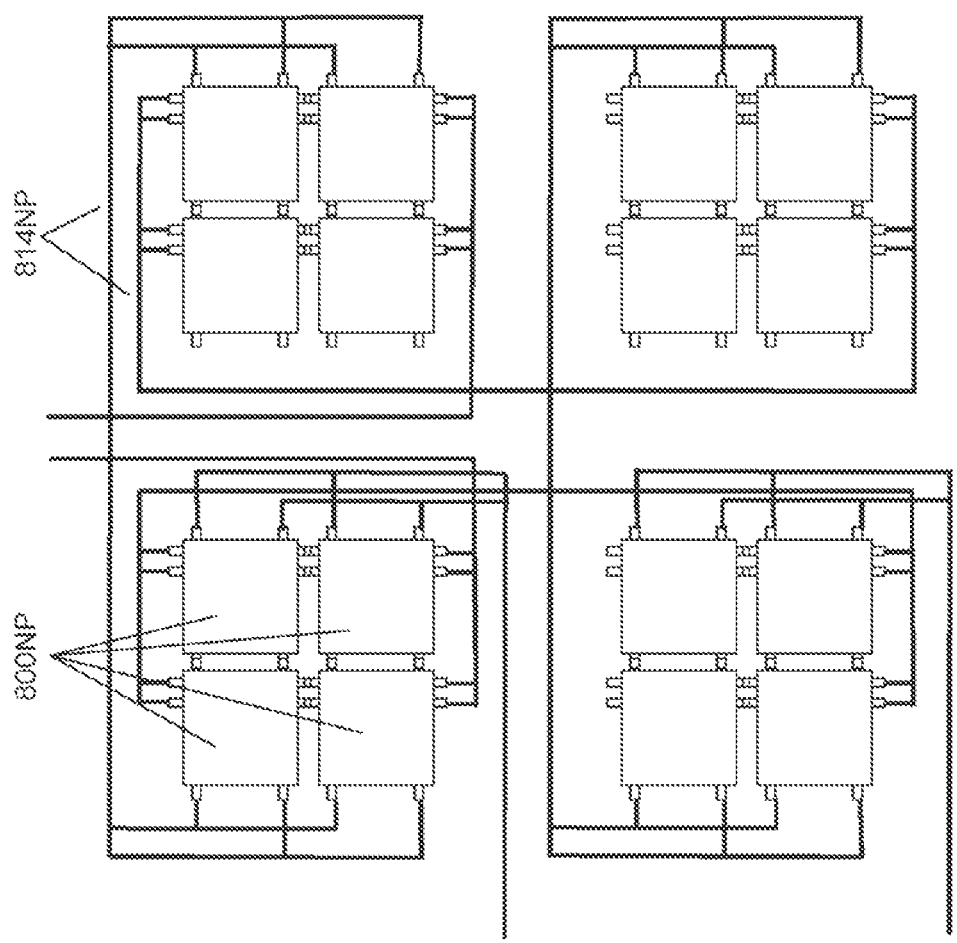
FIG. 12 is an illustration of another example of an interconnected pixel array with 4 pixels per island.
Figure 13:
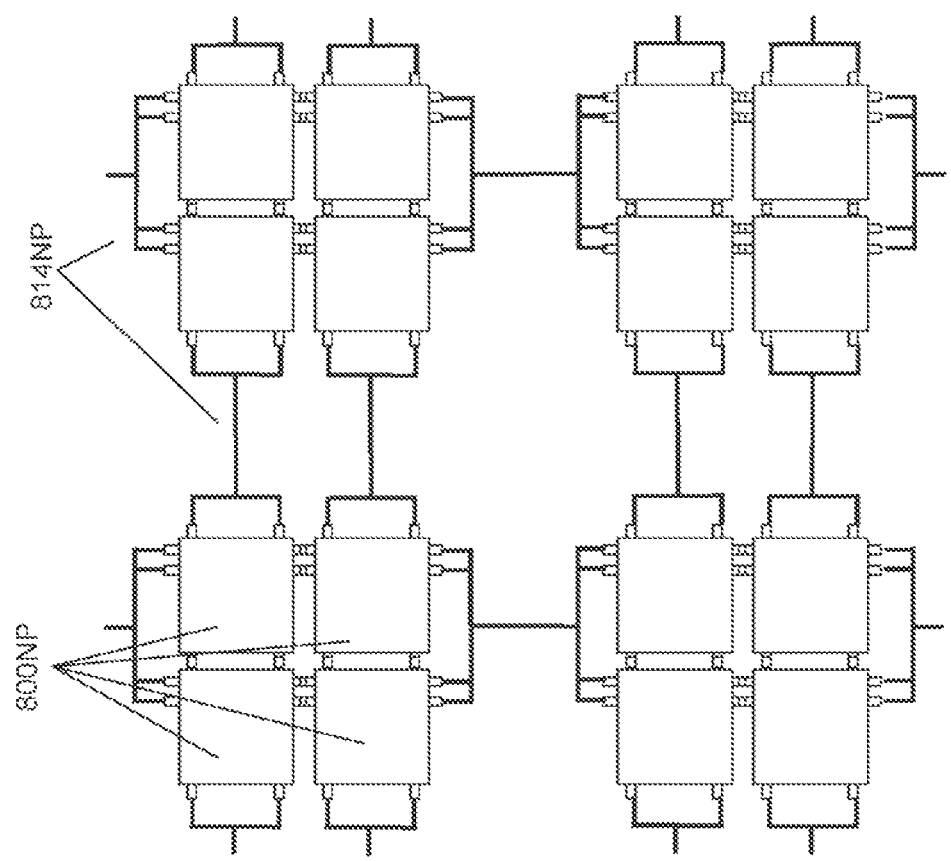
FIG. 13 is an illustration of another example of an interconnected pixel array with 4 pixels per island.

The second polyimide layer partially fills where the device island is undercut; this serves to stabilize the island later in the release process and to prevent its migration. Vias are etched into the second PI layer to make metal interconnects. Next, a third metal layer is patterned to contact the circuits and connect word, bit, reset and vcc lines from one island to another (FIG. 7G). In one embodiment of the invention, the islands are made up of one pixel each. In this example the third metal layer contacts points 1-8 through vias as show in the FIG. 10. Vias are made down to the first and/or second metal layers as required, facilitating electrical contact between the sensor's word, bit, reset and Vcc lines and the third metal layer. In another embodiment of the invention, the islands are comprised of multiple pixels. FIGS. 11-13 illustrate a number of designs which may be useful for interconnecting islands with multiple pixels.

In one embodiment of the image sensor, a color filter array (e.g. Bayer Color filter array) is then deposited onto each pixel (FIG. 7H). This is accomplished by using a pigment infused photoresist (e.g. diazonaphthoquinone DNQ-Novolac) as done in conventional color filter deposition. For applications that do not require color images, this step may be omitted.

Figures 7I, 7J:
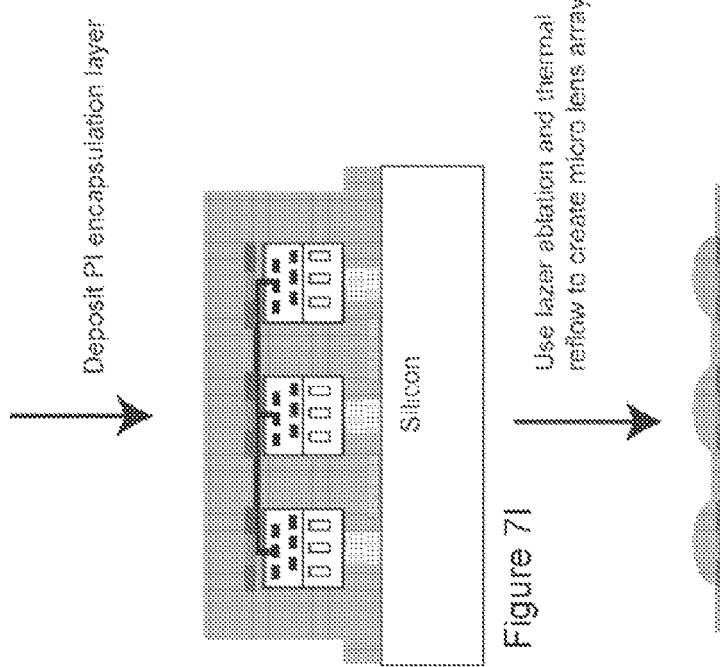

A third PI layer may be spun on (covering the wires and everything else) (FIG. 7I). In one embodiment of the invention, the third PI layer may then be processed using laser ablation and thermal reflow to create an array of micro-lenses as shown in (FIG. 7J).

The second and third PI layers are then isolated by etching with a deposited SiO2 hard mask, in O2 RIE. PI located outside device islands and bridges is etched, as well as PI covering areas that are meant to be externally electrically interfaced, and small areas leading to the underlying oxide.

Figure 7K:
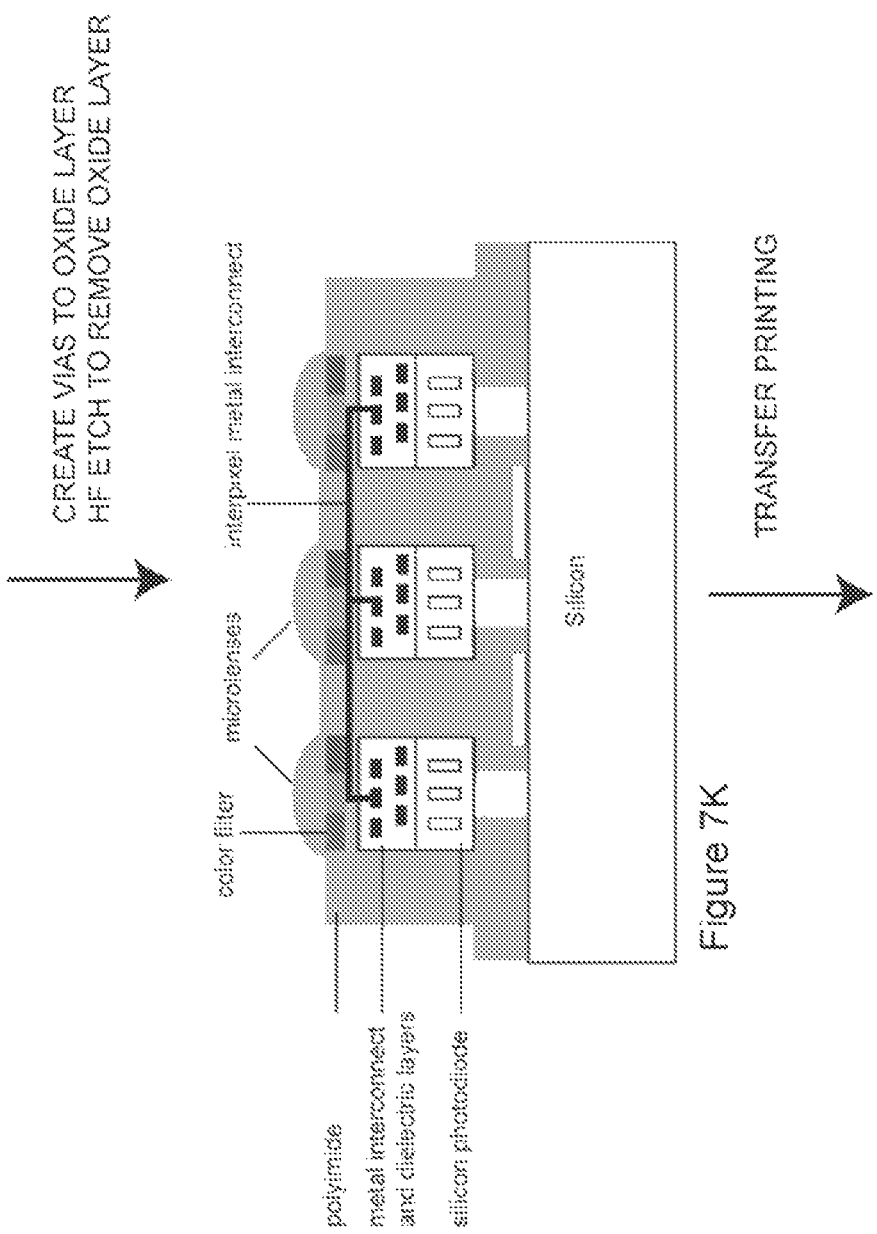

Etch holes may be formed if necessary and then transferred through the silicon or metal layers by wet and or dry etching. The underlying buried oxide is etched away using HF etchant to free the devices, which remain attached to the handle substrate due to the second polyimide passivation layer which contacts the handle wafer near the border around the device islands (FIG. 7K).

If the HF etch is not controllable enough and seeps under the PI isolation layer and thereby attacks the CMOS devices, then prior to the second PI passivation a brief Argon sputtering can be done to remove any native oxide followed by amorphous silicon sputtering followed by the PI passivation and rest of the processing. After rinsing, the devices are left to air dry. The end result is a network of islands connected by metal and polymer interconnect system. These islands contain one or more pixels.

It is understood that stretchable circuits may be realized using techniques other than those described above, combinations of the techniques listed above, and minor deviations from the techniques described above. For example, stretchable circuits may be formed on plastic, elastomeric, or other stretchable materials by sputtering, chemical vapor deposition, ink jet printing, or organic material deposition combined with patterning techniques. Semiconductor materials which may be used to make circuits may include amorphous silicon, polycrystalline silicon, single-crystal silicon, conductive oxides, carbon nanotubes and organic materials. All of the methods described above for enabling stretchable circuits may be referred to herein as "stretchable processing."

Under-etched, ultrathin partially or fully processed circuits fabricated by one of the methods described above may be transferred from their silicon mother wafers to a desired surface via transfer printing, as described herein.

Figure 14:
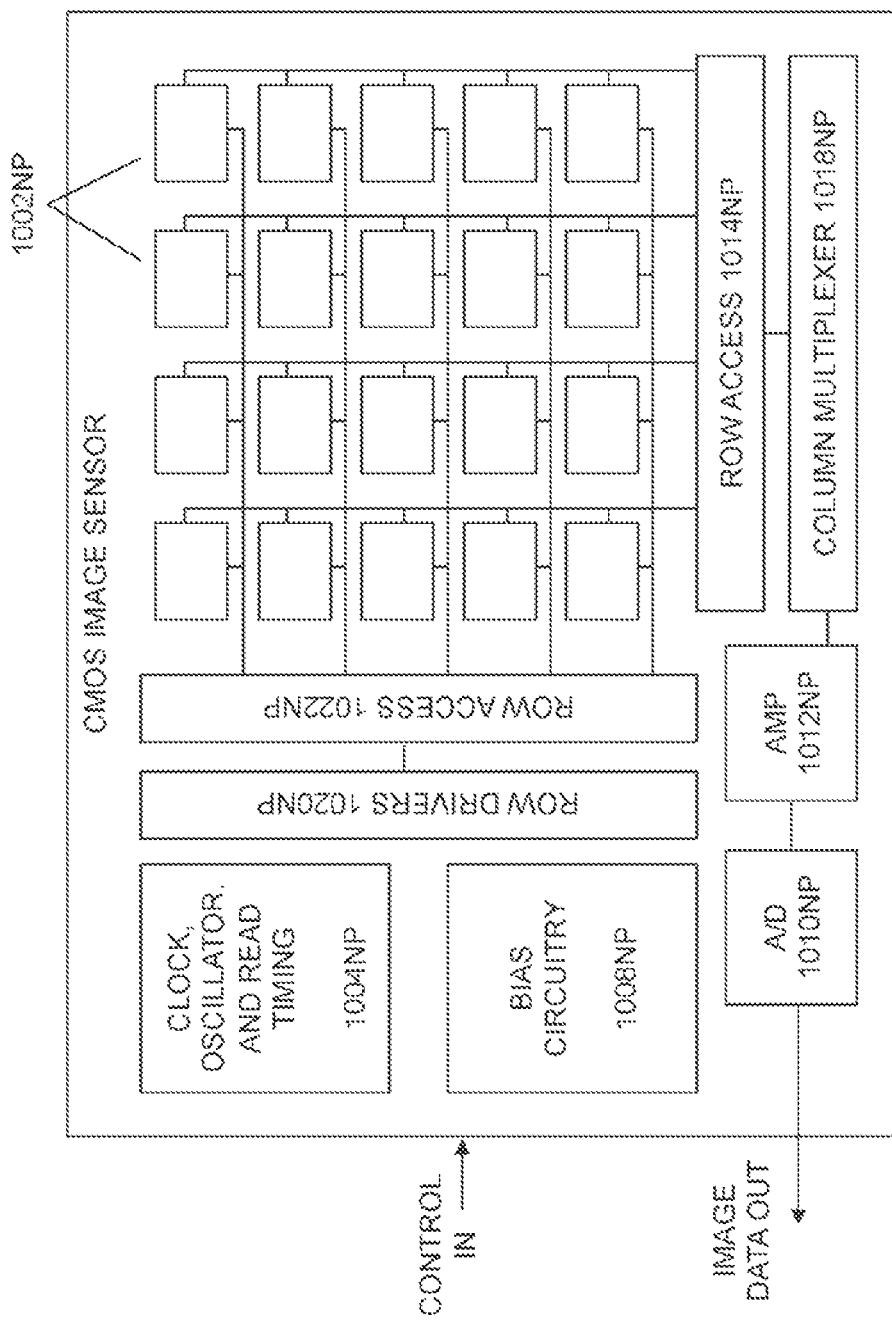
FIG. 14 is an illustration of the typical architecture of a CMOS imager.

One embodiment of the non-planar imaging array comprises a CMOS imaging system. This imaging system may be either active or passive. The components of the CMOS imaging system follows conventional CMOS imaging technology, as known to the art, where the CMOS sensor device converts an image into a digital image. The sensor usually includes a pixel array with transistors and several sensing elements, such as photodiodes. The CMOS image sensor is composed of a photo-sensing means for sensing light and a CMOS logic circuit for processing sensed light into electrical signals to make them as data, where a readout circuit is connected to each pixel cell. One method in which to create an active matrix imaging array is done by joining islands with pixel units similar to those shown in FIGS. 8 and 9. FIG. 10 illustrates how one CMOS active pixel may be connected to a series of neighboring pixels to form an array joined by interconnects which will ultimately enable stretchability and the ability of the array to conform to non-planar configurations. FIGS. 11A-C illustrates the example where there are multiple pixel units on an island connected via metal lines sandwiched between a polymer support such as polyimide. In color camera applications, color filters are required since sensors only measure light intensity. Micro-lenses are also used to increase the amount of light focused onto each pixel. These layers can be easily incorporated into the non planar pixel array by well known techniques. Ultimately the CMOS imaging array is incorporated into a larger system such as a camera module and would require supporting hardware to create useful information; such as illustrated in FIG. 14, including, image pixels 1002NP, timing 1004NP, bias circuitry 1008NP, A/D converter 1010NP, amplifier 1012NP, column multiplexer 1018NP, row access 1014NP, and the like.

Another embodiment of the CMOS array is the backside illumination configuration. This configuration incorporates aspects of the original design but instead of having light from the image come through the metal layers, the array is flipped and light is channeled onto each pixel from behind (closer to the sensing element). This design significantly increases the amount of light that reaches a photodiode because less light is blocked by metal interconnects and dielectric layers (pixel vignetting) as occurs in conventional front side illuminated imagers as shown in FIG. 15A. This back side illuminated configuration stack design can be seen in FIG. 15B. Similar to the conventional top illuminated image sensor, the backside illuminated pixel requires a color filter in order to produce color images and benefits from having a microlens array on top of the stack to guide more light into the photosensitive parts of the imager.

Manufacturing these inverted detectors uncovers significant challenges with photodiode/lens/color filter alignment, pad contact forming and wafer thinning which are all required processes. The stretchable processing technique described in this invention provides a method by which some of these challenges may be overcome. It is particularly effective as an alternative to conventional wafer thinning processes which suffer from a significant reduction in sensor yield with reducing thickness. The current invention describes a method which employs undercut etching and polymer encapsulation to create thin devices and avoid the need for backside grinding of devices.

Figure 17A:
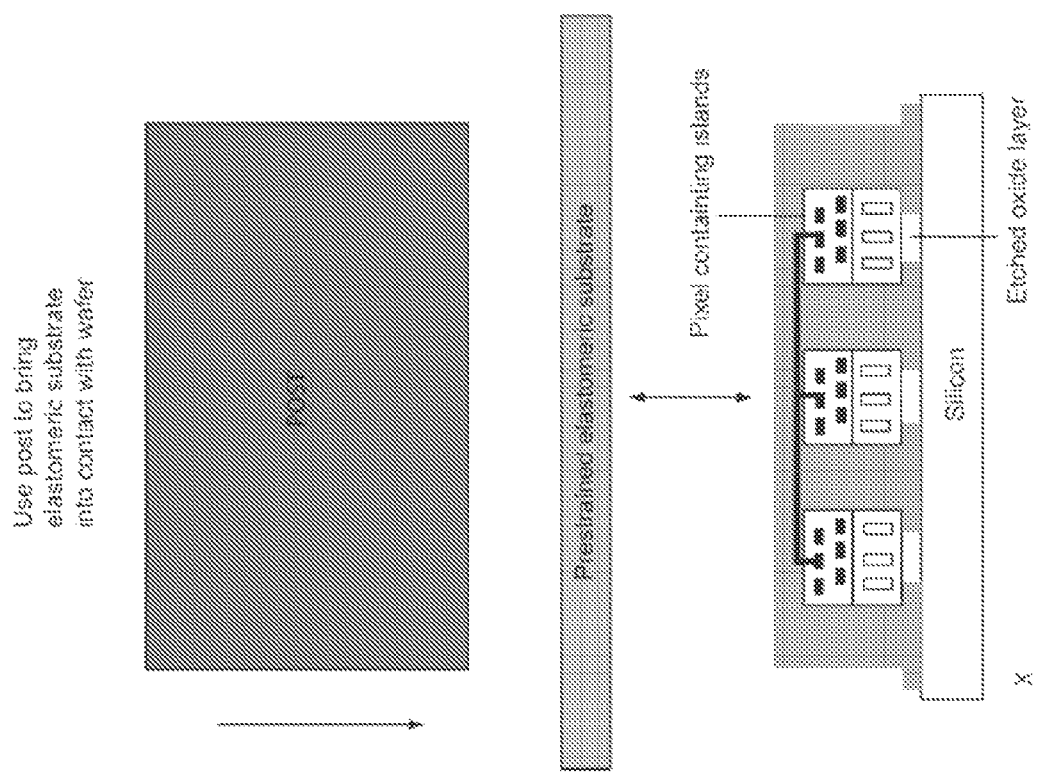
FIGS. 17A and 17B outlines steps in a method for fabricating curved backside illuminated imagers from stretch processed image sensors.
Figure 17B:
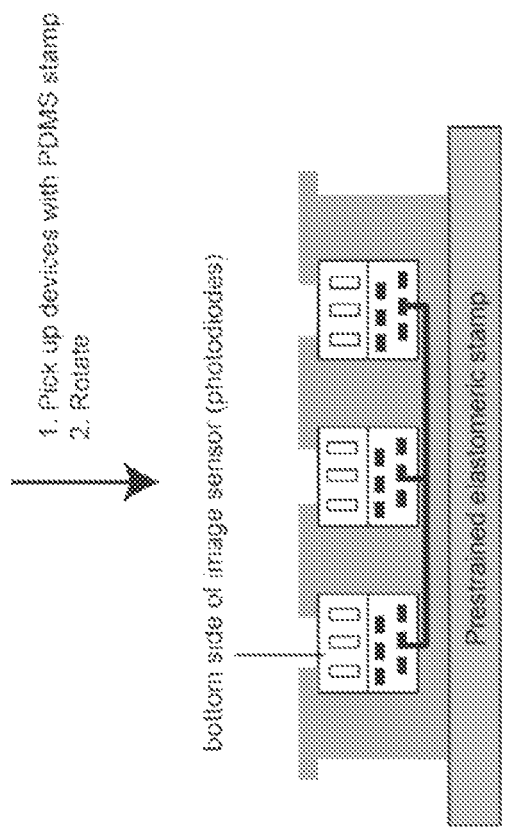
Figure 18C:
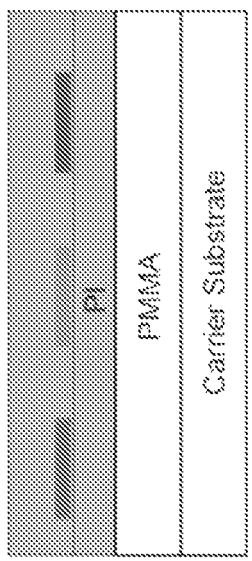
Figure 18D:
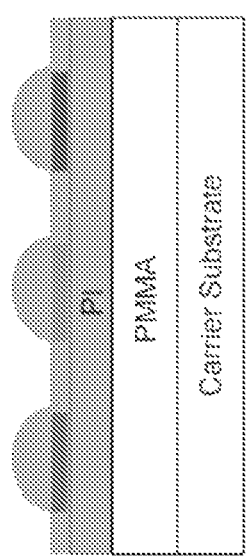
Figure 19:
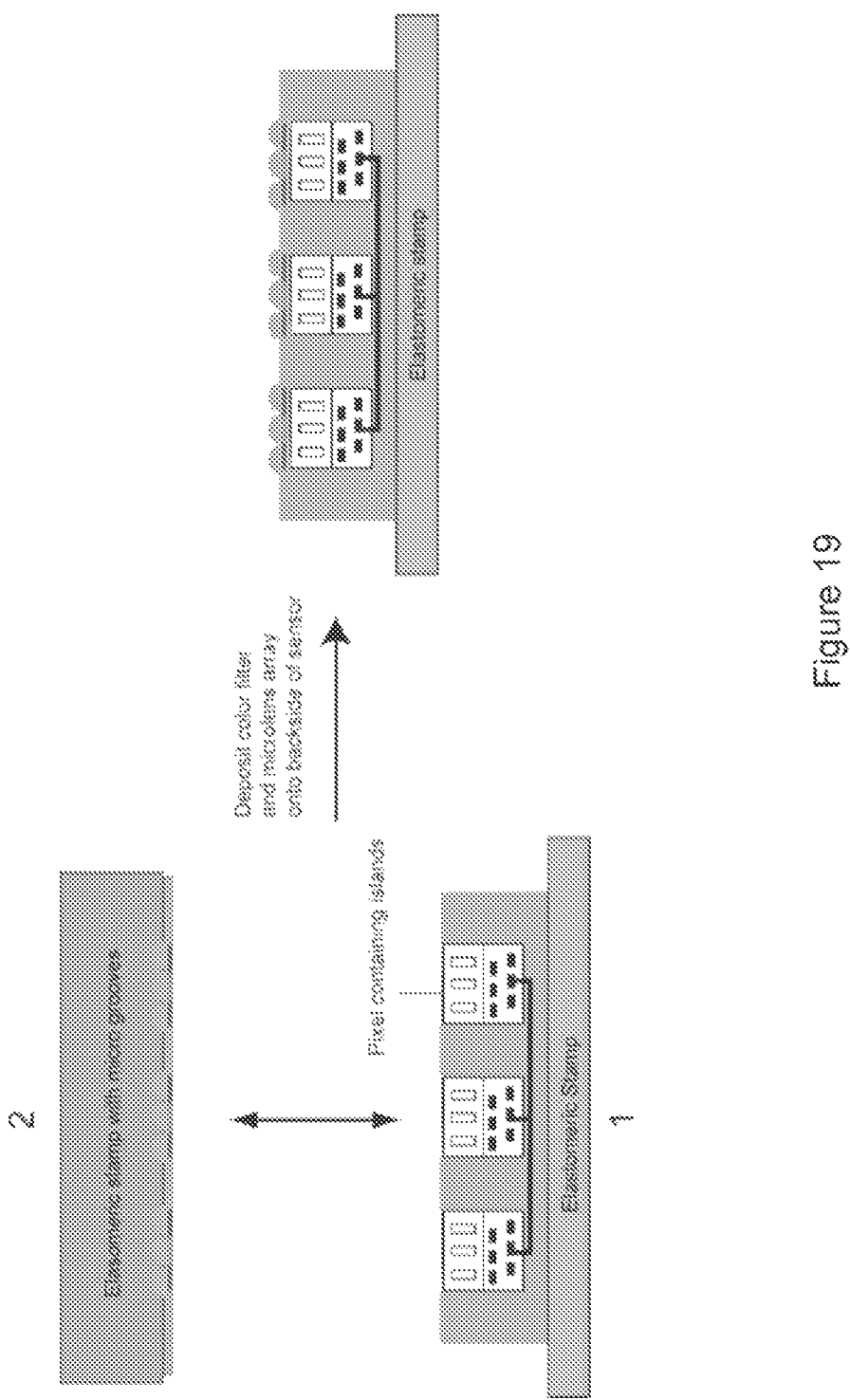
FIG. 19 outlines steps in a method for fabricating curved backside illuminated imagers from stretch processed image sensors an incorporating it into a BGA package.

In order to create a backside illuminated imaging array, the same process may be followed for the front side illuminated array (conventional) up to the point of deposition of the inter-pixel metal interconnects as illustrated in FIG. 7G. After the deposition of the final metal layer, vias are drilled to the oxide layer and the image sensor islands are undercut. This undercut releases the islands from the mother wafer but they are supported by the PI posts that lie beneath them. The stretch processed image sensor is then flipped over using a geometric transfer stamp as shown in FIGS. 17A-B. The color filter array and a microlens array can be fabricated via conventional techniques while stacked on top of a sacrificial layer as illustrated in FIGS. 18A-F. The color filter and microlens array are aligned with the sensor array and the both are bonded together to complete the device construction as illustrated in FIG. 19.

Figure 20A:
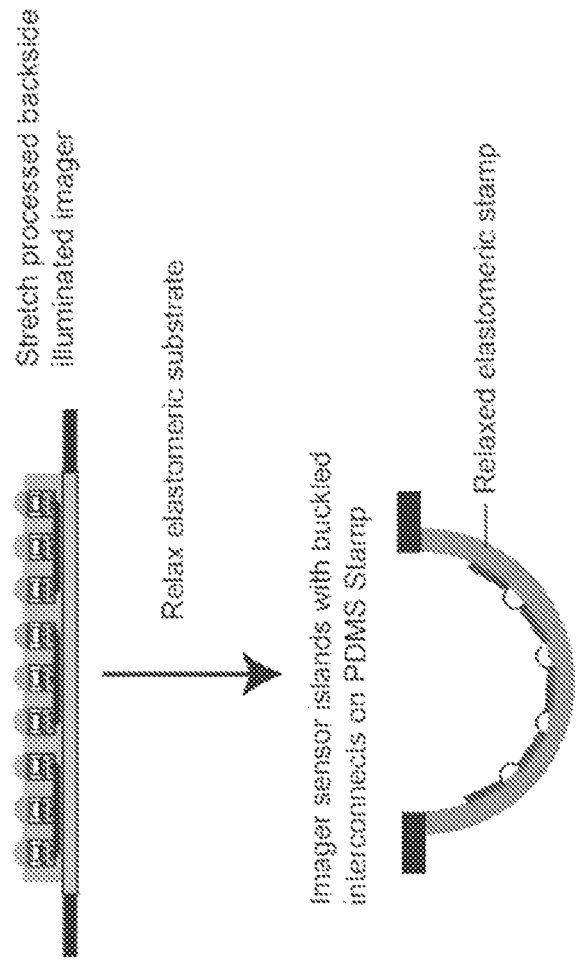
FIGS. 20A-20C outlines a method for incorporating curved backside illuminated imagers fabricated from stretch processed image sensors it into a BGA package.
Figure 20B:
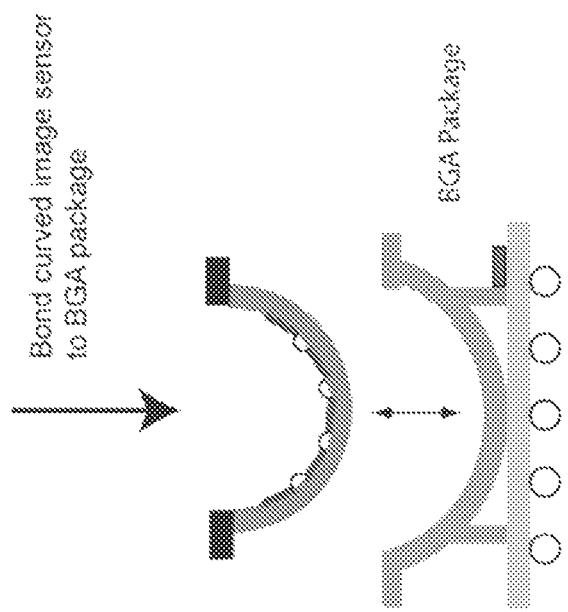
Figure 20C:
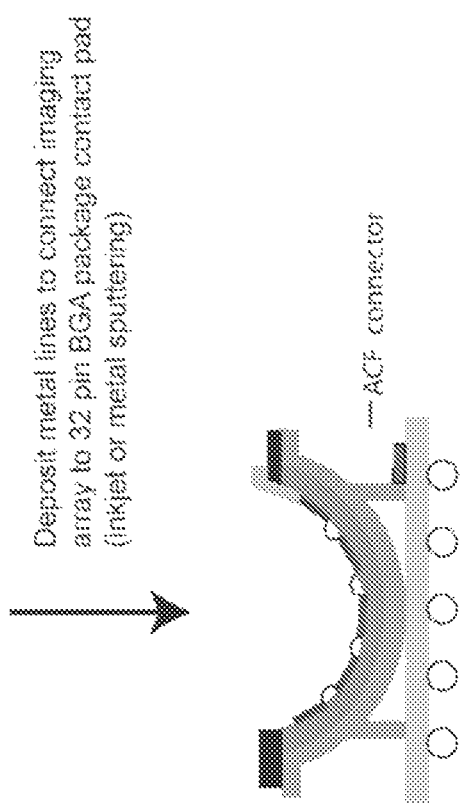
Figure 22E:
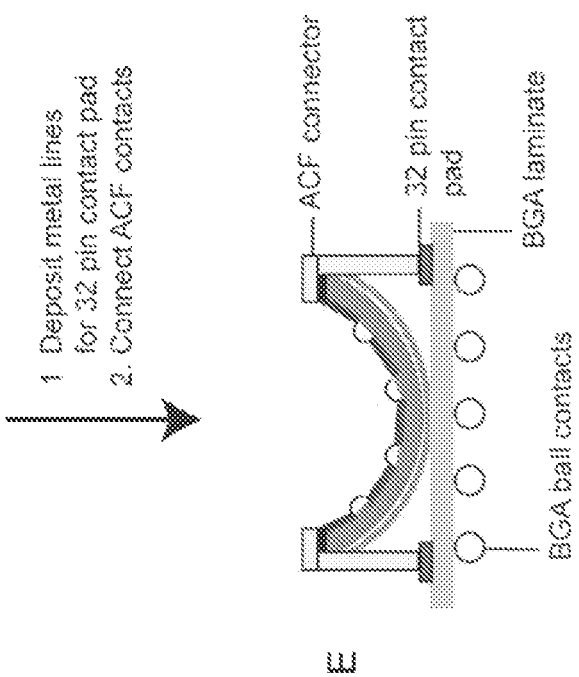

The next step involves relaxation of the geometric stamp to form the required curved shape. The curved sensor is then packaged as illustrated in FIGS. 20A-C. Other potential process flows for creating a backside illuminated imager are illustrated in FIGS. 21-23.

In embodiments, the present invention may provide for a method for fabricating a planar back-side illuminated imager. As shown in FIGS. 24A-F, the process for creating a backside illuminated imager begins with creating photodiodes on top of a sacrificial layer, supported by a rigid carrier substrate. In this example, silicon photodiodes are fabricated on an SOI wafer. Dielectric and metal lines are then fabricated on top of the photodiodes to complete fabrication of the image sensor. Conventional image sensor designs may be exploited for the previous mentioned steps. A polymeric material is then used to passivate the surface of the image sensor. This polymeric material offers mechanical support. An etch step follows, creating small holes to access the sacrificial layer (e.g. SOI oxide layer). The sacrificial layer is then removed by chemical action. The image sensor array is now ready to be flipped, preferably using an elastomeric stamp. The stamp picks up the image sensor form its carrier substrate and transfers it to another stamp which completes the flip. It is subsequently deposited onto a clean second carrier substrate for further processing. At this stage, color filters and micro-lenses may be fabricated using techniques known to those familiar in the art.

The methods described herein to attain non-planar imaging arrays may be applied to numerous other imaging array/pixel designs. Commercially available CMOS imaging array designs may be modified using our stretchable processing method to give non-planar imaging array formats, such as megapixel imagers, full frame imagers, line imagers, CMOS imagers, CCD imagers, and the like. The modification involves connection of islands, each containing at least one imaging pixel, with a series of metal and polymer interconnects as described above. Connections may be made through vias which provide a means of accessing buried metal layers and joining them to an inter-pixel interconnect network which allows deformation of system.

In accordance with embodiments of the present invention, the non-planar imaging systems may be incorporated into a number of products/applications such as medical imagers, endoscopes, blood-flow imagers, nuclear medicine imagers, infra-red cameras and other imagers, active pixel arrays for high definition imaging, x-ray imagers, gamma ray imagers, ultrasound imaging, thermal imaging, and the like. The embodiment of the image sensor in each application may be either in the form of a packaged image sensor, a camera module (optics component and imager) or a more complete camera (self sufficient imaging device with all software and hardware required for application specific performance).

The image sensor may be incorporated by various methods. One method involves direct incorporation of the imaging array into the camera of the desired system, thereby replacing the planar imaging array with a non-planar imaging array as described in above embodiments. This is done by depositing metal lines to connect the image sensor's bond pads to the outer rim of its supporting substrate, then bonding an anisotropic conductive film (ACF) connector from these metal lines to the receiving systems' computing modules. There may be at least one ACF connector leaving the imaging array that may be connected to a circuit for image processing. Conductive pads in the imaging array's layout are conveniently placed in easily accessible regions close to the perimeter of the array. If the pads are covered by an encapsulation layer such as PDMS they may be accessed via wet or dry chemical etching, mechanical removal of material, including but not limited to drilling, or by laser/heat ablation.

Another method for incorporating the curved sensor array into a product is to package the image sensor in a more conventional chip scale package such as ball grid array (BGA) as shown in FIGS. 16A-F and 20A-C. In accordance with the above embodiment, metal lines are created to contact the image sensor's bond pads to the outer rim of its supporting substrate. Subsequently, ACF connectors are fused to these metal lines and connected to a 32 pin contact that is linked to the BGA laminate for communication with external components. The BGA substrate typically consists of two or more insulated metal layers (copper covered bismaleimide triazine (BT) laminate). The laminate is bonded to a series of copper balls on its underside. Vias are drilled into the substrate through to the copper balls to facilitate a direct path the 32 pin contact pad and conductive balls. In order to stabilize and secure the underside of the curved image array and its ACF interconnects, a protective epoxy may be applied. The BGA form of the curved imager will be more readily acceptable into a multitude of products and may open the possibility of addressing systems not designed specifically for the uniquely shaped imagers. Other types of BGAs may be used, such as well understood by one skilled in the art.

Figure 25A:
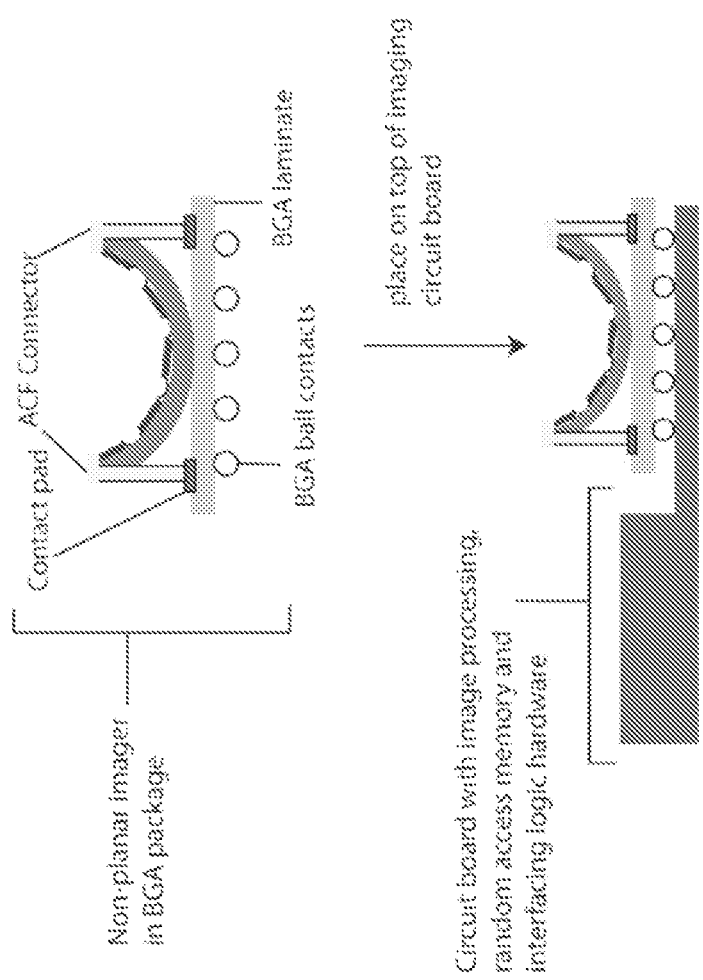
FIGS. 25A-B illustrates a method for creating a camera module using a curved imaging array.
Figure 25B:
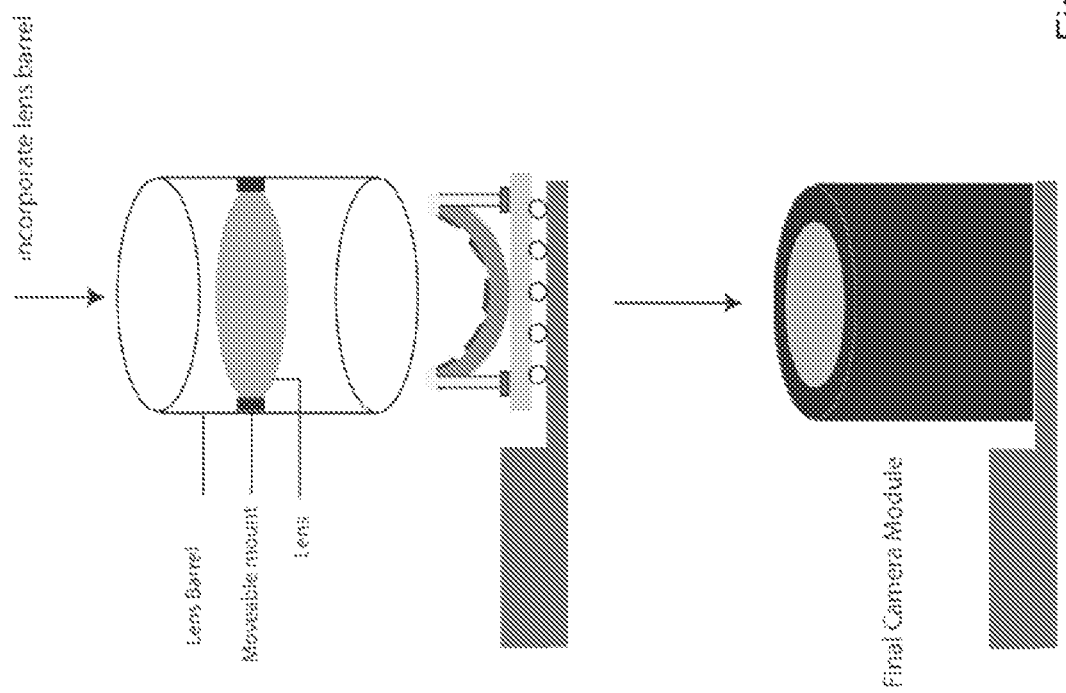

In accordance with the embodiment of the invention referring to a non-planar image sensor incorporated into a camera module as shown in FIGS. 25A-B. The packaged image sensor (e.g. BGA) is directly integrated into a circuit board which houses components including an image processing device, random access memory and interfacing logic hardware. This is done by aligning the ball contacts at the bottom of the BGA with the contacts of the circuit board then applying heat for the balls to melt and make permanent bonds.

Finally, a lens barrel containing at least one lens, is aligned with the image sensor. The lens barrel contains adjustable mounts which can change the distance between the lens(es) and the imaging array to change focus. The three components may be produced separately then assembled. The lens barrel has at least one lens on a moveable mount. This lens may be either glass or plastic. The lens is designed to be easily snapped into the moveable mount during assembly. In one embodiment the lens and its plastic holder may be extruded together.

One embodiment of the camera module has at least one injection molded plastic optic/lens which can be readily made to various curvatures and sizes before insertion into the lens barrel. A metal mold is fabricated with a hollow lens-shaped cavity that is filled by injecting polymer in a semi-liquid form. The polymer is allowed to set or cure before opening the mold and removing the part. This process is done under high pressure and the polymer lens requires little finishing work before it is set into place on the moveable mount of the lens barrel. Yet another embodiment of the camera module has a lens that can change its curvature. This is achieved by using an encapsulated liquid or gel based lens which can be put under different radial tensions, thereby changing the curvature of the lens. Changing the curvature of the lens in this manner gives a greater focusing capability to the camera module. The radial tension may be administered via the moveable mounts upon which the lens is supported.

Another embodiment of the invention relates to a non-planar imaging array that can be bent dynamically while attached to the rest of the camera module. This is achieved by encapsulating the image sensor with a thick (~1 mm) and flexible PDMS substrate. The PDMS layer enables deflections of the imager with little or no effect on the imager performance. The main purpose of such an imager is to morph for different optics heads just as a lens system is adjusted to tune the focus and magnification of an image. The varying of curvature may be performed by an actuator similar to that of the moveable mount in modulating lens curvature in the embodiment discussed above. The application of tension in the imager changes its shape and thus changes the focus of the camera module. Application of equal radial tension may be achieved using a mechanical jig which clamps onto the outer rim of the imaging array and can be expanded or contracted equally in all directions to change the curvature of the array without losing symmetry. The substrate which supports the imaging array will also have to be stretchable in such embodiments.

There is a need to optimize the curvature of the imaging array to meet application specific requirements (e.g. different degrees of imager curvature). Standard configurations for the shape of these non-planar arrays include hemispherical, ellipsoid and paraboloids of revolution. However, the arrays may be fabricated into wider variety of symmetrical and non-symmetrical shapes as long as the system strain does not exceed its maximum capacity which was demonstrated to exceed 150%. There may also be a need to optimize the shape and number of lenses in each system. Finally, minor spatial redesign may be required when changing number or lenses and shape of imager. This modification can be considered minor and most likely would not require a significant amount of innovation.

In embodiments, the present invention may provide for improved methods for fabricating a non-planar imaging array. The advantages of a non-planar, or curved imaging arrays is well understood in the art, including a lower number of optical elements (and thus a reduction in weight, size, cost, complexity), reduced aberrations including astigmatism and coma, an increase in off-axis brightness and sharpness, an increased field of view, and the like. The present invention provides a method by which a non-planar imaging array may be fabricated utilizing image sensors made with standard semiconductor processes as described herein, such as for example, CMOS imaging elements or CCD imaging elements made from single-crystalline semiconductor. The present invention then fabricates and integrates the image sensors into a non-planar image array from stretchable electronics technologies, as described herein, allowing for the creation of an optical system that benefits from both standard high quality semiconductor processing of the image sensor, and from the advantages of non-planar imaging arrays as realized through utilization of stretchable electronics technologies. These benefits may be realized in a plurality of optical systems, such as listed herein, especially where reduced weight and size, and increased field-of-view are important, such as for example, medical vision systems such as endoscopy, and the like.

In embodiments, a medical vision system may be implemented, such as for example in any of the embodiment described herein including those with reference to endoscopy described below in connection with FIGS. 50 to 53 and as disclosed in co-pending U.S. Nonprovisional patent application Ser. No. 12/686,076 entitled "Methods and Applications of Non-planar Imaging Arrays" filed Jan. 12, 2010, the entirety of which is incorporated herein by reference.

Referring to an endoscopic imager as described herein, it can be seen that a non-planar imager mounted on an endoscope or imaging endoscopic capsule, can be implemented with the present invention. Here, the non-planar imager may be presented on the surface of the endoscope or endoscopic capsule, such as in a concave or convex configuration. A technician reading the images sent back from a procedure utilizing one of these devices may now have all the benefits provided by the present invention, including increased field of view (due in part to the curved image surface), increased image quality (due in part to the benefits of non-planar imaging and from high quality image sensors), increased performance in dim light conditions (due in part to the high quality image sensors), and the like. The non-planar imager of the present invention may enable the image array to be formed on a plurality of medical device surfaces, and still maintain a high quality image product, such as being mounted on different probes, catheters, implants, and the like. In embodiments, the present invention may provide an improvement to both the image quality and field-of-view in medical imaging devices.

In embodiments, the present invention may provide a way to reduce the size, weight, and cost of any imaging system that currently utilizes a planar imager and associated optics. As such, the present invention may provide general benefits to any optics system.

Figure 26:
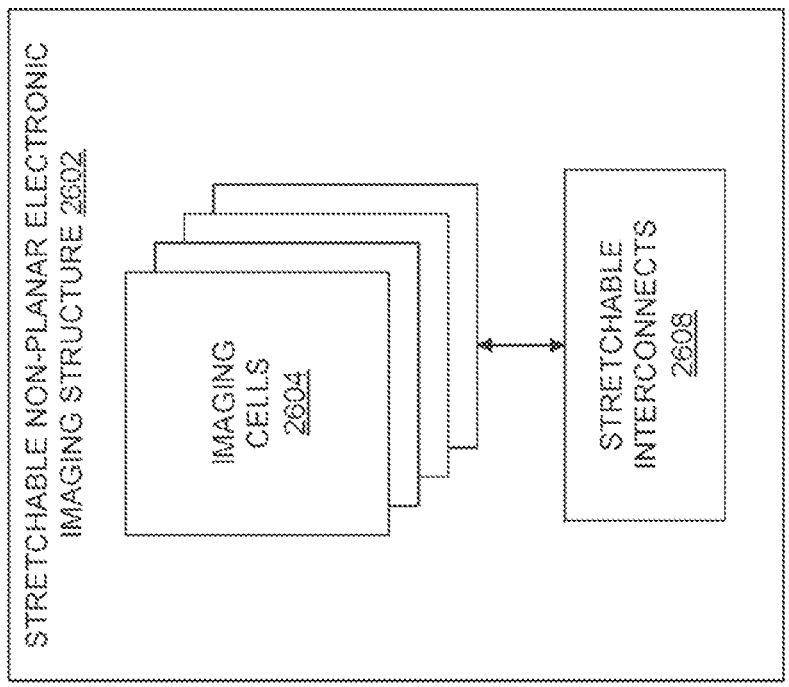
FIG. 26 depicts an embodiment for a stretchable interconnect non-planar electronic structure.

Referring to FIG. 26, in embodiments the present invention may provide for an imaging array structure, comprising a stretchable non-planar electronic imaging structure 2602, where the structure includes semiconductor imaging cells 2604 electrically interconnected with stretchable interconnections 2608. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 27:
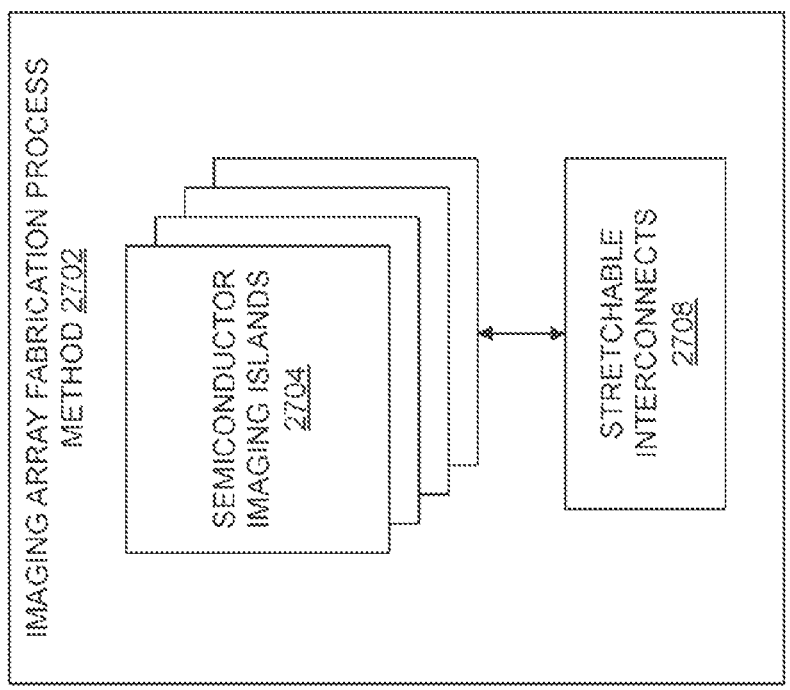
FIG. 27 depicts an embodiment for a stretchable non-planar electronic imaging device fabrication process using interconnected islands of semiconductor elements.

Referring to FIG. 27, in embodiments the present invention may provide for an imaging array fabrication process 2702 method, comprising fabricating an array of semiconductor imaging islands 2704 from a single-crystal semiconductor substrate, and interconnecting the imaging islands with stretchable interconnections 2708. The semiconductor imaging islands may include at least one imaging pixel and support electronics for controlling and reading out the image from the at least one imaging pixel. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 28:
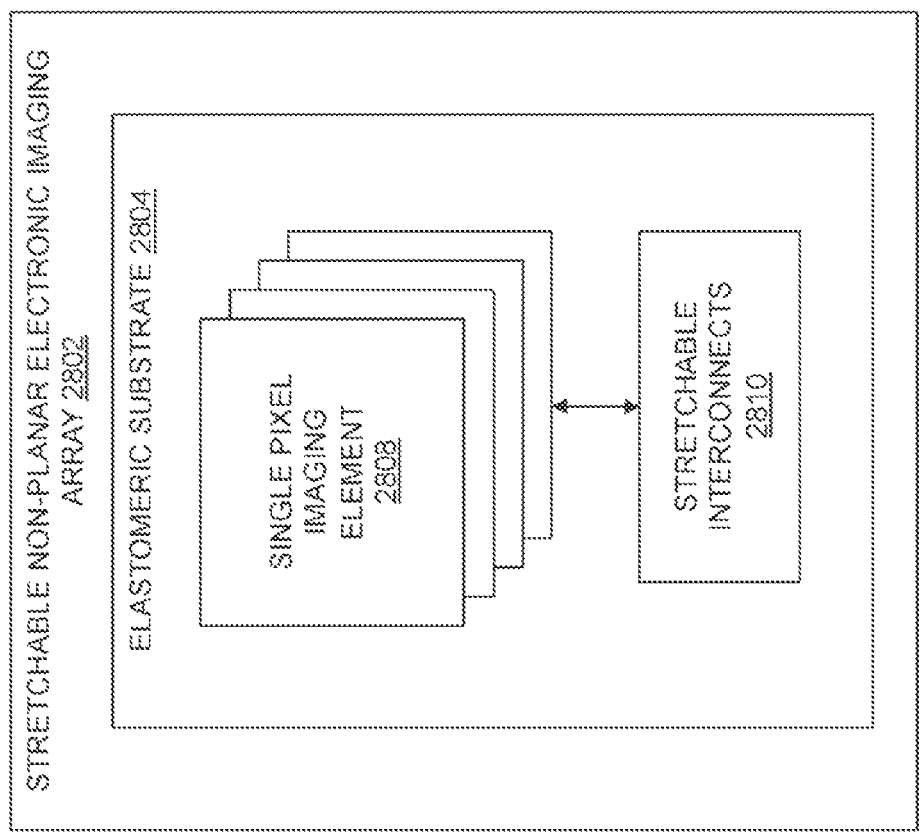
FIG. 28 depicts an embodiment for a single-pixel non-planar electronic imaging array with stretchable interconnects.

Referring to FIG. 28, in embodiments the present invention may provide for an imaging array facility, comprising a stretchable non-planar electronic imaging array 2802, where the array may be made up of a plurality of single pixel semiconductor imaging elements 2808 electrically interconnected with stretchable interconnections 2810 and mounted on an elastomeric substrate 2804. Each of the single pixel semiconductor imaging elements may include support electronics. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 29:
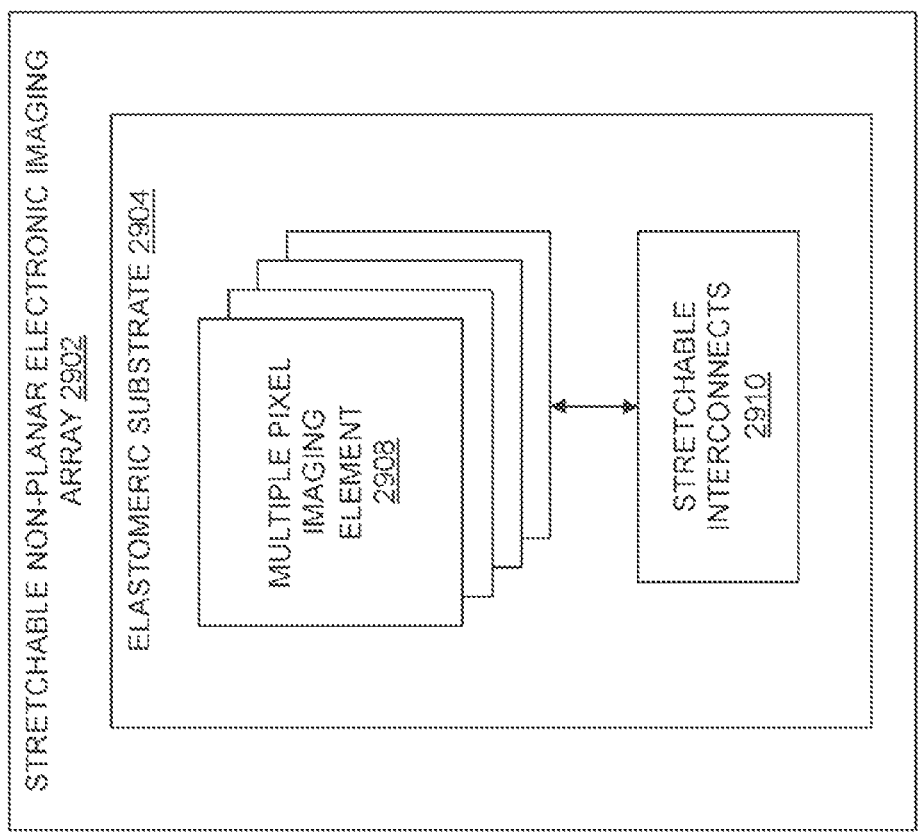
FIG. 29 depicts an embodiment for a multiple-pixel non-planar electronic imaging array with stretchable interconnects.

Referring to FIG. 29, in embodiments the present invention may provide for an imaging array facility, comprising a stretchable non-planar electronic imaging array 2902, where the array may be made up of a plurality of multiple pixel semiconductor imaging elements 2908, and where the imaging elements may be electrically interconnected with stretchable interconnections 2910 and mounted on an elastomeric substrate 2904. Each of the multiple pixel semiconductor imaging elements may include support electronics. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like.

Figure 30:
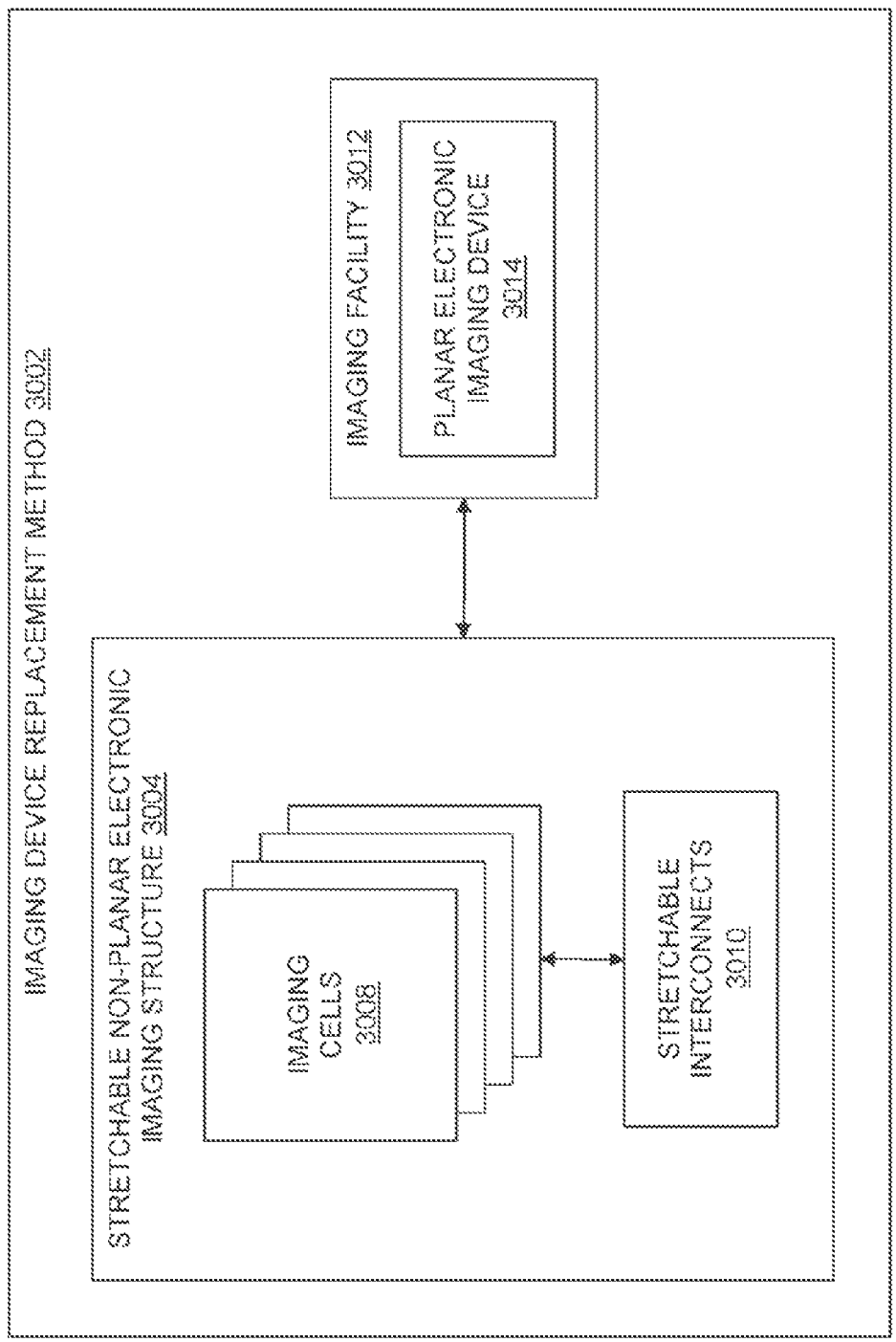
FIG. 30 depicts an embodiment for a stretchable non-planar electronic imaging device for replacement of a planar electronic imaging device.

Referring to FIG. 30, in embodiments the present invention may provide for an imaging device replacement method 3002, comprising a stretchable non-planar electronic imaging device 3004, where the structure may include semiconductor imaging cells 3008 electrically interconnected with stretchable interconnections 3010, and replacing a planar electronic imaging device 3014 in an imaging facility 3012 to improve the imaging performance of the imaging facility. The replacement may be an integrated replacement with the imaging facility, an imaging sensor within the imaging facility, and the like. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 31:
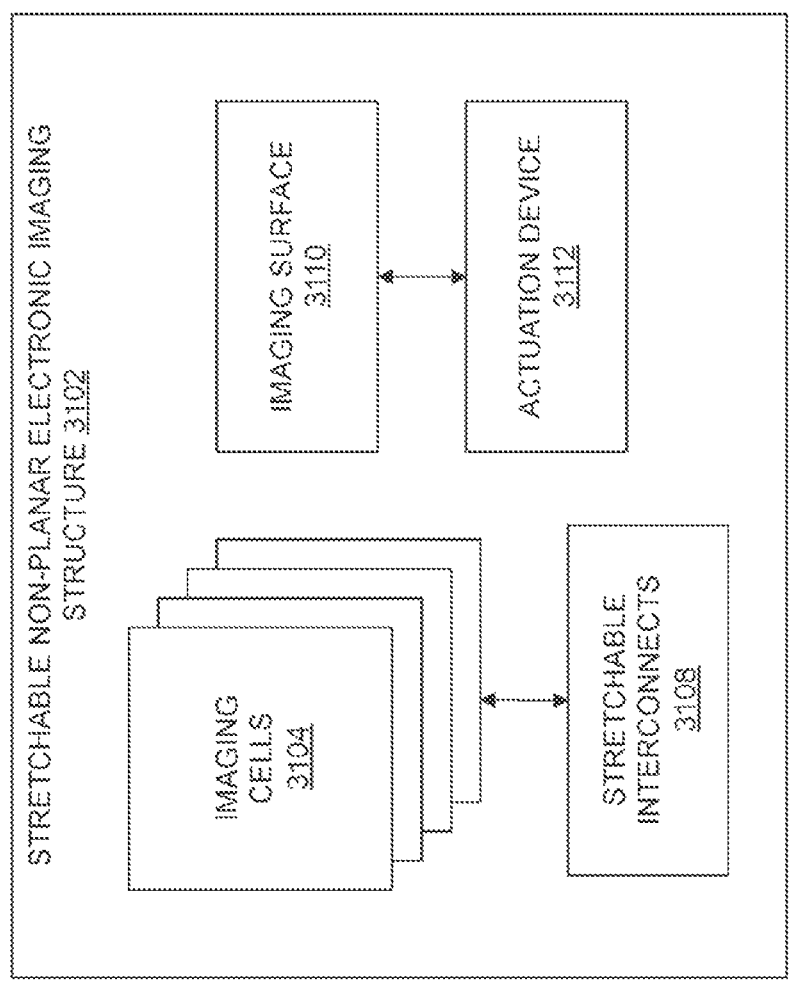
FIG. 31 depicts an embodiment for a stretchable non-planar electronic imaging structure whose surface is altered by mechanical actuation.

Referring to FIG. 31, in embodiments the present invention may provide for an imaging facility, comprising a stretchable non-planar electronic imaging structure 3102, where the structure may include semiconductor imaging cells 3104 electrically interconnected with stretchable interconnections 3108, and at least one mechanical actuation device 3112 attached to the imaging structure, where the actuation device may be capable of changing the shape of an imaging surface 3110 of the imaging structure. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 32:
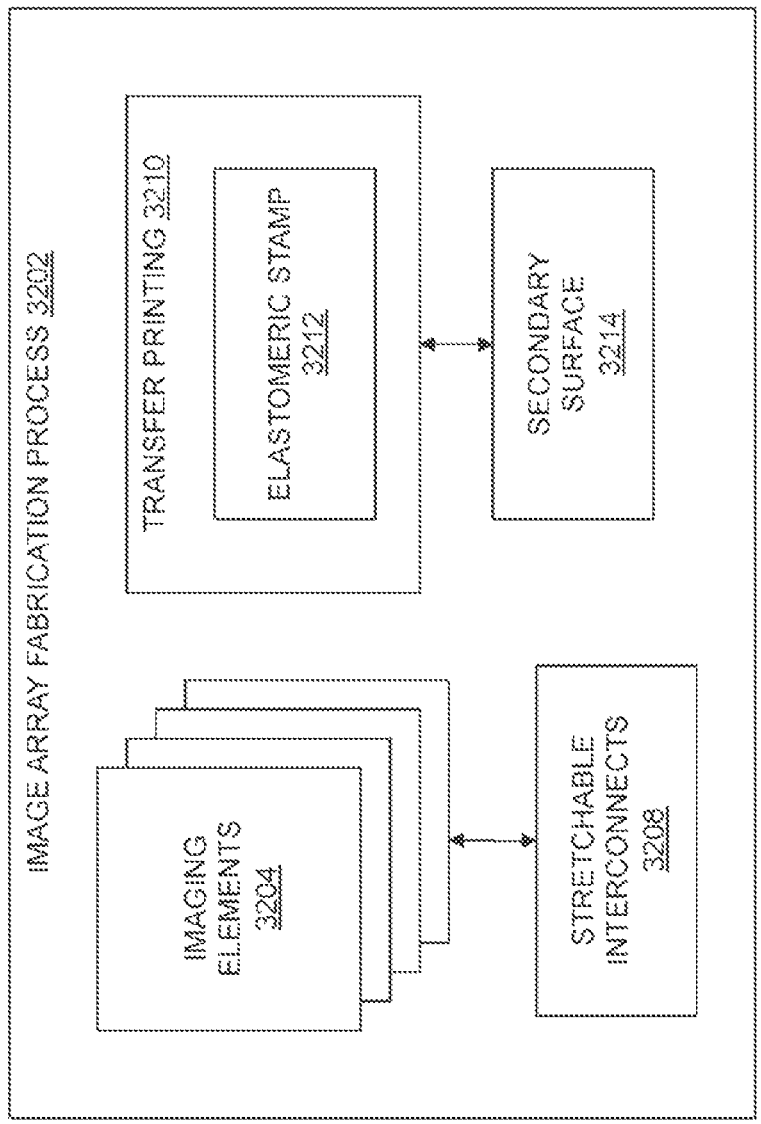
FIG. 32 depicts an embodiment for a stretchable non-planar electronic imaging device fabrication process using transfer printing.

Referring to FIG. 32, in embodiments the present invention may provide for an imaging array fabrication process 3202 method, comprising fabricating an array of semiconductor imaging elements 3204, interconnecting the elements with stretchable interconnections 3208, and transfer printing 3210 the array with a pre-strained elastomeric stamp 3212 to a secondary non-planar surface 3214. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 33:
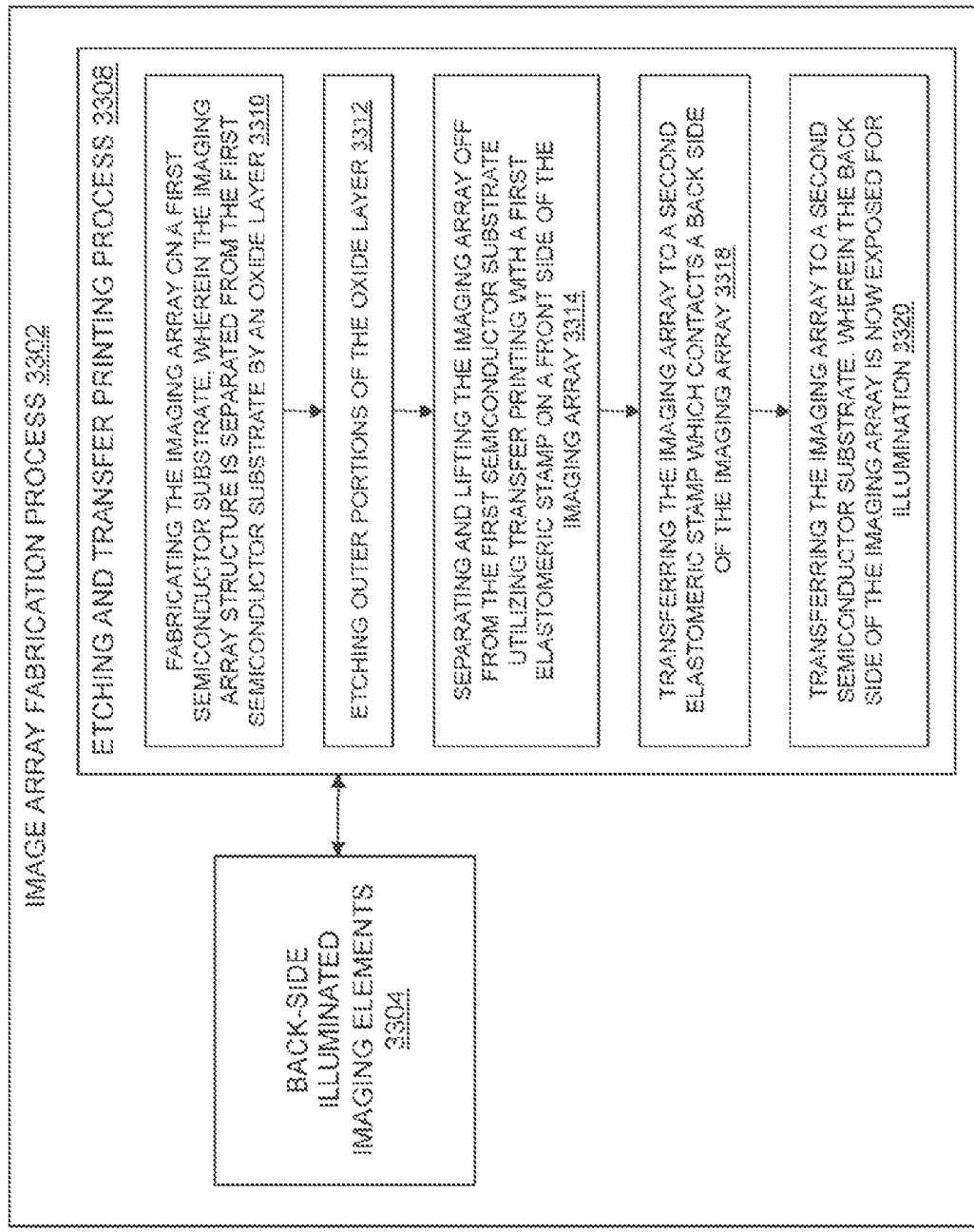
FIG. 33 depicts an embodiment for a planar electronic back-side illumination imaging device fabrication process using transfer printing.

Referring to FIG. 33, in embodiments the present invention may provide for an imaging array fabrication process 3302 method, comprising fabricating an imaging array of semiconductor back side illumination imaging elements 3304, where the fabrication of the imaging array may includes etching and transfer printing 3308 steps: (1) a first step 3310 fabricating the imaging array on a first semiconductor substrate, where the imaging array structure is separated from the first semiconductor substrate by an oxide layer, (2) a second step 3312 etching outer portions of the oxide layer, (3) a third step 3314 separating and lifting the imaging array off from the first semiconductor substrate utilizing transfer printing with a first elastomeric stamp on a front side of the imaging array, (4) a forth step 3318 transferring the imaging array to a second elastomeric stamp which contacts a back side of the imaging array; and (5) a fifth step 3320 transferring the imaging array to a second semiconductor substrate, where the back side of the imaging array is now exposed for illumination. In embodiments, a lens may be attached to at least one of the back side illumination imaging elements, such as a micro-lens. A filter may be attached to at least one of the back side illumination imaging elements, such as a color filter. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

FIG. 34A shows an embodiment of the invention wherein circuitry 1000B is stretchable and on an expandable/stretchable substrate 200B which in this embodiment is an inflatable body. In some embodiments (such as the one shown in FIG. 34A) the inflatable body is a balloon on a catheter 220B. The skilled artisan will appreciate that the balloon and catheter together are referred to as a "balloon catheter" 210B, which is a type of catheter with an inflatable balloon at its tip and which is used during a catheterization procedure for various medical procedures such as to enlarge a narrow opening or passage within the body. The deflated balloon catheter 210B is positioned, then inflated to perform the necessary procedure, and deflated again in order to be removed.

FIG. 34A shows the balloon catheter 210B in a relaxed or deflated state, which is inserted into a lumen 2010B, which in this embodiment is an artery. FIG. 34A also shows arterial plaque 2020B formed on the inner wall of the artery 2010B. The stretchable electronic circuitry 1000B is configured in the manner described above with reference to the various embodiments of stretchable circuitry and is thus applied to the surface of the substrate, i.e., inflatable body 200B according to the applicable techniques described above. In embodiments, the circuitry 1000B utilizes complementary metal-oxide semiconductor (CMOS) technology.

FIG. 34B shows a detailed view the circuitry 1000B while the device is in a deflated or unexpanded state. As mentioned above, the circuitry 1000B of the invention comprises at least one device, which is depicted in FIGS. 34A and 34B as discrete device 1010B. As described above, in embodiments the electronic device is in electronic communication with at least one other device 1010B. In embodiments, the devices are arranged in a "device island" arrangement as described herein and are themselves capable of performing any of the functionality of the circuitry described herein or portions thereof, including the that which has been described for elements 1100-1700 in FIG. 1A, the exemplary embodiments below, or portions thereof. Thus, in embodiments, such functionality of the devices 1010B (or any such electronic device herein) can include integrated circuits, physical sensors (e.g. temperature, pH, light, radiation etc), biological and/or chemical sensors, amplifiers, A/D and D/A converters, optical collectors, electro-mechanical transducers, piezo-electric actuators, light emitting electronics which include LEDs, and combinations thereof.

In embodiments, in order to accommodate the devices 1010B, which may be rigid, to the demands of an expandable and stretchable substrate 200B such as a catheter balloon 210B, the devices 1010B are fabricated such that they are located in discrete and isolated "device islands" and are electrically interconnected with stretchable interconnects 1020B, or interconnects configured to accommodate an expandable or stretchable surface. As with all elements of the circuitry 1000B, the interconnects 1020B can be fabricated according to techniques described herein and thus may be configured differently than what is depicted and described with reference to this exemplary embodiment.

In this exemplary embodiment, it can be seen that the interconnects 1020B are flexible and thus able to accommodate the stretching caused by the inflation of the balloon 210B (shown in FIG. 34C). Thus, the circuitry 1000B is expandable or stretchable. In the embodiment shown in FIG. 34B, the interconnects 1020B are buckled or non-coplanar when the substrate 200B is in a deflated state. When inflated (as shown in FIG. 34C), the interconnects 1020B become either coplanar or non-buckled so as to accommodate the increased distance between the devices 1010B upon inflation. Such buckling, non-coplanar interconnects, as well as circuitry having similar properties, are described elsewhere herein and apply to this and other embodiments disclosed herein.

As mentioned above, in embodiments, the electronic communication between the devices and/or between said devices and separate (external, for example) devices could be wireless. Therefore, said circuitry 1000B and/or associated devices 1010B may comprise a transducer, transmitter, or receiver capable of such wireless transmission.

The specific fabrication method for such circuitry may depend on the specific circuit classes desired to incorporate into the device, and the specific characteristics of the circuitry, including those of the devices, the interconnects, etc., and include, but is not limited to, those disclosed with respect to this exemplary embodiment. A non-limiting example of the complete fabrication steps of an exemplary embodiment of the invention (i.e., a catheter balloon instrumented with sensors and/or effectors or a substrate comprising stretchable/flexible circuitry comprising sensors and/or effectors capable of conforming to the surface of a tissue of interest, in particular a surface of the heart), is described in the following paragraphs. It should be noted that the embodiment described below refers to an inflatable system (specifically a catheter balloon) in some cases. The skilled artisan will appreciate the principals of operation of the embodiment and the manufacture thereof will apply to situations where the substrate on which the circuitry is applied is otherwise stretchable or expandable but not inflatable, or where the substrate is inflatable but not necessary stretchable as described above with reference the FIG. 1A and tin he discussion of substrates. Also, if a particular step or element applies only to an inflatable substrate, the skilled artisan will appreciate such fact.

In embodiments herein including but not limited to those described herein for balloon catheters, cardiac ablation devices, a nerve bundle prosthesis, endoscopy, tissue screening, and conformal sensor tapes or sheets the arrays of devices, which may include temperature sensors, conductivity sensors, pressure sensors, electrical stimulators, as well as associated differential amplifiers, buffers, A/D converters, logic, memory, clock and active-matrix switching transistors are laid out in a "device island" arrangement. The device islands can be from 1 to 50 μm×1 to 50 μm squares, which may accommodate one or more sensor units or circuits (e.g., a temperature sensor connected to a buffer that itself is connected to an amplifier). If a temperature sensor is included, the temperature sensor may be resistive, diode-based, etc., as described in greater detail below, and may supply a signal that reflects temperature (or a temperature change). Further the remaining sensor circuitry conditions the signal for subsequent processing.

In embodiments herein including but not limited to those described herein for balloon catheters, cardiac ablation devices, a nerve bundle prosthesis, endoscopy, tissue screening, and conformal sensor tapes or sheets some of the devices may accommodate active array or matrix switches and A/D converters for transforming an analog signal into digital form (for example, temperature), and some devices will thus accommodate logic circuitry capable of reading in digital signals and processing them (e.g., to assign a value to the sensed temperature or temperature change). These circuits may output the sensor reading to another module or, and are capable of outputting data or storing it in on-board memory cells.

In embodiments herein including but not limited to those described herein for balloon catheters, cardiac ablation devices, a nerve bundle prosthesis, endoscopy, tissue screening, and conformal sensor tapes or sheets, the circuitry is arranged and designed such that preferably only about one, but preferably not more than about 100 electrical interconnections are required between any two device islands. In embodiments, the circuitry is then fabricated on an SOI wafer (although it should be understood that standard wafers could be used) (1.2 µm thick top Si, 1 µm thick buried oxide) using standard CMOS fabrication technology, and the silicon space in between each island is etched away to isolate each island. The circuits are protected by a polyimide passivation layer, then a short HF etch step is applied to partially undercut the islands. The passivation layer is removed, and then a thin film of SiO2 is deposited and patterned (100 nm thick) by PECVD or other deposition technique combined with a liftoff procedure, such that the oxide layer covers most of the space between devices (a/k/a device islands) except for a region around each device island that is about 5 µm wide. Another polyimide layer is spun on and patterned into the shape of the interconnects. Typically one interconnect may extend from the center of one device to the center of another device. Alternately, two interconnects may extend from each corner of the device to two different device corners. Alternatively, one interconnect may extend from the center of one island edge to the center of another island edge. The interconnect bridges may be about 25 µm wide and may accommodate multiple electrical lines. The polyimide partially fills where the device island is undercut; this serves to stabilize the island later in the release process and to prevent its migration. VIAs are etched into the PI layer to allow metal wires, patterned in the next step, to contact the circuits and connect one island to another. (This step can be repeated to form additional sets of wires located above the first set). Another PI layer is spun on (covering the wires and everything else). The PI (both layers) is then isolated by etching with a deposited SiO2 hard mask, in O2 RIE. PI located outside the devices and bridges is etched, as well as PI covering areas that are meant to be externally electrically interfaced, and small areas leading to the underlying oxide. Etch holes may be formed if necessary and then transferred through the silicon or metal layers by wet and/or dry etching. The underlying buried oxide is etched away using HF etchant to free the devices, which remains attached to the handle substrate due to the first polyimide passivation layer which contacts the handle wafer near the border around the devices.

If the HF etch is not controllable enough and seeps under the PI isolation layer and thereby attacks the CMOS devices, then prior to the first PI passivation a brief Argon sputtering can be done to remove any native oxide followed by amorphous silicon sputtering followed by the PI passivation and the rest of the processing. After rinsing, the devices are left to air dry. They may then be transferred from their silicon mother wafers to a desired surface via soft lithography tools. Circuits may be picked up with an elastomeric stamp (e.g. PDMS), and transfer printed onto either the polymeric substrate directly, or a polymer surface coated with a thin PDMS layer, or a separate thin PDMS layer (that, in embodiments where applicable, may later be wrapped around an inflatable substrate or three-dimensional substrate).

The circuits of embodiments of the invention disclosed herein may also be manufactured as follows:

Starting with a SOI wafer, 300 nm thick top silicon layer on 1 µm buried oxide, areas of the top silicon are doped appropriately with n and p type dopants based on the desired devices. Around this area, which contains circuits, a border is formed by an RIE process.

In the same step, etch holes are defined within the area. With a photoresist mask still on top of the silicon, HF is used to undercut all of the buried oxide under the circuit area, to form a silicon membrane with doped regions. This membrane is transfer printed onto another substrate that has a polymer-based sacrificial release layer. In this example, the substrate is a silicon wafer with a 100 nm coating of PMMA and a 1 µm coating of polyimide (PI) on top. The PMMA is the sacrificial layer and the PI is partially cured in this configuration. The membrane of silicon is transfer printed into the PI, the photoresist on top of the silicon is rinsed away in acetone, and the PI is subsequently fully cured. Next, the silicon membrane is etched into discrete, non-interconnected device islands using RIE, such that the RIE stops on the PI layer. The circuit fabrication is completed, including gate oxides and other required processing, with the caveat that the processing must take place at temperatures lower than about 300° C. to ensure compatibility with the underlying polymer layers. Therefore, for gate oxides, PECVD may be used. Conductive interconnects (typically metal) are then formed between device islands. These may connect from any point on the surface of the device islands, and may be isolated when necessary with standard passivation layers. Another coating of 1 µm PI coats the entirety of the circuits, and is patterned and etched through the PMMA to the silicon. The pattern encompasses the device islands and interconnects, and removes all of the PI elsewhere. Etch holes may also be formed in this step if necessary.

The devices may be released by immersion in hot acetone, which removes the underlying PMMA. The substrate is removed, and then the devices and interconnects are picked up by a PDMS stamp. At this point, they are fully encapsulated on top and bottom surfaces by PI.

Figure 35A:
FIG. 35A shows a side view of a balloon with a PDMS layer wrapped around the surface of the balloon.
Figure 35B:
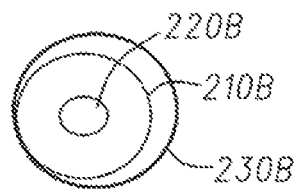
FIG. 35B is a cross-sectional view which shows the catheter, the surface of the balloon, and the thin PDMS layer applied to the balloon.

In connection with some embodiments, after drying, devices may be picked up with a PDMS stamp, and transfer printed onto either the surface of the substrate, such as for example a catheter balloon 210B, or a surface of the substrate coated with a thin PDMS layer, or a separate thin PDMS layer (that may later be wrapped around the substrate). FIG. 35A shows a side view of a balloon substrate with the PDMS layer 230B wrapped around the surface of the balloon. FIG. 35B is a cross-sectional view which shows the catheter 220B, the surface of the balloon 210B, and the thin PDMS layer 230B applied to the balloon.

In embodiments, the method of transfer printing may involve the use of a thin elastomeric mold in the shape of the receiving substrate. This elastomeric mold may be referred to as the geometric stamp as it serves the purpose of shaping the stretchable circuitry into the desired shape. It is fabricated such that it may be stretched flat by a mechanical jig supplying uniaxial force around the outer bounds of the material. The degree of expansion of the final embodiment of the substrate depends on the degree of expansion in this step. Thus, in order to have a highly elastic matrix of device islands the geometric substrate/stamp must be stretched to a similarly high degree. This planar stamp is then used to retrieve stretch processed circuits from the under etched wafer or the circuits may be transferred onto the planar stamp by use of an elastomeric transfer post. The planar stamp is released from strain to reproduce its initial shape. This action compresses the island/interconnect network which complies with the form of the non-planar stamp. The stamp may then be integrated directly onto the receiving substrate using a suitable adhesive.

In accordance with the above method, a rectangular elastomeric thin film (e.g. PDMS) may be used instead of a geometric stamp. The rectangular sheet may or may not be prestrained before accepting electronics arrays. After accepting the circuitry, the rectangular sheet is relaxed (if prestrained) then wrapped around the substrate (if the substrate is three-dimensional or inflatable) with the aid of a suitable polymer adhesive. The substrate, if it were an inflatable body, would typically be in its deflated state at this point, however, various degrees of inflation may be considered based on the expansion requirement for the particular application.

In embodiments, another method of transfer printing involves direct transfer of the circuitry to the surface of the substrate. The circuitry is picked up from the mother wafer after release and the backsides of the islands are then selectively coated with a 3 nm Cr/30 nm SiO2 layer by shadow masked evaporation (and then cured in UV ozone to improve their adhesion relative to the interconnects). Subsequently, the arrays of devices and interconnects are transfer printed onto the surface of the substrate, which (if applicable) may be in the inflated, deflated, or partially inflated state depending on how the interconnects were designed to accommodate a particular amount of compressive or tensile strain. The islands preferentially stick to the substrate, but not the interconnects, which are able to stretch and compress freely.

In one or more embodiment it may be advantageous to transfer the electronic island arrays to the inner surface of an inflatable substrate. This is done using similar printing methods to the ones described above.

In embodiments having an inflatable substrate, it is possible for a thin PDMS mold to be made of half the (inflated) balloon shape (in embodiments involving an inflatable body), such that it can be stretched flat, and have circuits transferred onto it in the flat state, and then released to pop back into the half-balloon shape; this half-balloon can then be easily attached to the real balloon, and may even be glued. It is noted that in some cases where the circuits are on the outside of the balloon, the bridges (also referred to as interconnects and physical electrical connections herein) pop or buckle outward when the devices are compressed or the expendable/inflatable body is otherwise in a relaxed or deflated state. In the inflated state, the bridges 1020B should be fairly non-buckled and/or coplanar with the surface of the substrate 200B so that in the deflated state they can buckle to accommodate the significant compressive stress.

Alternately, this process can be repeated with a mold made in the deflated state of the balloon, and stretched beyond flat so that it is significantly expanded, such that after the circuits are transferred and the mold is released, they compress significantly. In this case, they should be compressed enough so that after transfer to the actual balloon, when it is fully expanded, the bridges are nearly flat or fully extended and almost non-buckled.

In embodiments where the circuitry is directly transferred to the substrate, the PDMS stamp should be made thin (~100-500 µm in thickness) and thereby compliant enough to conform to the shape of the subject tissue, for example, the heart chambers or body lumen. To further increase PDMS compliance, the weight ratio of elastomer to curing agent (ingredients that make up PDMS) can be altered in favor of more elastomer (20:1 and/or up to 50:1).

In embodiments where the circuitry is first transferred to a separate thin PDMS layer, the PDMS layer may be on a rigid substrate so that the transferring can be done easily. Then the PDMS layer can be peeled off the substrate and wrapped around the substrate either in the inflated or deflated state (if applicable), depending on whether the circuits were transferred with prestrain or not. It may be desirable to make the circuits in a 1D array rather than a 2D array. In this way, the thin PDMS layer is a long, narrow ribbon that can be easily wrapped around the inflatable substrate so as to cover the entire surface of the substrate. Alternatively, if it is desired that the circuits face inwards to the substrate, the substrate can be directly rolled along a planar array of circuits on PDMS carrier substrate. If inflatable, the substrate can be subsequently deflated and/or re-inflated. Deflation can cause the interconnects in the circuitry to buckle and take on compression forces imposed by deflation. It should be understood that these stamping methodologies applied to the balloon catheter can be applied to stamp the electronic circuitry in all of the embodiments described below.

Figure 36:
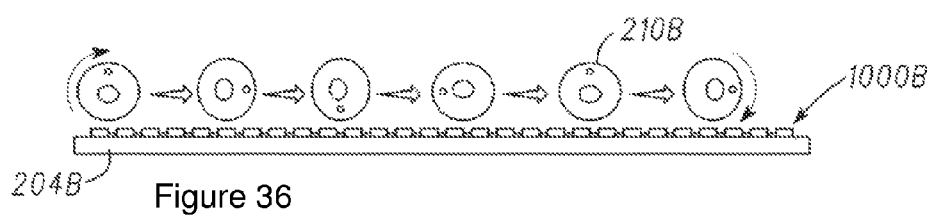
FIG. 36 depicts a process for applying stretchable circuitry to the surface of a catheter balloon.
Figure 37A:
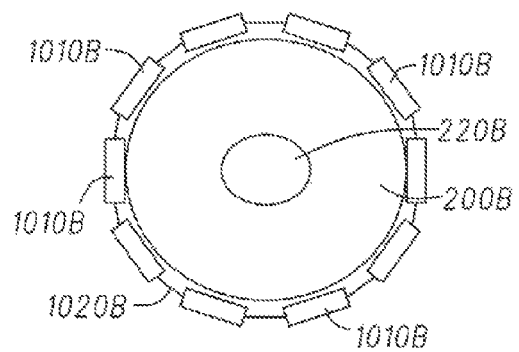
FIG. 37A depicts an example of a stretchable circuitry on the surface of a catheter balloon that is in an inflated state, wherein the interconnects in the circuitry are substantially coplanar with the substrate by way of the inflation.
Figure 37B:
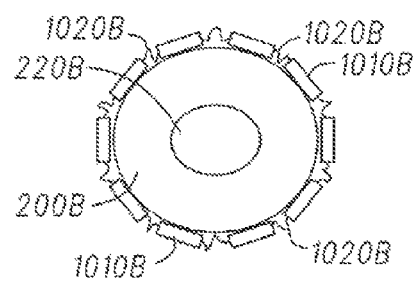
FIG. 37B depicts an example of a stretchable circuitry on the surface of a catheter balloon that is in a deflated state, wherein the interconnects in the circuitry buckle and take on compression forces imposed by deflation.
Figure 38:
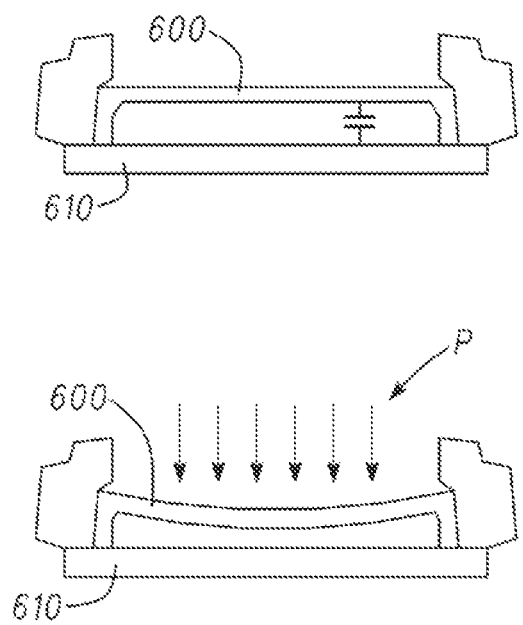
FIG. 38 is an embodiment of a pressure sensor utilized with embodiments of the invention.

Thus, in embodiments, to apply the circuitry, the balloon 210B can be directly rolled along a planar array of circuitry 1000B on PDMS carrier substrate 204B as shown in FIG. 36. The balloon can be subsequently deflated and/or re-inflated. Deflation can cause the interconnects in the circuitry to buckle and take on compression forces imposed by deflation as shown in FIG. 37B, while inflation causes the interconnects to be substantially coplanar with the substrate (as shown in FIG. 37A). This principle may apply to inflatable, stretchable, and flexible embodiments herein. Further, it should be understood that the described stamping methodologies applied to the balloon catheter can be applied to stamp the electronic circuitry in all of the embodiments described herein.

In embodiments circuitry may be encapsulated (in embodiments, while in its compressed state) with another layer of PDMS, or a liquid layer of PDMS followed by an upper layer of solid PDMS to make a fluid encapsulation.

In embodiments where the circuitry is facing outwards on the balloon, it may be electrically externally interfaced at conductive pads that should be designed to be located at the base of the balloon. Anisotropic conductive film (ACF) connectors can be used to interface to these conductive pads, by pressing and heating the film onto the pads. The film can then run down the length of the catheter since it is so thin and flexible.

In embodiments where the circuitry is encapsulated (insulated), it (said circuitry) may be made accessible to electronic contact by selective etching of the encapsulating layer to reveal contact pads. The ACF can now be bonded to these exposed contact pads. Alternatively, the ACF may have been bonded to contact pads of the stretchable circuitry before encapsulation.

As described above, in embodiments the circuitry may be powered externally optically, using the catheter tube as a waveguide and having PV cells made in a stretchable format in addition to the rest of the circuitry. Photovoltaic cells may harness light energy from outside of the body and channel electric power to the stretchable circuitry on the substrate, e.g., balloon catheter or sheet. The catheter tube may also be used as a waveguide and having PV cells made in a stretchable format on the balloon portion of the catheter addition to the rest of the circuitry. In addition, LED islands can be made to perform optical data communication down the catheter waveguide. Alternately, thin film batteries may be used to power the circuitry. Alternately, RF communication circuits on the device may be used to wirelessly communicate outside of the body, and may also receive RF power to power the circuits. Using these approaches, the need for external electrical interfaces may be reduced or eliminated.

In an embodiment of an apparatus of the present invention involving but not limited to the exemplary embodiment of the balloon catheter or cardiac ablation device presently being described, the substrate (in this embodiment, a catheter balloon 210B) is covered with stretchable circuitry 1000B having an array of devices 210B and may be inserted in a lumen 2010B of the subject's body. The devices may include temperature sensors. The temperature sensors may be, for example, silicon band gap temperature sensor, consisting of silicon diodes. The forward voltage of these silicon diodes is sensitive to changes in temperature. Alternatively, platinum thin-film resistance temperature devices (RTD), which measure temperature based on temperature-induced changes in electrical resistance or thermocouple circuits that sense temperature changes between different thermoelectric materials can be utilized. For thermal resistors, the normalized changes in resistance (R), temperature coefficients of resistors (a), are related to the change in temperature (T) by $$\Delta R/R = \alpha T.$$

Platinum (500 Å) and an adhesion layer of chromium (150 Å) can be patterned and deposited on SOI wafers using thermal evaporation via e-beam to define individual RTD sensors. The RTD sensors can be integrated with CMOS based amplifiers, transducers, computation logic elements, and A/D circuitry on the same device islands as previously described.

Once the circuitry is transferred onto the substrate in some embodiments, a balloon catheter 210B, stretching and fatigue tests can be performed with a mechanical bending stage, capable of applying uneasily tensile or compressive strains in multiple directions or by repetitive inflation and deflation loading cycles. The mechanical bending stages can work in parallel with electrical probing stations (Agilent, 5155C) that are coupled to the circuit semi-conductors. In embodiments, to evaluate the performance of the circuitry, multiple cycling of heating and cooling tests can be performed. The circuits can be heated to 160° C. for 5 min. and subsequently cooled down before and after each electrical measurement.

In embodiments and in others where it is desirable to protect the circuitry from external damage, an encapsulating thin layer of polymer can be applied to the circuitry, including on the surface of the inflatable body after the circuitry is applied thereto according to the description below and other applicable encapsulation methods described herein. This encapsulating polymer layer may be extremely thin (<100 um) and photocurable in order to allow selective curing in regions where direct contact with sensors is not required. Thus, areas of the device that do require direct or conformal contact with the tissue of interest may be exposed. Such selective encapsulation is described below, but any technique for selective encapsulation described herein may apply. It should be noted all methods of selective encapsulation apply to any embodiment disclosed herein.

In embodiments, the RTD temperature sensors may be preferentially exposed for direct contact during photocuring. There are several polymers that may be used for preferential photocuring of the encapsulating layer, including but not limited to polyethylene glycol (PEG) with 2-hydroxy-2-methylpropiophenone photoinitiator. The photocurable PEG encapsulation cures once it is exposed to ultraviolet light. Photomasks designed using AUTOCAD can be printed to allow preferential curing of the surface of the inflatable body. These masks can be inserted as a filter into a UV light source stage coupled with a wide excitation UV filter. Exposure with an aligned mask enables polymerization in strategic regions of the inflatable body. Visual alignment during polymerization can be achieved with a CCD camera.

In embodiments, the substrate is instrumented with an array of devices—comprising sensors such as temperature sensors, or electrodes which may comprise sensors or effectors—can be deployed such that the temperature sensors are positioned in direct contact and or conformal with the tissue or surface of interest, which in embodiments, may be surface of plaque in the lumen upon inflation of the inflatable body. An important advantage realized in this embodiment, and in other embodiments having the flexible and/or stretchable circuitry described herein is that the circuitry (and thus its devices such as sensors) can not only come into direct contact with the surface or tissue of interest (for example, the plaque and inner surface of the lumen, inner or outer surface of the heart), but also achieve conformal contact with the contours and/or surface features of the surface or tissue so as to achieve greatly improved performance.

In embodiments, the separation distance between sensors can be any that is manufacturable, a useful range may be, but is not limited to, 10 μm-10000 μm. Individual sensors may be coupled to a differential amplifier, and/or a buffer and/or an analog to digital converter. These circuits may be formed on the same, or different, devices than the sensors or effectors. The circuits may be laid out in an active array or matrix fashion such that the readings from multiple temperature sensors can be switched into and processed by one or a few amplifier/logic circuits. These sensor arrays record input signals that can then be channeled from the surface of the substrate to guide wires and a processor using metal electrodes deposited near the junction between the substrate surface and the catheter tubing. Alternatively, gold metal wires may be used to attach the circuitry on the substrate to the surface of the catheter guide wire using a wire bonder. Signals from the array of sensors can be processed using multiplexing techniques, including those described in published international patent application WO2009/114689 filed Mar. 12, 2009 the entirety of which is hereby incorporated herein by reference. Multiplexor component circuitry located in the base of the catheter guide wire can facilitate this type of data analysis/processing.

Relevant to that which was discussed above in connection with FIG. 1B, such multiplexing techniques disclosed herein allow for the circuitry (or an operator) to select which active devices should be utilized, or what pattern of active devices should be functioning. Processing facility is configured to generate a user interface on output facility such that the operator may make said selections or adjustments. In some cases the identity or pattern of active devices being utilized is based upon whether (or the degree to which) the devices are in electrical or conformal contact with the tissue of interest. Thus, all embodiments herein are able to generate useful amounts of data even when all electronic devices are not in complete contact with the area of interest on the tissue, but may only be in partial contact.

In embodiments, the device operator may use optical guidance during an x-ray angiography to deploy the balloon catheter once the guide wire reaches the region of the plaque location. The deformable and stretchable nature of the catheter balloon allows temperature measurements at multiple contact points on non-uniform surface contours such as that of arterial lumen and deposited plaque (shown as 2020B in FIGS. 34A and 34B). The conformal capabilities of the circuitry enable such abilities. Once deployed, the processing facilities described herein process the transmitted signals and produce a spatial temperature map of the plaque in the lumen. This data can be used by the device operator to detect temperature heterogeneity presence along the plaque and determine plaque type. Once plaque type is determined and surface contours are characterized, the balloon catheter can be deflated and removed.

In another embodiment of the invention, the stretchable circuitry 1000B comprises pressure sensor arrays. Such sensor arrays may be silicon-based and utilize piezo-resistive or capacitive sensing, or may be polymer based or optically based. In embodiments, a pressure sensor has a working range and size suitable to the application, and should be amenable to application as described herein and tolerant to the stretching forces it will experience.

FIG. 37 shows one exemplary pressure/contact sensor which may be utilized with any embodiment described herein requiring a pressure sensor or contact sensor. The pressure sensor comprises a flexible and suspended diaphragm 600 of a flexible material such as thin single-crystal silicon, polysilicon, and/or silicon nitride thin film. The diaphragm 600 can be suspended directly above a base layer of doped silicon consisting of a metal electrode layer extracted from an SOI wafer. The polysilicon diaphragm layer may be formed as a suspended layer by first depositing an SiO2 layer on the silicon electrode 610. The polysilicon may then be deposited on the SiO2 layer, which in turn can be selectively etched. This etching step allows for the formation of a suspended and flexible polysilicon structure. In order to produce diaphragms with a controlled thickness, precise etch rates using HF must be used. This diaphragm with known thickness (2-10 μm thick), material modulus, and surface area and the underlying silicon electrode collectively form a parallel-plate capacitor. The sensor capacitance is a function of distance between the top polysilicon layer and the underlying silicon electrode. The capacitance recordings relate diaphragm deflection (caused by force P) to changes in capacitance.

In embodiments of the invention, the stretchable circuitry comprises an array of contact sensors. Tin some embodiments, the contact sensors are designed to provide an on/off electrical resistance change in response to a pressure, such that when the applied pressure exceeds a predetermined threshold, the sensor provides an electrical signal indicating that it is in contact with, e.g., the arterial wall. One example of how to form a contact sensor is to make a simple mechanical-electrical switch, in which one conductor is mechanically pressed onto another conductor. The lower conductor, located on the surface balloon, consists of a metal wire that is non-continuous in one or more places to form an open circuit. Encapsulated around this open circuit is a diaphragm formed out of PDMS. The PDMS may be molded or etched into a diaphragm shape. The upper wall of the diaphragm is coated with a metal conductor, by standard means of photolithography patterning, electrochemical etching, etching, shadow evaporation, etc. The diaphragm is aligned and bonded to the surface of the balloon. The diaphragm is designed so that when a certain pressure is applied, it bends down to allow the upper conductor to contact and short-circuit the lower non-continuous conductor. This is done by control of the geometry (height and width) and materials of the diaphragm. In yet another non-limiting example, the diaphragm may be made with MEMS techniques, such as sacrificial silicon dioxide layers with a polysilicon bridge on top.

In embodiments of the invention, to measure relative pressure, each pressure sensor can be coupled with reference sensor unit, which has identical electrical characteristics except for a significantly lower pressure sensitivity. Difference in pressure measurements between the sensor and the reference unit enable compensation for many parasitic effects. The reference units may be created by leaving a passivation layer on the top surface of the polysilicon electrode. Having a reference unit along with a pressure sensor unit allows for differential pressure recordings. Once deployed, such sensor arrays can generate data that can be used by circuitry to determine, among other things, the presence and mechanical properties of the tissue such as the presence and properties of an arterial lumen and plaque therein. In embodiments where the substrate is a balloon, such data may also be used to estimate the diameter of the balloon and the lumen and provide feedback to the device operator to end balloon inflation at this point. This type of sensing can be combined with temperature sensor arrays to provide a thorough assessment of tissue mechanical and thermal properties during a single deployment attempt.

In embodiments, data generated by such pressure sensing also allows for creation of a tactile image map of the surface contours of materials such as arterial plaque. Further, this type of mechanical imaging in balloon catheter embodiments can indicate whether a stent has been successfully deployed when the balloon is inflated.

In embodiments of the invention including a therapeutic facility 1700, plaque type is initially determined with data generated by temperature sensors and immediately afterwards, drug-delivery polymers and circuitry embedded in the balloon polymer are activated to cause local cooling and/or release of chemical agents, such as anti-inflammatory drugs, to local sites on the plaque where inflammation is present. In embodiments, therapeutic facility 1700 comprises light emitting electronics (such as LED) could be utilized to activate a drug delivery polymer.

In embodiments of the invention, circuitry comprises imaging circuitry 1600 described herein. Thus, in embodiments circuitry may comprise some combination of sensing devices, effectors devices, and the imaging devices disclosed herein. In such embodiments, processing (1200 or 1200A) is in electronic communication with the circuitry is thus programmed or configured to generate output data, outputted by output facility or the sensed data, the data generated by the imaging device or both. In such embodiments, the circuitry may also comprise a light source which may be, for example, an LED. The output from the imaging sensors may be used to provide high resolution image of the tissue. Processing facility may be programmed to superimpose or otherwise combine the data with the sensed data to create a composite graphical presentation.

In embodiments of the invention, the substrate is covered with ultrasound transducers to generate data used to produce a lateral deep-tissue image of the plaque and arterial lumen.

In embodiments of the invention, substrate is covered with stimulating and recording electrodes used for measuring plaque conductivity. Since vulnerable plaque is significantly less conductive than stable plaque and arterial tissue, this form of sensor array can help determine the plaque type based on measured conductivity of the plaque. Once the inflatable body is deployed, the electrodes are positioned in direct contact and/or conformal with the plaque deposits and electrical conductivity is measured. Again, this device can be combined with other sensor array types embedded in the stretchable inflatable body to provide multiple sensing and therapeutic functionalities in parallel.

Data collected by sensors at the site of the plaque can be interpreted against a baseline established by deploying the same inflatable body (or a second inflatable body on the same catheter) at a different location, which is free of plaque, in the lumen.

In embodiments of the invention, the array of devices includes temperature detectors, pressure sensors, and photo-detectors collectively fabricated in a flexible and stretchable polymer-based balloon catheter substrate. These active device components can be designed using 0.6 μm design feature resolution or smaller. They may be integrated on the devices that are pieces of single crystalline silicon (50×50 µm2; 1.2 µm thick). Once the balloon is inserted in the arterial lumen, the device operator navigates the guide wire leading the balloon to the plaque location. The deployment of the balloon can stop blood flow intermittently. The guide wire is preferably fitted with an optical fiber or LED; the close contact of the imaging arrays to the lumen avoids the need for optical lens arrays, since light from the optical source may pass through the interconnect gap regions between the arrays, scatter through the lumen/plaque, and reach the photodetectors directly.

In this embodiment, the pressure sensor array detects when the inflatable body initially contacts the plaque and generates data used to spatially map the entire region of contact to ensure successful deployment. Circuitry continuously records data generated by the sensors and spatially maps temperature as a way to detect where in the arterial plaque there may be inflammation and macrophage deposits. The device operator may examine the data and decide whether to take immediate action through drug-delivery measures, stent deployment, or further tests on the plaque. The device operator may also utilize light imaging to visualize the plaque. Having integrated pressure sensors and imaging sensor arrays on the balloon, in addition to temperature sensors, allows for creation of a detailed tactile, thermal and visual map of the regions where the balloon contacts the plaque. This type of distributed mechanical sensing and imaging with an array of pressure sensors and photodetectors ensures that the stent and/or balloon contact the entire surface of the plaque.

In embodiments, the lumen may be a pulmonary vein. In such embodiments, the circuitry 1000B comprises devices having sensors that generate data related to the electrical activity of the pulmonary vein which in turn can be used processing facility to generate maps of the circumferential electrical activity of the pulmonary veins. In other embodiments, the sensor may include active electrodes. Such embodiments may generate data for mapping electrical activity of the pulmonary vein. Further, embodiments may also include a pressure sensor and temperature sensor for heterogeneous sensing on a balloon to be deployed in the pulmonary vein for mapping electrical activity. Such embodiments described for the pulmonary vein may apply to any lumen. While in other embodiments, the sensor may include active electrodes for generating data used for mapping electrical activity of the septal wall, atrial wall or surfaces, and/or ventricular surfaces.

Other embodiments may include active electrodes configured to generate data to map electrical activity while the inflatable body is inflated allowing concurrent mapping and ablation as will be discussed in further detail below. In embodiments, ablation may be effected cryogenically, via laser or via RF energy.

In other embodiments, a contact sensor (including thermal contact sensor or pressure sensor) generates data used by processing device determines force per unit area applied to the ostium of the pulmonary vein which can be used to determine whether the inflatable body, i.e., balloon, is occluding the ostium during ablation.

In embodiments, the inflatable body herein may be inflated with fluid of specified temperature. Data related to the temperature of the fluid may be generated by circuitry and thus used to tune the heat output of the electronics, or to calibrate the sensors.

Embodiments, of the balloon catheter can be deployed with a stent that may be fitted around the active sensing and imaging regions of the balloon.

Figure 39:
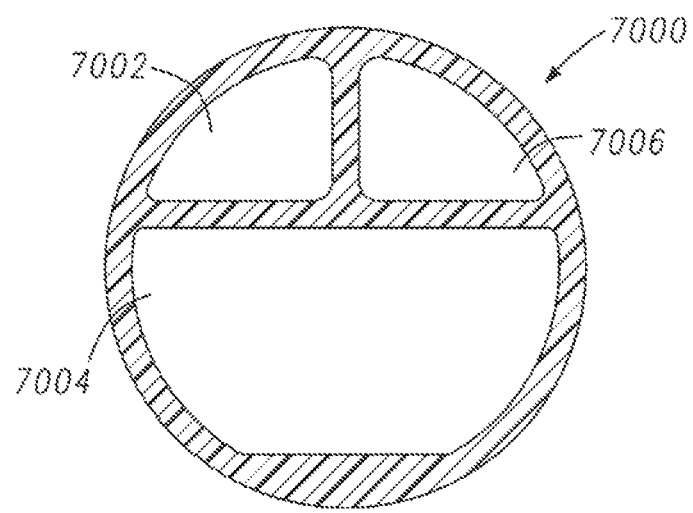
FIG. 39 is a cross-sectional view of a tri-lumen catheter according to embodiments of the invention.

Embodiments utilizing a catheter may utilize the inventive catheter described herein. FIG. 39 shows a catheter 7000 comprising three lumens: guide wire lumen 7002 (houses the guide wire); fluid injection lumen 7006 (channel for fluid which will be used to inflate balloon and or control temperature of the electrodes or active devices on the balloon surface); and the circuitry lumen 7004 (houses the flexible PCB and wiring which will be connected to the DAQ). In the assembly of the catheter system, the flexible PCB is wired for connection to the DAQ and also electrically connected to the stretchable electrode array. This unit is then threaded into the circuitry lumen, of the tri-lumen extrusion as illustrated in with the DAQ-bound wires entering first and exiting through the proximal end of the catheter for connection to the DAQ.

Figure 40:
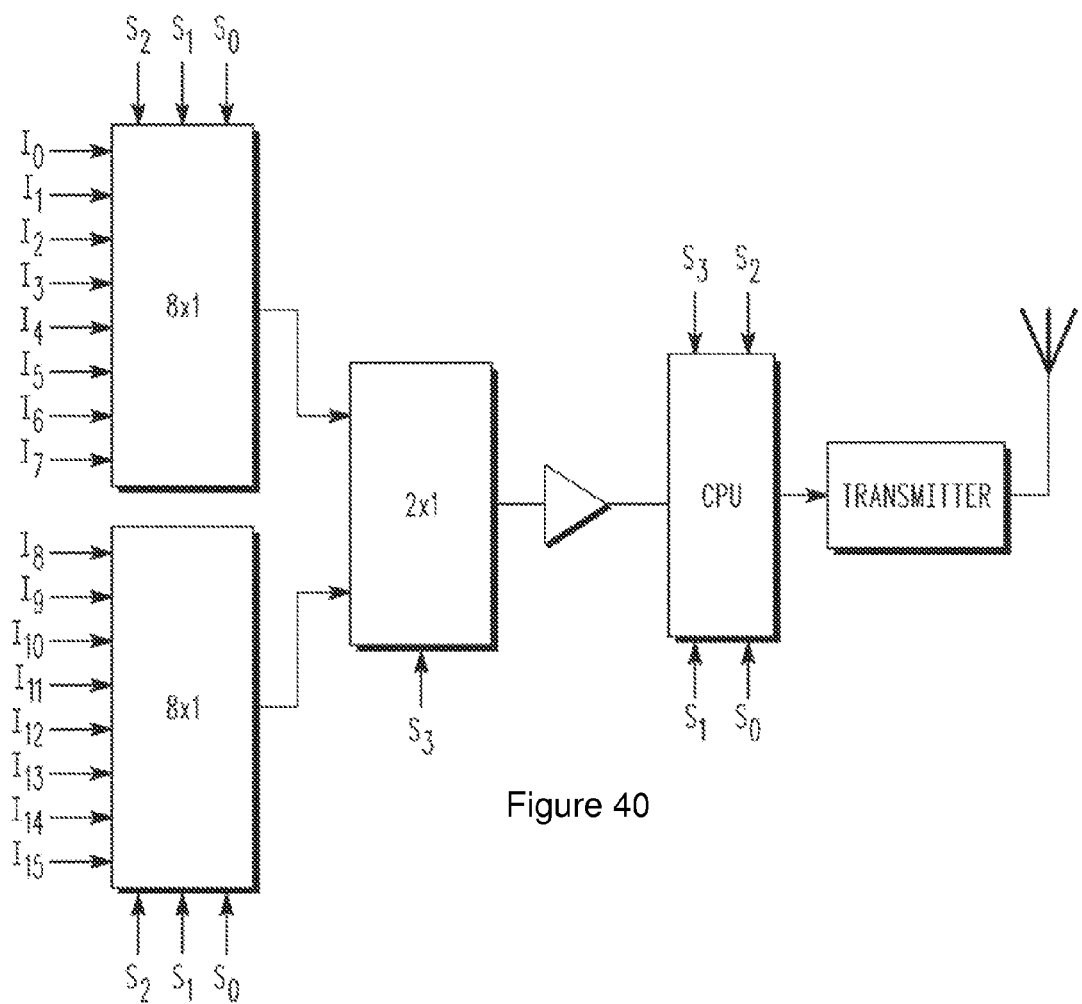
FIG. 40 schematically depicts a multiplexor according to an embodiment of the present invention.

An exemplary embodiment of the multiplexer is described in connection with the balloon catheter exemplary embodiment; although it should be understood to apply to other embodiments including those involving mapping and ablation. FIG. 40 shows a Wireless catheter statistical multiplexer that concentrates 16 (but could be other numbers) asynchronous channels over a single radio link. In FIG. 40, I1-I15 are the balloon catheter electrodes. 3 cross point switches are used for multiplexing. After the mux, an X time's amp is employed. This is feed into the A/D of the CPU and then transmitted wirelessly. Two wires are needed for power and ground (3-5V @ 5-7.5 mA).

The asynchronous ports can be individually set for speeds to 57.6 Kbps. Hardware (CTS/Busy high or low) or software (Xon/Xoff even, odd, mark, space or transparent) flow control is also set on a port by port basis.

The Wireless catheter statistical multiplexer composite is a wireless link that runs at 57.6 Kbps. It transmits on the license-free ISM or MedRadio band. The link radio modules are easily configured using a terminal or PC connected to the network management port or port one. The range is 4-6 feet or up to 1000 feet with optional external repeater, not shown.

The network management port includes local and remote configuration commands. The Show Configuration Commands allow the system manager to view the configuration settings of both the local and remote multiplexers. Network management features include port and composite loopbacks, capture of a remote or local port, send a test message to an individual local or remote port, set multiplexer ID for node identification and a built-in "data line monitor" which allows the monitoring of the transmit or receive lines at the local multiplexer. A unique feature of the multiplexer is the Copy Command. This command allows a trainer at the host site to "copy" any local or remote port to view exactly what the user is entering.

Such multiplexing techniques allow for the circuitry (or an operator) to select which active devices should be utilized, or what pattern of active devices should be functioning. In some cases the identity or pattern of active devices being utilized is based upon whether (or the degree to which) the devices are in electrical or conformal contact with the tissue of interest. Thus, all embodiments herein are able to generate useful amounts of data even when all electronic devices are not in complete contact with the area of interest on the tissue, but may only be in partial contact. Furthermore, such multiplexing techniques enable selected portions of the circuitry to be activated. This is useful for targeted delivery of therapy, targeted sensing and power management as will be discussed below.

In a particular embodiment, the substrate can be deployed upon entry into the heart chamber. An array of sensors (contact, pressure, thermal, or acoustic) can inform the device operator once the surface of the balloon contacts the wall of the heart. The electrical properties of the tissue walls can be characterized with electrode sensors, which map conduction pathways to pinpoint the location(s) responsible for arrhythmias. Stimulating electrodes can comprised within therapeutic facility and thus be caused to ablate the abnormal regions, for example, with RF energy applied in the MHz regime. In addition to RF ablation, arrhythmic regions of the heart can be exposed to heat shock, microwave energy, ultrasound and/or laser ablation. The ability to localize the region of the heart effectively using mapping, such as three dimensional mapping, minimizes the need for multiple catheters and optimizes power use, since electrodes can be in positioned in direct contact with the tissue and because electrical current can be passed through the tissue only in the specific regions of the heart deemed to require treatment by the device operator. Further details are discussed below.

Figure 41A:
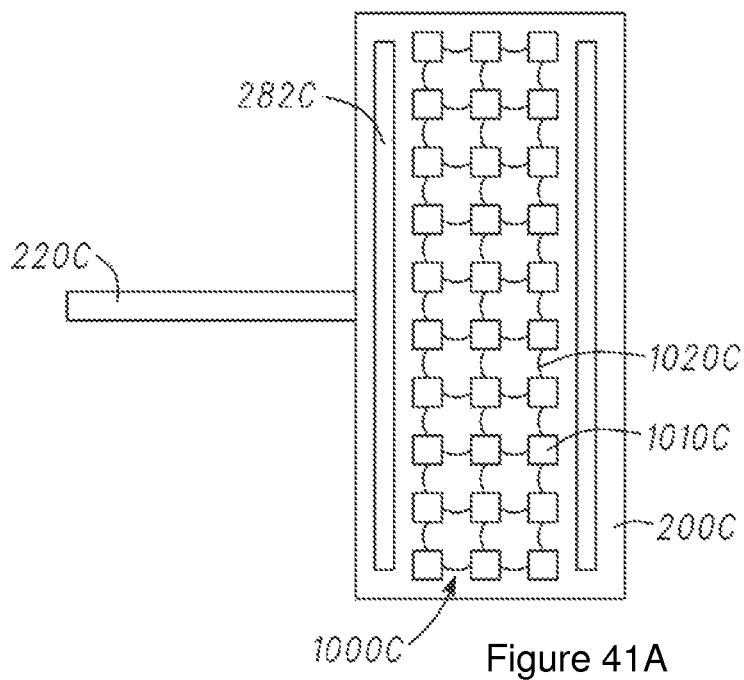
FIGS. 41A and 41B depict an embodiment of the invention where the substrate is furled.
Figure 41B:
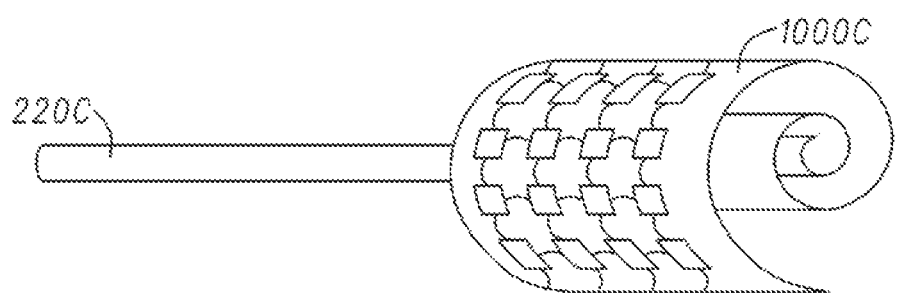

FIGS. 41A and 41B show an embodiment of the invention wherein the substrate is two-dimensional, is inserted via a catheter deliver system, but is unfurled or unrolled upon deployment rather than inflated. Other embodiments of deployment are amply described herein and below. As can be seen in the figures, stretchable circuitry 1000C is disposed on substrate 200C. As with many of the embodiments described above and herein, circuitry 1000C comprises arrays of devices 1010C connected by interconnects or bridges 1020C. FIG. 41A shows such an embodiment in its undeployed state, while FIG. 41B shows the device in its furled state, which is the state it must be in for delivery via a catheter delivery device.

Figure 42A:
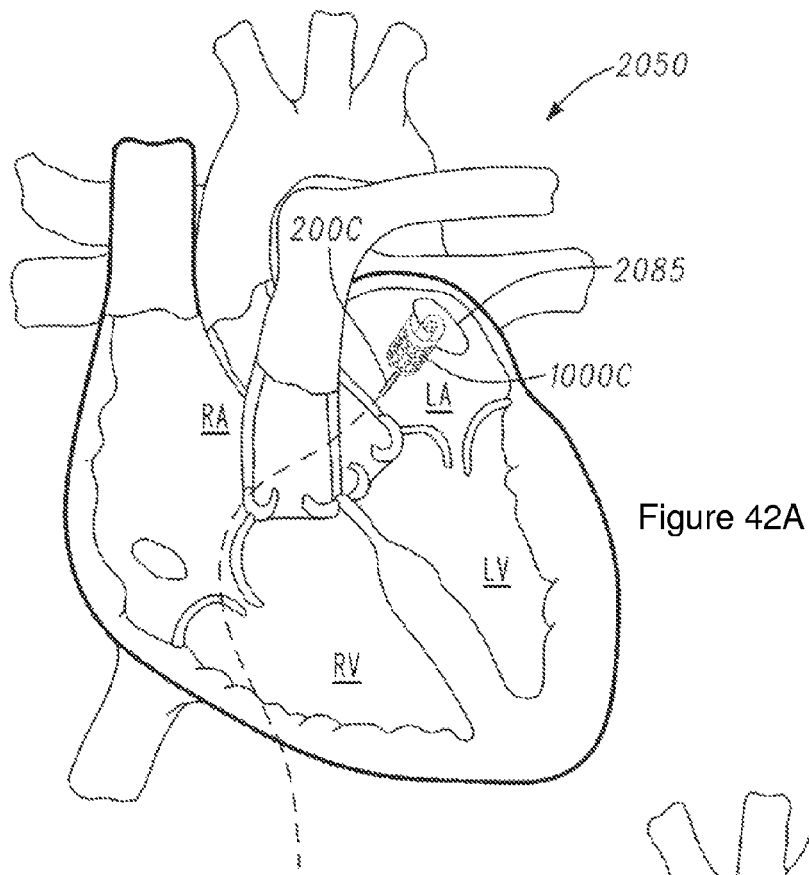
FIGS. 42A and 42B depict the device in FIGS. 41A and 41B being deployed in the left atrium of a subject's heart.
Figure 42B:
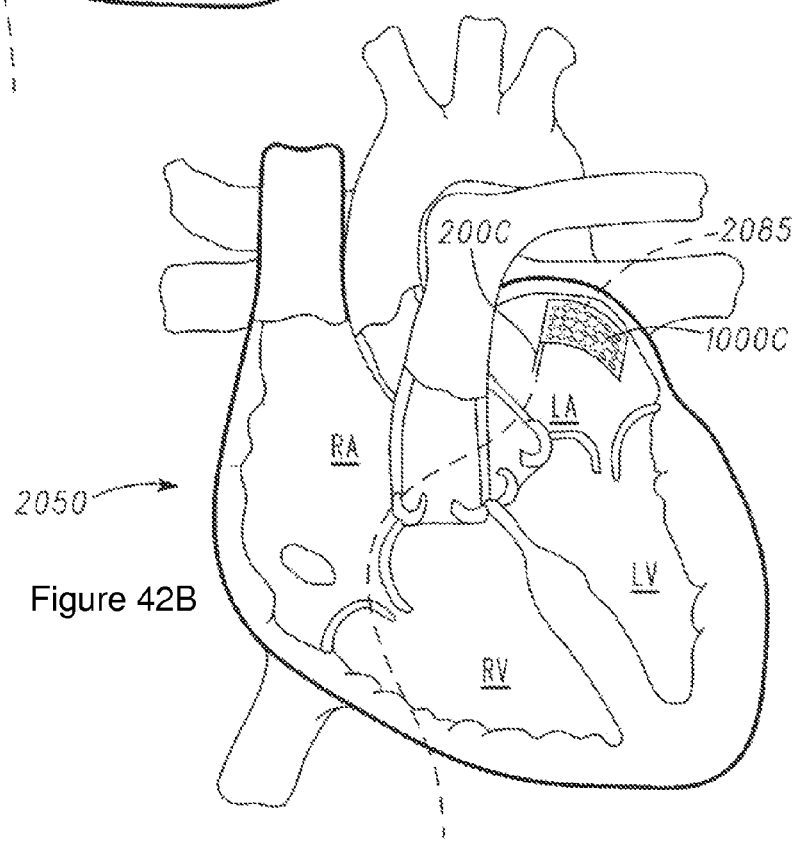

FIG. 42A depicts the embodiment shown in FIGS. 41A and 41B being deployed in the heart 2050. All four chambers of the heart are shown and are depicted and LA for left atrium, RA for right atrium, RV for right ventricle, and LV for left ventricle. The heart 2050 and its chambers are so indicated on FIGS. 41A, 41B, 42A, 42B, 43A, 43B, 44B, and 44C. As shown in FIG. 42A and FIG. 42B, the furled device is placed into the target region within the internal chambers of the heart via catheter delivery system. In embodiments, this catheter enters the left atrium via a trans-septal puncture, which is not explicitly depicted in the figures. As shown in FIG. 42 B, the substrate 220 is unfurled and thus deployed and thus operated in any of the manners described herein.

Figure 43A:
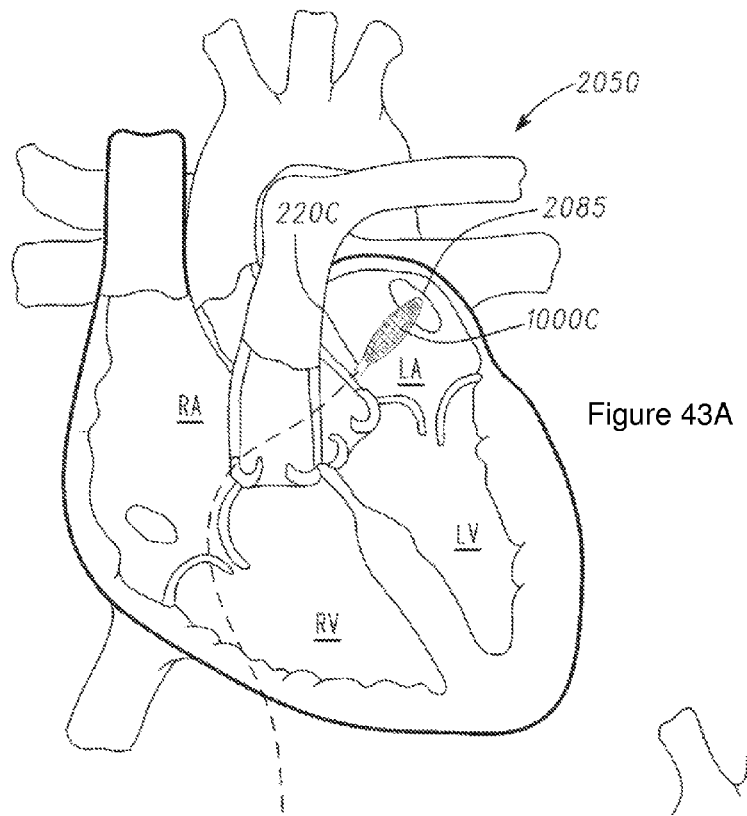
FIGS. 43A and 43B depicts an embodiment of the invention being deployed in the left atrium of a subject's heart, wherein the substrate is inflatable.
Figure 43B:
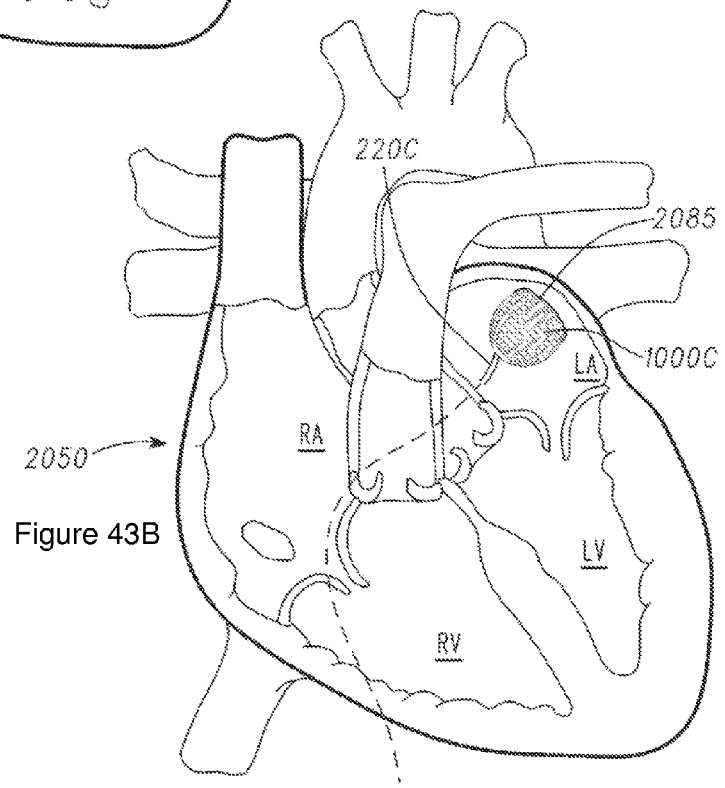

FIGS. 43A and 43B show deployment in the heart in embodiments where the substrate is an inflatable body, such as a catheter balloon. Deployment may comprise conformally contacting or partially conformally contacting a surface of the heart with the stretchable circuitry 1000C. In embodiments, the circuitry 1000C comprises sensors 1100 to generate electrical measurements at multiple contact points on non-uniform surface contours of the heart. Circuitry 1000C may also comprise pressure or contact sensors to determine the degree of contact with the tissue of interest, or which portions of the device including circuitry and therapeutic facility elements thereof, that are in contact with the tissue of interest. In FIG. 43B, the device is deployed in the ostium 2085 of the pulmonary vein to circumferentially isolate the ostium. Once deployed, the processing facility 1200 or 1200A processes the transmitted signals and produces output, which in embodiments may comprise a map, of the surface of the tissue of interest, the electrical conductivity of the tissue of interest, or the thermal properties of the tissue of interest. In embodiments, the processing facility 1200 of the invention generates a map in part by taking as input of electrical conduction activity within the heart.

As referred to above, in embodiments, a contact sensor (including thermal contact sensor or pressure sensor) generates data used by processing facility to determine force per unit area applied to the ostium 2085 of the pulmonary vein. Such information may be used to determine whether the inflatable body, i.e., cryo-balloon, has occluded the ostium 2085 prior to or during the procedure. The determination of occlusion via contact sensors is a significant advancement to prior methods. Specifically, it eliminates or reduces the need for injectable fluoroscopic dye to determine whether occlusion has occurred. To elaborate, it is often the case during ablative procedures that the clinician must determine whether and to what extent the balloon surface is in contact with the ostium and/or pulmonary vein, and whether and to what extent the ostium or pulmonary vein is occluded prior to and during the delivery of ablative therapy in order to ensure that the tissue of interest is fully ablated. Partial occlusion is undesirable, as it may result in less-than-complete ablation. Such is particularly the case during cryo-ablation procedures.

In practice, the clinician typically views a two-dimensional representation of the ablative device in the heart. (e.g., via x-ray angiography). Such two-dimensional representations are often insufficient for determining whether the ostium or pulmonary vein is occluded. Thus, the dye is often injected upstream from the site. If the dye does not enter the heart, then occlusion has occurred and the delivery of ablation may begin or continue. Co-locating contact sensors (pressure, thermal or otherwise) with the therapeutic facility (which may comprise any circuitry and elements to delivery ablation described herein) eliminates the needs for dyes and may reduce the time necessary to complete the procedure. Further, the invention has the ability to both deliver the ablative therapy, and with the same device during the same procedure to generate data regarding of the electrical conductivity of the site post-ablation to determine whether the ablation was a success.

Also, having all capabilities in one device eliminates the need to make more than one trans-septal puncture. For example, following each pulmonary vein isolation procedure, a mapping technique may assay the electrical activity from the left atrium to the pulmonary vein and vice versa, to assess isolation. Prior balloon ablation procedures, therefore, had to be coupled with mapping catheters (e.g., Lasso mapping catheters), which had to be inserted into the left atrium through a second trans-septal puncture.

Figure 44A:
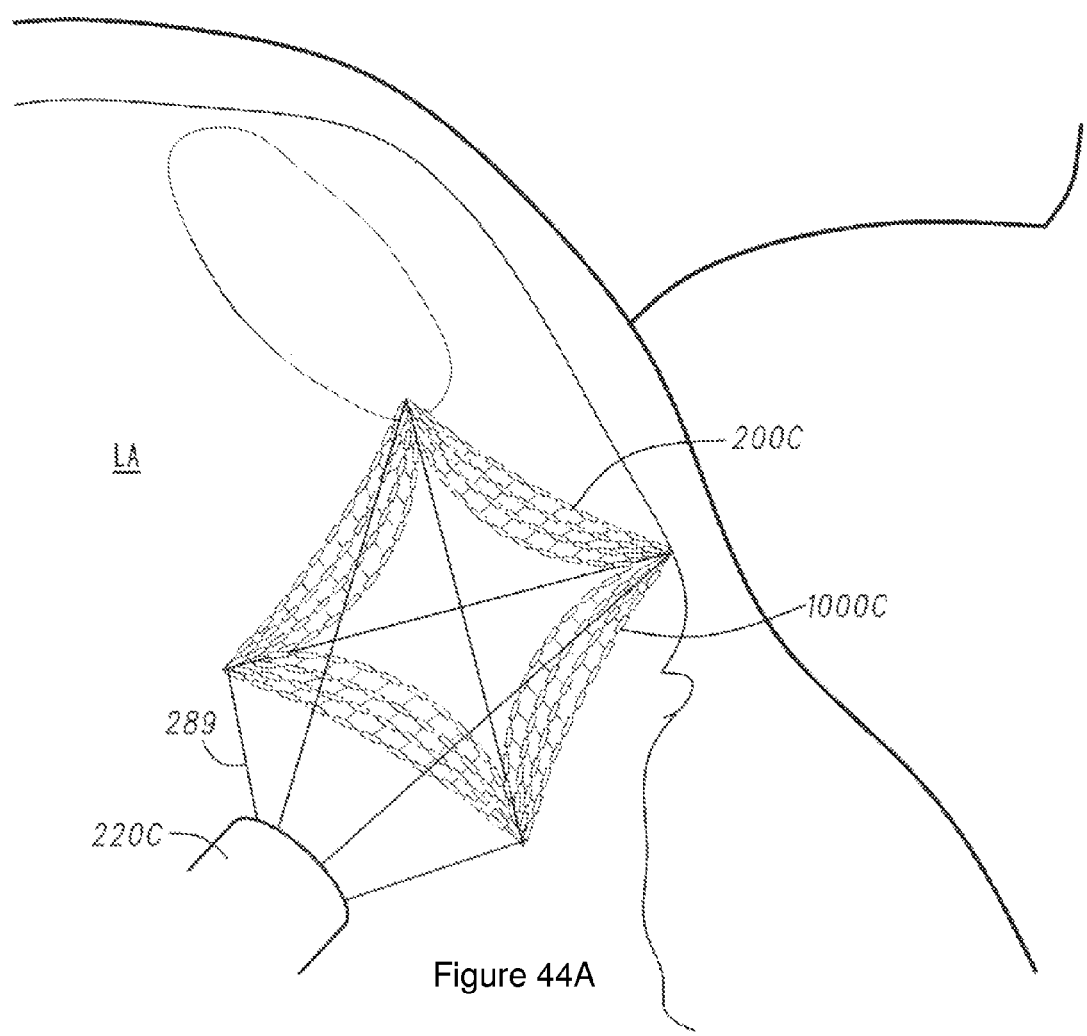
FIG. 44A shows a collapsible and expandable embodiment of the device being deployed in the heart of a subject.

FIG. 44A shows an alternate method of deployment. In this figure the device is deployed in the left atrium and, in doing so, the circuitry 1000C is brought into conformal contact with an internal surface of the left atrium. Catheter delivery system 220 includes an expandable nitonol assembly 289 having the substrate attached thereto. Once out of the catheter, the assembly 289 expands thus opening up the substrate 200C. The substrate may then be placed into position by the operator and the sensing, therapeutic, and/or mapping functions may commence.

Figure 44B:
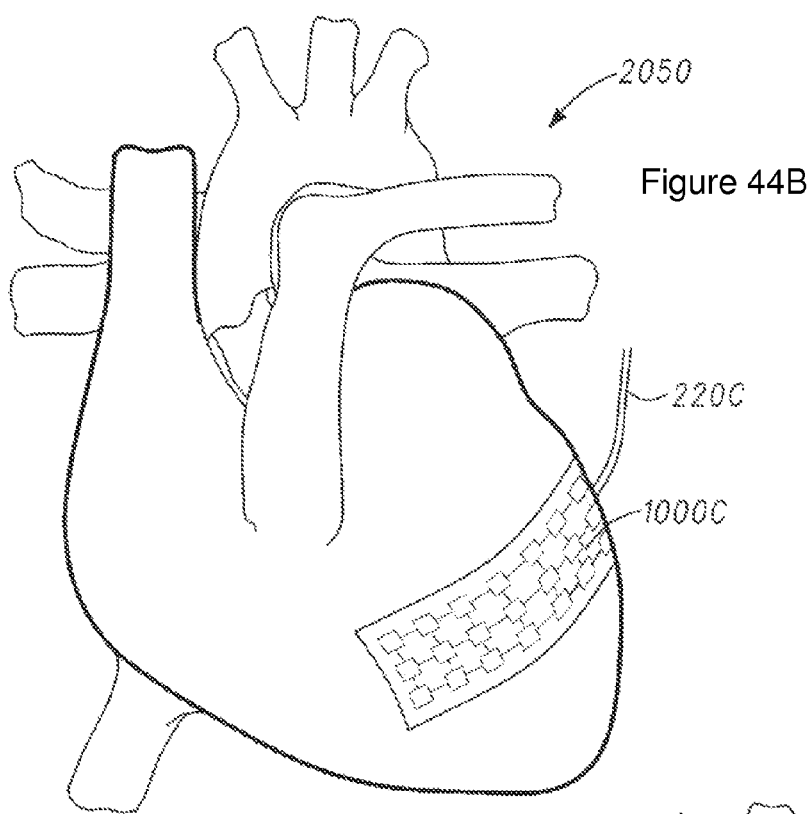
FIG. 44B depicts an example of the deployment of an epicardial embodiment of the device.
Figure 44C:
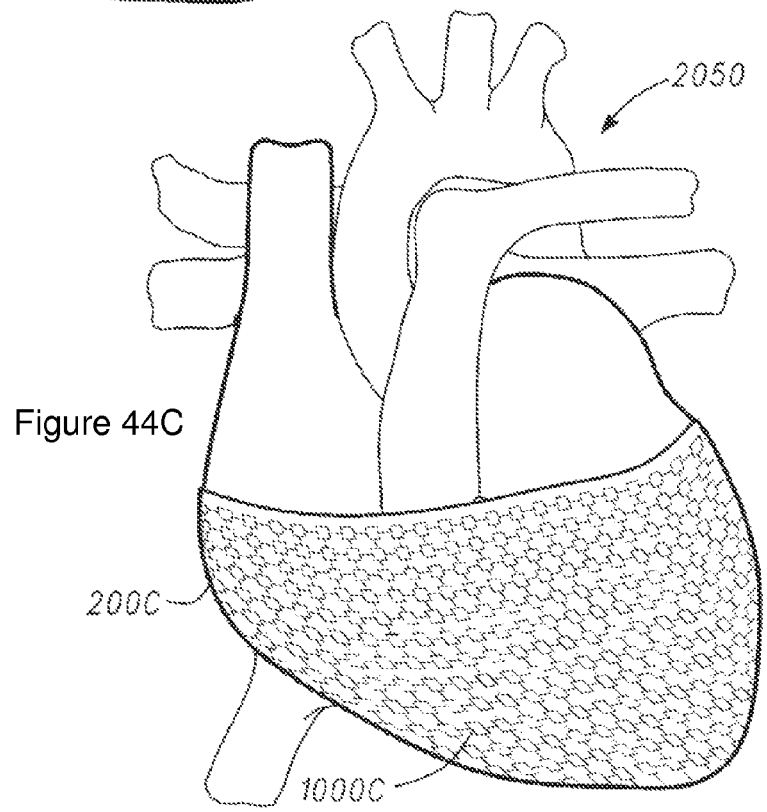
FIG. 44C depicts another example of the deployment of an epicardial embodiment of the device.

FIGS. 44B and 44C shows an epicardial-focused embodiment of the invention where a stretchable conformal substrate 200C is fitted with circuitry 1000C comprising (as which may be the case with any circuitry herein) an array of electrodes, sensors, effectors, other therapeutic facility components described herein, or combinations thereof. Such embodiments cover at least a portion the external surface of the heart. The electronic devices can be used for monitoring signals or stimulating the heart surface with pulses of electricity. In embodiments, this may be accomplished by using the sheet of electronics such as described above in connection with FIGS. 41A and 41B. The unrolling and rolling of this electronic sheet may be assisted by simple articulation components 282C that assist in placement of the sensor arrays onto the surface of the heart 2050. Delivery of this array is done by minimally invasive catheter intervention such as the subxiphoid percutaneous approach. Alternatively, the epicardial heart monitor may be deployed during a coronary artery bypass operation.

In other embodiments of this epicardial device comprises a stretchable substrate 200C comprising circuitry 1000C, wherein the substrate can be wrapped around the heart 2050 or portions thereof, as shown in FIGS. 44B and 44C. This device may again be delivered via the supxiphoid percutaneous non-invasive approach or during open chest surgery. The substrate 200 (which in embodiments is a sheath) may be employed as either a temporary or permanent structure to provide mechanical and electrical conditioning cardiac support for patients with severe heart complications. The sheath may also deliver therapies such as ablation as described herein. In the case where the sheath is left in the body after the procedure is finished, additional devices may be required for power, wireless information communication.

Similarly to the epicardial embodiment described above, the invention provides a minimally invasive way to get to detect relevant data regarding other organs or to deliver therapy thereto, including surface mapping and ablation. The conformable substrate having the circuitry described herein sheet could be inserted into the body and wrapped around the organ if interest or confirmed into a cavity or lumen of interest. Similarly, the device could be used around external body parts. Sensed data may comprise charge density as well as voltage at the surface. Thus, the device provides for a method to obtain data about organs and body parts without the use of invasive or penetrating sensing devices, electrodes, etc.

As should be understood because of the frequent references made herein, all of the embodiments of the present invention can be combined with other sensor array types embedded in a stretchable polymer substrate (e.g., balloon) to provide multiple sensing and therapeutic functionalities in parallel.

In embodiments, the therapeutic facility is configured in the ways described herein to provide ablative therapy, which may comprise an element capable of emitting various forms of electromagnetic radiation including microwave energy, thermal energy, laser, and RF. Thus the element may heat shock or utilize laser. In embodiments, laser ablation may be achieved by providing circuitry with high powered Laser diodes.

In other embodiments, the element comprises an ultrasound emitter to emit ultrasonic ablation. In such embodiments, the therapeutic facility (or element thereof) comprises an array of ultrasound transducers (e.g. piezoelectric crystals). Each island comprises a receiver that senses acoustic reflections generated by a source emitter that sends acoustic waves through the tissue at megahertz frequencies.

Still, in other embodiments, the device is configured to provide cryo-ablation. Further, by coupling delivery channels and micro-valves to the selectively operative circuitry in the manners described herein, cryo-ablation may be delivered by the therapeutic facility or selected portions thereof.

In ablative embodiments, the substrate may be stretchable as disclosed above and herein and provided with the stretchable circuitry described herein. Also as described herein, the stretchable circuitry is able to remain functional upon conforming to the surface of the tissue, which in embodiments for ablation, would comprise conformal contact with some surface of the heart or cardiovascular system, including the ostium of a pulmonary vein, any surface of a vein or artery, a septal wall of the heart, an atrial surface of a heart, or a ventricular surface of a heart.

In embodiments, processing facility generates or is in communication with an interface which is programmed to accept commands from an operator. The therapeutic facility is configured to activate upon receipt of such commands, and thus to deliver the ablative therapy, which for example may be the activation of the element described above.

In embodiments, the generated map or the sensed data can be used by the device operator to detect abnormal properties such as an abnormal conduction pathway in the heart or an arrhythmic region of the cardiac tissue. In embodiments, once an abnormal (for example, arrhythmic) region is located and characterized, the device operator may provide a command via the interface to activate a selected array of stimulating electrodes (comprised within circuitry 1000C) in a localized manner in the region of the abnormality. As such, more accurate and controlled ablation may be effected.

Figure 44D:
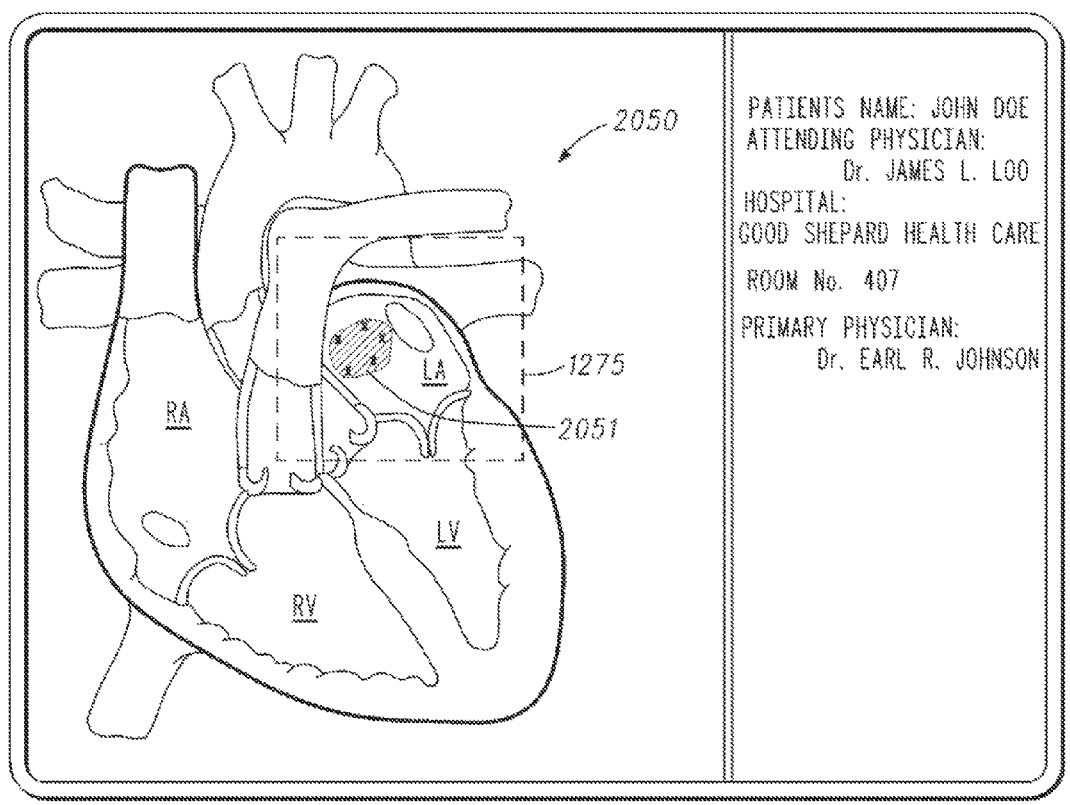
FIG. 44D depicts an embodiment of the invention having in interface to show abnormal activity and/or to suggest therapeutic activity.

As shown in FIG. 44D (and generally in FIG. 1C), after deployment and activation of any of the devices disclosed herein, the processing facility is programmed to generate a map of an abnormality. FIG. 44D shows the map displayed on an output device, which in this case is a display coupled to the device. Patient data is shown on the right. In embodiments, the map may be based on any of the sensors herein including electrical conductance, and to cause the output facility to display it. The region of the detected abnormality is shown as 2051. In other embodiments, processing facility is programmed to generate suggestions on which areas of the tissue to delivery the therapy based data related to the electrical conductance of the tissue including any abnormality or degree of such abnormality (shown as X's in the 2051). For example, the processing facility may be programmed to graphically depict the areas of suggested ablation. The device operator may choose to follow the suggestion or may use interface to graphically select a modified area in which to deliver the therapy, the interface of which is shown as 1275 which comprises sizable window in which to fit the selected area of ablation.

Referring back to FIG. 1B for context, it is noted that in embodiments, the circuitry may comprise any of the pressure and/or contact sensors disclosed herein. In embodiments, a pressure measurement above a certain preset threshold value also can trigger the processing facility to activate the circuitry to commence with electrical recordings and/or electrical adjacent to the given pressure sensor. Once deployed, such sensor arrays can sense the presence and mechanical properties of the tissue of interest.

In embodiments, such sensors can also be by processing facility to generate a map of the contour of the heart or electrical conduction pathways and provide feedback to the device operator. Such feedback may be used to provide guidance with respect to where to deliver the ablative therapy and also when to end ablation once the conduction abnormalities are corrected, for example if electrodes show normal pattern of electrical signals (or absence of electrical signals) post ablation, then the process may be deemed a success.

In embodiments, the pressure or contact sensors generate data that can be used by the processing facility to indicate that the circuitry is in contact with the tissue of interest, and if so what portions of the circuitry are in contact with the tissue. Occlusion may be determined this way as discussed above. As mentioned above contact sensors can generate data used by processing facility to identify when occlusion of a vein occurs (which is relevant during certain procedures) without echocardiography or dye injection. As such, the invention reduces side effects which may be caused by dyes and also may minimize the number of catheters that must be used in any given procedure.

Data regarding whether the device is in contact with the tissue of interest and to what degree is an important advancement which increases the likelihood that the ablative therapy will be more effectively and accurately delivered, and that the results thereof can be more accurately measured. In embodiments, temperature sensors and/or acoustic sensors may be used to provide such data of contact regarding contact. For example, the contact sensor (for example the temperature sensor) may indicate that said circuitry comprising the therapeutic facility, or portions thereof, are in contact with the area of interest. In this way, the circuitry manages power usage because it allows logic or an operator to selectively activate the circuitry (therapeutic facility, sensors, or both) based on whether the circuitry or the relevant portion thereof is in contact with the area of interest.

In embodiments where the contact sensor generates data of the mechanical properties of said tissue, processing facility 1200 or 1200A can be programmed to determine parameters such as perforation risk from such data. Further, in such embodiments, contact sensors and/or acoustic sensors generate data that processing facility may process to determine areas of the tissue that should be avoided during the delivery of therapy. Such areas may include veins and arteries during an ablative process.

Further, contact pressure (or force) of the ablation tip is a crucial factor that determines the lesion size created by the ablation. This contact pressure is critical to the formation of the lesion in cryoablation (cooled ablation) and RF ablation (heat induced ablation). If the contact pressure is too low, the ablation procedure may require excessive time to complete. Conversely, if the contact pressure is too high, there may be an increased perforation risk.

Using stretchable circuitry described herein, pressure/contact sensors may be incorporated onto the surface of substrates to measure contact forces applied to tissue to which therapy, e.g., ablation, is being delivered. Thermal sensors may be arrayed on the surface of the substrate, when only contact (not force) determination is required. Such contact sensors, preferably pressure, generate data of lesion depth (for example, 1.5 to 3 mm) based on contact force (for example, 1-50 g of pressure). The determination of lesion depth improves efficacy and safety.

The present invention device can rapidly pinpoint the region of the heart affected by arrhythmia. Conventional ablation catheters with linear arrays of electrodes typically require maneuvering of the distal tip of the catheter to locate the tissue area to be ablated. This feature of linear electrodes can require significantly more time than what is required for the present invention.

Another aspect of the invention regarding power management which relates to all embodiments disclosed herein, involves the use of CMOS-based components. CMOS circuits traditionally have minimal static power dissipation, which can help maximize the density of sensors and/or therapeutic facility on the substrate and optimize the amount of current being applied to the circuitry.

In another embodiment of the invention, the circuitry comprises ultrasound emitters and receivers to produce a lateral deep tissue image of the heart tissue and at high enough energies, to cause ablation.

In other embodiments wherein the therapeutic facility is configured to deliver ablative therapy, the above techniques may be deployed in/on the a subject's urethra. Mapping and/or ablation sheets/balloons may be inserted through the urethra and into the bladder volume via catheter for the treatment of incontinence, bladder control, and could be dually used to monitor health—pH balance, bacterial infections.

The delivery of therapy via therapeutic facility may involving configuring the device to deliver coolant. In embodiments, coolant may be delivered via a dedicated lumen in a catheter delivery system. An example of a known coolant for this purpose is nitrous oxide. Anti-freeze material may also be used to control or prevent freezing of the coolant inside the catheter or the substrate, which in this setting is typically a catheter balloon having a network channels herein which are in embodiments selectively accessed by selectively actuating valves such as the MEMS valves discussed in connection with embodiments below and with reference to FIG. 49. Channels in the substrate may be the micro-fluidic channels including but not limited to those which have been described above. All selective actuation of portions of the circuitry, nodes, etc. described herein apply to this selective actuation. The embodiments described above in connection with mapping and contact sensing improve efficacy of such coolant ablation (and all deliveries of therapy herein) by generating a map in the manners provided above. The map or data generated by the device may be used to determine the correct placement of the substrate. For example, electrodes and pressure sensors on the substrate, i.e., balloon catheter are used for mapping of the pulmonary vein and to achieve correct placement of the catheter (as opposed to the use of contrast agents). When the balloon catheter is positioned in the ostium of the pulmonary vein, the coolant may be delivered to the entire balloon where it is can ablate tissue. This method results in a complete ablation of the area where the balloon is in contact with the tissue. If selective ablation is desired, the coolant may be delivered to specific channels/regions in the balloon by activating so by accessing selected channels in the substrate, via embodiment, MEMS valves operatively coupled to the processing facility which is programmed to actuate said valves based on a command from a device operator, or in closed-loop systems based on data generated by the processor regarding which area to activate. A simple algorithm that the processing facility might employ is to determine which areas of the device are in contact, and to activate direct ablation to those areas. Another simple algorithm could be determine lesion depth and location relative to the device, and if lesion depth is less than preselected desired amount, continue to direct ablation to that area.

Cooling is also useful in other contexts and is thus not limited to ablation. Substrate outfitted with circuitry so-programmed may effect local cooling techniques, which again, may include the use of the micro-fluidic channels (such as those disclosed herein) to deliver lower temperature fluids to a site with an elevated thermal profile. In embodiments, the micro-fluidic channels are selectively accessed as described above and herein. In this manner, sheets of electronics in contact with tissue and organs can deliver therapeutic cooling to surfaces of organs (e.g., kidneys, brain, etc.) in thermal contact with the device. Such applications may be particularly useful in a first-response or emergency-care setting.

Referring back to FIG. 1A, another embodiment of the present invention involves a substrate 200 (denoted as 200N with reference to certain embodiments below) which is, or which comprises, a prosthetic device which can be inserted by means of a small opening, between severed ends of a nerve bundle. The external surface of the prosthetic device is provided with circuitry according to the disclosure herein wherein the circuitry may comprise microelectrodes coupled with amplification and stimulating circuitry.

The prosthetic device can be stretched, inflated or otherwise expanded to conform to the shape of the nerve bundles. This expansion may facilitate the orientation of microelectrodes, strategically positioned on the device, in such a manner as to bridge gaps in nerve bundles. Moreover, circuitry (and in embodiments therapeutic facility 1700) may selectively create connections between a plurality of nerves with the help of onboard logic components or by manual input from an operator utilizing an external device interfaced to the circuitry in the manners herein described. The execution of these actions may occur without movement of electrodes or further physical intervention.

The benefits of this particular embodiment include the ability to electrically reconnect many individual nerves without the need to manipulate them directly, reduce risk of aggravation to nerve damage by using a minimally invasive procedure and its ability subsequently "rewire" the connections one or more times without further surgical procedure. Additionally, this embodiment has the advantage of employing signal amplification and conditioning to adapt the input and output of each "reconnection" to the characteristics and function of a specific nerve fiber.

In this embodiment, circuitry is fabricated according to the methods described above. It should be noted that like other embodiments described herein, devices can be laid out in a device "island" arrangement. The devices are ~50 μm×50 μm2 squares, most of which accommodate one or more components connected to a buffer and also to an amplifier. Some devices accommodate active matrix switches and A/D converters, and some islands accommodate logic circuitry capable of reading in digital signals and processing them, and are capable of outputting data or storing data in memory cells. Circuitry may also contain device components which comprise metal contact pads. The circuits on devices are configured and designed such that preferably only about one, but not more than about 100 electrical interconnections are required between any two device islands or devices.

In embodiments, substrate comprises an elastomeric vessel (which is also referred to herein as an "inflatable body"). In certain embodiments such substrate is in the shape of a disk, said vessel covered with flexible and/or stretchable circuits described herein and having a multitude of electrodes. The disk can be deformed to enable its passage through a small opening in a "deflated" configuration and subsequent deployment in the gap between severed or damaged nerve bundles. Inflation with a viscous fluid is preferable, but it should be clear that a variety of gases, fluids or gels may be employed. According to the methods described herein, the flexible and/or stretchable circuitry is sealed with the miniature electrodes exposed so as to enable them to interact with the surrounding tissue. Each electrode can serve as either a sensing electrode or a stimulating electrode (also referred to herein as "effectors" and in embodiments considered to be comprised with the therapeutic facility 1700), and is connected to either a sensing or stimulation amplifier depending on device configuration. Signals are routed from sensing electrodes through signal processing circuitry to stimulation electrodes. In this embodiment, any electrode can act as a stimulating or a sensing electrode, depending on the dynamic configuration in effect at the time. Such electrodes may generate data while in electrical contact and/or direct physical contact. "Electrical contact" in meant to encompass situations where the electrodes are generating data regarding a tissue of interest while not necessarily being in direct physical contact. It should be noted that, "functional contact" or "sensing contact" is similarly meant to encompass situations where the sensing devices are generating data regarding a tissue of interest while not necessarily being in direct physical contact.

Figure 45:
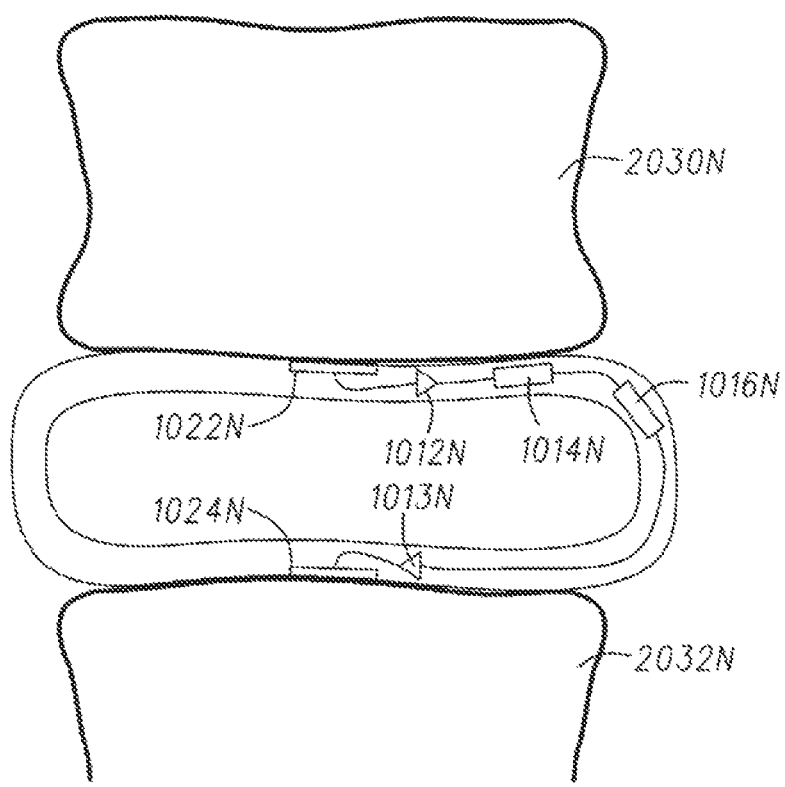
FIG. 45 is a schematic depiction of an embodiment of the invention involving a nerve prosthesis.
Figure 46:
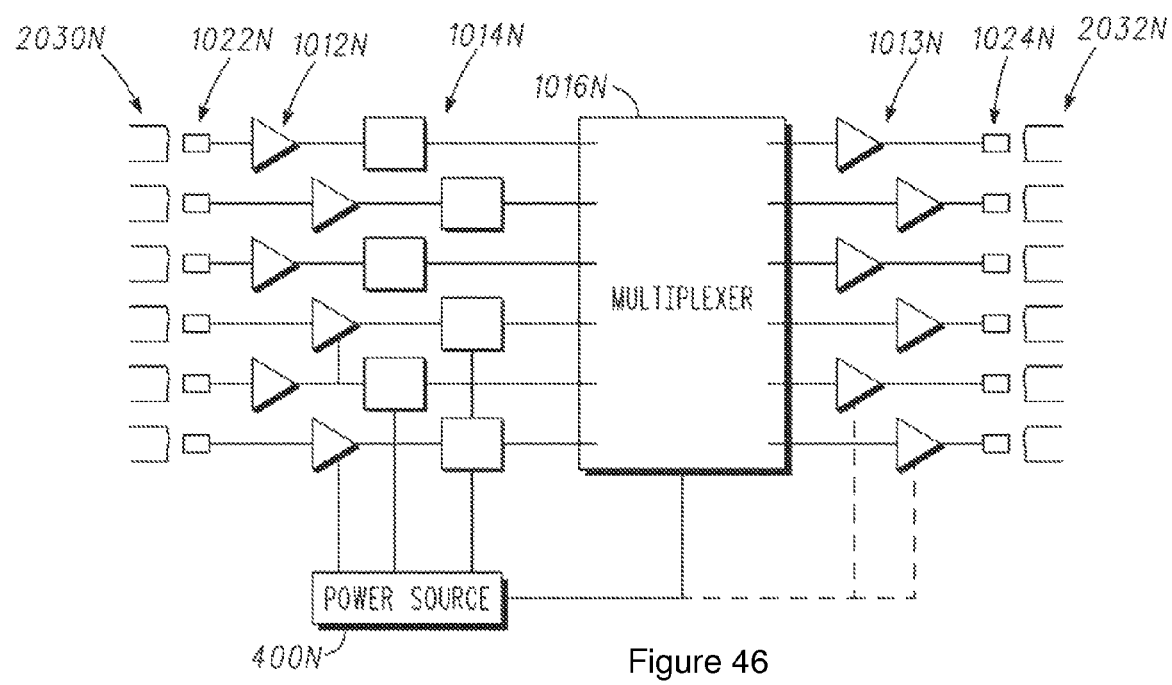
FIG. 46 is a circuit diagram for an embodiment of the invention.

FIG. 45 shows the path of a single nerve pulse in an exemplary embodiment of the invention. Electrode 1022N is in contact with nerve ending 2030N at a given location on the surface of the device. Electrical activity affects the current or potential at the electrode and is amplified by the sensing amplifier 1012N and then optionally undergoes further signal conditioning by block 1014N. From there, the electrical signal flows to the multiplexer 1016N which is configured to match nerve-signal sources and destinations in a way most beneficial to clinically desirable outcomes. The multiplexer 1016N dispatches the signal to the appropriate location on the other side of the device, where it is again amplified by the stimulation amplifier 1013N and finally effects nerve activity of nerve ending 2032 through electrode 1024N. FIG. 46 shows a circuit diagram showing multiple channels for the embodiment just described, Preferred embodiments contain thousands of such paths, enabling the interconnection of many nerves across a nerve gap in a flexible/configurable manner. Notably, the connection between two ends is not determined by the position of the device or at the time of implantation, it can be altered during the procedure or at any time thereafter by altering the dimensions of the invention. Among the reasons for altering the routing of the nerve signals would be observations about mappings of the various nerves, progress of the patient's recovery or effects of neuro-plasticity, or shifts in the relative positions of electrode and tissue in the course of motion or physiological processes. One automated means of configuring the apparatus is as follows.

Figure 47:
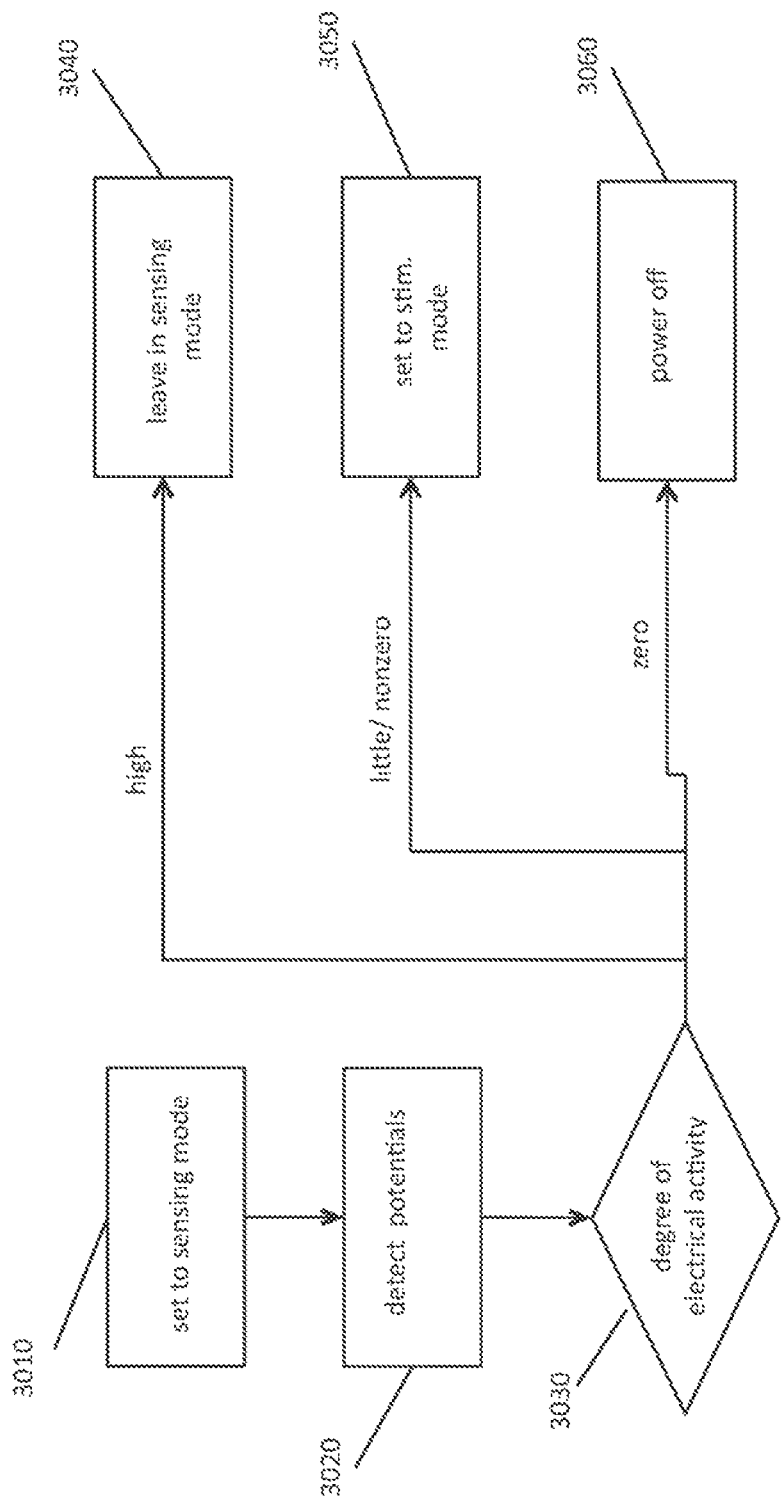
FIG. 47 depicts a process for operating an array of electronic devices according to an embodiment of the present invention.

As shown in FIG. 47, on initial deployment, all electrodes and associated amplifiers are set to be in sensing mode 3010. Electrodes then detect data of the potentials 3020. Electrodes are individually and collectivity affected by the activity of the nerves next to them. These are then amplified and processed (by any applicable processing facility described herein) to determine the presence or degree of electrical activity 3030, which is then used to configure the channels in the following manner: as shown in step, 3040 electrodes those regions with high electrical activity are left in sensing mode. Step 3050 shows that electrodes in regions with less, but non-zero, activity are switched to stimulation mode. In step 3060, electrodes in regions with no activity are turned off to conserve power and avoid interference. The full nature of the electrical signals, including their amplitude and frequency, are optionally utilized by this embodiment to deduce the original anatomical function of the nerve tissue it is contacting.

In embodiments, circuitry makes measurements of conductivity between electrodes. These measurements correlate with the electrical activity of physiological structures and hence can be used by circuitry or external processing facility 1200A to create a contour map of conductivity. In embodiments, such map can be used to enhance the configurations of the electrodes and multiplexing strategy.

As mentioned elsewhere herein, sensors can also include temperature or pH sensors or orientation sensors, and the measurements obtained from them used to improve the connections.

In other embodiments, the device does not simply provide one-to-one correspondence of electrodes. Stimulation of a given output electrode can be based on signals from more than one sensor and/or more than one input (sensing) electrode, or the stimulation of many electrodes based in signal from just one input electrode.

After initial configuration, the disclosed invention can be reconfigured one or more times thereafter, by establishing a wireless control link to the device from outside of the body (in the manners described herein) and using additional information to make decisions about the best configuration. For example, the clinician can communicate with the patient, asking him or her to attempt to move certain muscles, or to report absence or presence of certain sensations. Since as mentioned above, the substrate is biocompatible, the reconfigurations can be done after a surgical incision has successfully healed and without anesthesia or further trauma to the patient, enabling the connections between nerves to be slowly optimized for maximum benefit over a period of time. The benefit of the present invention is that these adjustments do not require any physical or surgical manipulation, thus avoiding further risks and suffering to the patient. Furthermore, subsequent configurations can be integrated into a comprehensive rehabilitation program.

The circuitry is distributed throughout substrate, which provides a high density of electrodes while allowing the invention to be realized in a variety of sizes and shapes most advantageous to a specific anatomical location. The flexible/stretchable nature of the circuitry enables it to achieve—and maintain—close contact with irregular surfaces of transected nerve fibers, providing a significant advantage over electrode systems that have to be individually positioned or require nerves to be flat planar surfaces that are not usually found in nature. In addition to making initial contact possible without either explicit surgical placement (which would be impractical for thousands of individual nerves) or perfectly flat surfaces, the present invention has the benefit of maintaining contact (electrical or physical) with a large number of nerves despite physical movement, physiological processes (such as inflammation or scarring), or the passage of time, since a near-uniform pressure is applied to all of the electrodes by the fluid filling the apparatus.

Figure 48:
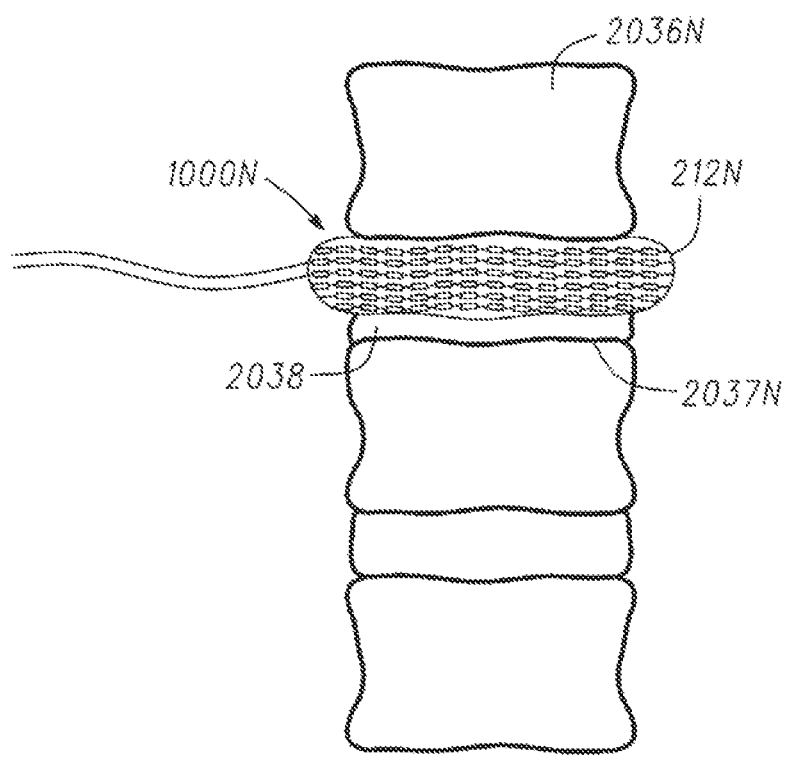
FIG. 48 depicts an embodiment of the invention involving a nerve prosthesis.

FIG. 48 shows the device implanted in the spine of a subject having nerve damage. 2036N and 2037N are vertebrate of a spine. Cartilaginous disc 2038N disc is also shown. Inflatable disk 212N having circuitry 1000N is shown being inserted into the area of damage. Once in place, disk 212N is inflated thus contacting the nerves as described above.

The embodiments described above may be provided on substrates that are biocompatible and thus may be implantable. Temporary-use embodiments are contemplated as well. In embodiments having particular relevance to the treatment of epilepsy, the substrate may be provided in the shapes and manners described above. Circuitry equipped with the sensing, effecting and therapeutic functionality described herein may be used to detect seizures. Sensors may identify a seizure by detecting a sudden increase in amplitude and change in frequency of electrical brain activity. Data may be tracked and stored in the manners provided herein to track data related to seizures. The device may also produce a map of the seizure activity in the manners described herein. The detected data, including maps, may be used to select an area to treat, for example, via a user interface provided to a device operator. However, closed-loop systems are contemplated as well, in which the processing facility is programmed to recognize abnormal electric activity and provide stimulation when necessary, for example by activating the effectors/stimulating electrodes on the devices in the manners described. In an embodiment, circuitry (i.e., therapeutic facility) can be configured to deliver a pattern of stimulation as follows: periodic pulsing of electrical currents (e.g. vagus nerve stimulation: 10-30 Hz, 1-5 mA, on/off 30 s/300 s; deep brain stimulation: 50-100 μs pulse width, 100-150 Hz and amplitudes of 1-10V) which are thought to disrupt abnormal electrical activity in the brain. A preferred embodiment comprises a substrate in the form of a conformal sheet may be delivered by minimally invasive means via a catheter deployed array of wires (e.g., nitinol material), onto the surface of the brain with an external connector to link with power and control systems. In embodiments, the sheet may have a rechargeable power storage unit and a built in microprocessor. The sheet may be cut and reshaped in the manners provided below to achieve its optimal size.

In should be noted that in all embodiments utilizing electrodes for stimulation may be both monopolar or bipolar. Monopolar electrodes create a high energy density at the electrode and a low density at an arbitrary grounding point. A current flows between these two points in an undefined path. With an electrode pair, the conduction path is well defined (between the 2 electrodes). As such, bipolar systems allows for more effective application of energy, for example, below the tissue surface due to its directional delivery design. Thus, in embodiments therapy can be delivered to a desired tissue depth.

It also should be noted that therapeutic facility may in the embodiments described immediately above and also throughout this disclosure, may be equipped to deliver photo therapy to photoactive neurons. For example, light activation of ion channels to control the firing of neurons can be used for therapeutic effects. The gene channelrhodopsin-2, is a light sensitive ion channel that when expressed in neurons in the brain, respond to blue light creating an action potential in the neurons. As such, the therapeutic facility may be equipped with LEDs (in stretchable configurations in embodiments) to deliver such therapy.

Figure 49:
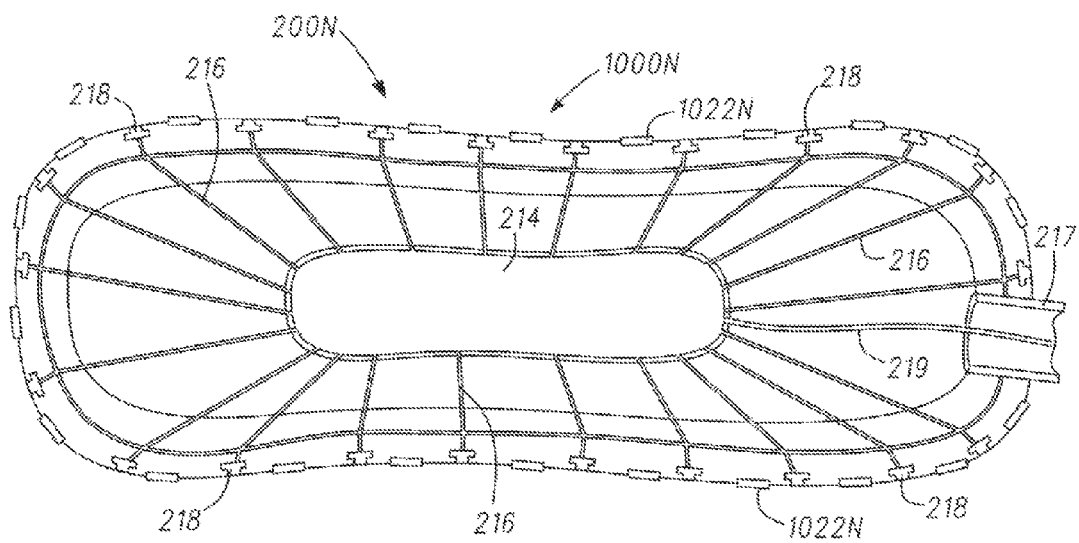
FIG. 49 depicts an embodiment of the invention having a reservoir for holding and delivering a therapeutic agent, along with valves controlled by the circuitry to deliver said therapeutic agent.

As described above, other embodiments could include a therapeutic facility (such as 1700 described in FIG. 1A) invention would also incorporate drug delivery capabilities alongside electrode arrays. FIG. 49 shows such an embodiment. Circuitry 1000N comprising electrodes 1022N, for example, is provided on the outside surface of disk 200N, which may or may not be inflatable. A drug reservoir 214N is provided which communicates with the surface of the disc 200N by way of channels 216N. At the end of the channels 216N are valves 218N which in embodiments are MEMS valves, which are connected to and controlled by circuitry 1000N which comprises the therapeutic facility 1700. Refill line 219N is connected to the reservoir which allows for the reservoir 214N to be refilled in embodiments. One benefit of such a capability is to deliver drugs to reduce rejection or scar formation at the interface between the tissue and the apparatus. The release of a drug can be controlled by means of the MEMS valve 218N and delivered only in areas where processing facility has determined, by being so configured, that previous measurements (such as temperature or conductivity) have indicated that it may be of greatest benefit. Other embodiments include individual cavities containing the drug, which when consumed necessitate the replacement of the device if further drug therapy is desired.

Such embodiments comprising a drug reservoir may comprise reservoirs which in turn may contain multiple, and in some cases different, drugs in each reservoir. The reservoirs can be viewed as separate nodes and selectively controlled in the manner described herein. As with other embodiments of the device, the drug reservoir may be part of a closed-loop which utilizes sensors to detect conditions in which delivery of a desired drug is advantageous. The advantage provided by the present invention is that the stretchable format will significantly improve the spatial resolution of drug delivery to highly localized regions.

The above reservoir/deliver embodiment may be used for the selective delivery of coolant, which is relevant to the cryo-ablation procedures described above.

In another embodiment of the invention, electrodes on substantially flat substrates, in embodiments, sheets that comprise stretchable and/or flexible electronics may deliver stimulation to the brain, patch of exterior skin, nerve bundles, internal organs, and the like. Higher density electrodes (such as <1 cm spacing) may be enabled by reducing wiring complexity, including communications facilities with each electrode or to groups of electrodes, by including amplification and multiplexing capabilities within array of electrodes, and the like.

Other embodiments of the invention, involve endoscopic imaging devices having improved design efficiencies in terms of power and volume. Embodiments of the present invention incorporate conformal, curvilinear electronic components for the purpose of volume reduction, imaging enhancement, and increased functionality.

It will be appreciated that the approach of the embodiment described below may be applied to conventional tubular endoscopy devices and capsule endoscopy devices, as well as any device utilizing the herein described curved focal plane arrays of photodetectors that are comprised in a CMOS imager. It should be noted that such curved focal plane arrays can be utilized in conjunction with any embodiment described herein and that all other embodiments described herein including those related to the circuitry including and the elements thereof are intended to be utilized as applicable in the endoscopy embodiment described below. Curved silicon optical sensor arrays have significant advantages over conventional planar arrays. These advantages include a reduced number of optical elements, reduced aberrations including astigmatism and coma, and increased off-axis brightness and sharpness.

In embodiments of the invention, an endoscopy device is fitted with a curvilinear array of sensors and/or transducers, e.g., on the exterior surface thereof, thereby reducing the required volume of the device. This approach is particularly advantageous in reducing the overall size of an endoscopy device, allowing integration of additional diagnostic and therapeutic and/or sensing functionality including any described herein an the following examples, ultrasound, pressure sensing, temperature sensing, pH, chemical sensing, targeted drug delivery, electrocautery, biopsy, laser, and heating), and increasing the allowable battery size. Increasing the power storage of a capsule endoscopy device can lead to improvements in image quality, image compression, transmission rate, number of images captured, and the intensity of illumination produced by the LEDs.

In embodiments of the invention, a capsule endoscopy device and its internal circuitry are both made flexible and/or stretchable from any of the materials described for substrates including other biocompatible materials apparent to those skilled in the art. Such a flexible/stretchable endoscopy device may have increased ease of motion along the GI tract and also increased viable volume. In other embodiments, the device may have a rigid capsule-like structure with electronics conformally fitted in the inner and/or outer shell of the capsule. The exposed surface—either a rigid ellipsoid shell or a flexible or stretchable layer—is fabricated from a material resistant to the harsh digestive environment that the endoscopy device will encounter, but which is also is biocompatible and harmless to the patient's internal anatomy. Other properties of biocompatibility of the outer surface are described herein.

The stretchable electronic components of the endoscopy device have been described herein in connection with the discussion of circuitry in all embodiments. In embodiments, circuitry comprises sensing and imaging arrays for monitoring features that are inside of bodily cavities and lumen such as the GI tract. As described above, the functionality may reside in circuitry comprising devices which may comprise device islands or vice verse. The islands house required circuitry and are interconnected mechanically and electronically via interconnects such as those described herein. The interconnects, in turn, preferentially absorb strain and thus channel destructive forces away from the device islands. They provide a mechanism by which the integrated circuits can stretch and flex when a force is applied. The device islands and interconnects may be integrated into the casing or encapsulating shell of the endoscopy device by transfer printing, as described below. Encapsulation of electronic devices and system/device interconnect integration can be performed at any of a number of stages in this process.

As with other embodiments described herein, the circuitry used in the electronic devices may comprise standard IC sensors, transducers, interconnects and computation/logic elements. In embodiments, electronic devices are typically made on a silicon-on-insulator (SOI) wafer in accordance with a circuit design implementing the desired functionality. Semiconductor devices may be processed on suitable carrier wafers which provide a top layer of ultrathin semiconductor supported by an easily removed layer (e.g. PMMA). These wafers are used to fabricate flex/stretch ICs by standard processes, with particular island and interconnect placement being tailored to the requirements of a particular application. "The devices of have utlrathin geometries that exhibit extreme levels of bendability. They are typically less than 10 µm in thickness.

The above discussions of fabrication of circuitry applies to endoscopy embodiments. However, the following discussion will describe a transfer step for embodiments related to endoscopy (but not necessarily limited thereto). In such embodiments, the circuitry is primarily used to enhance the imaging system of the device.

Imaging with a curved optical sensor array (instead of a planar array) is used in conjunction with a lens, illuminating LEDs, battery, computing unit, antenna and a radio transmitter. Wired telemetry is used for conventional tube endoscopy. A passive or active matrix focal plane array is fabricated using one of the stretchable processing techniques described above. The array includes single-crystal silicon photo-detectors and current-blocking p-n junction diodes. Images captured using the array are minimally processed by onboard computing and transmitted (wired or wireless) to an external receiver for further processing.

The focal plane array described below could be considered part of any imaging facility described above. The individual photo detectors may be networked via interconnect systems in accordance with the present invention. These devices are found on islands and are connected by interconnects such as those interconnects described herein. In embodiment, films of polyimide support certain regions and encapsulate the entire system. Such a focal plane array can thus be incorporated into the endoscopy device.

Figure 50:
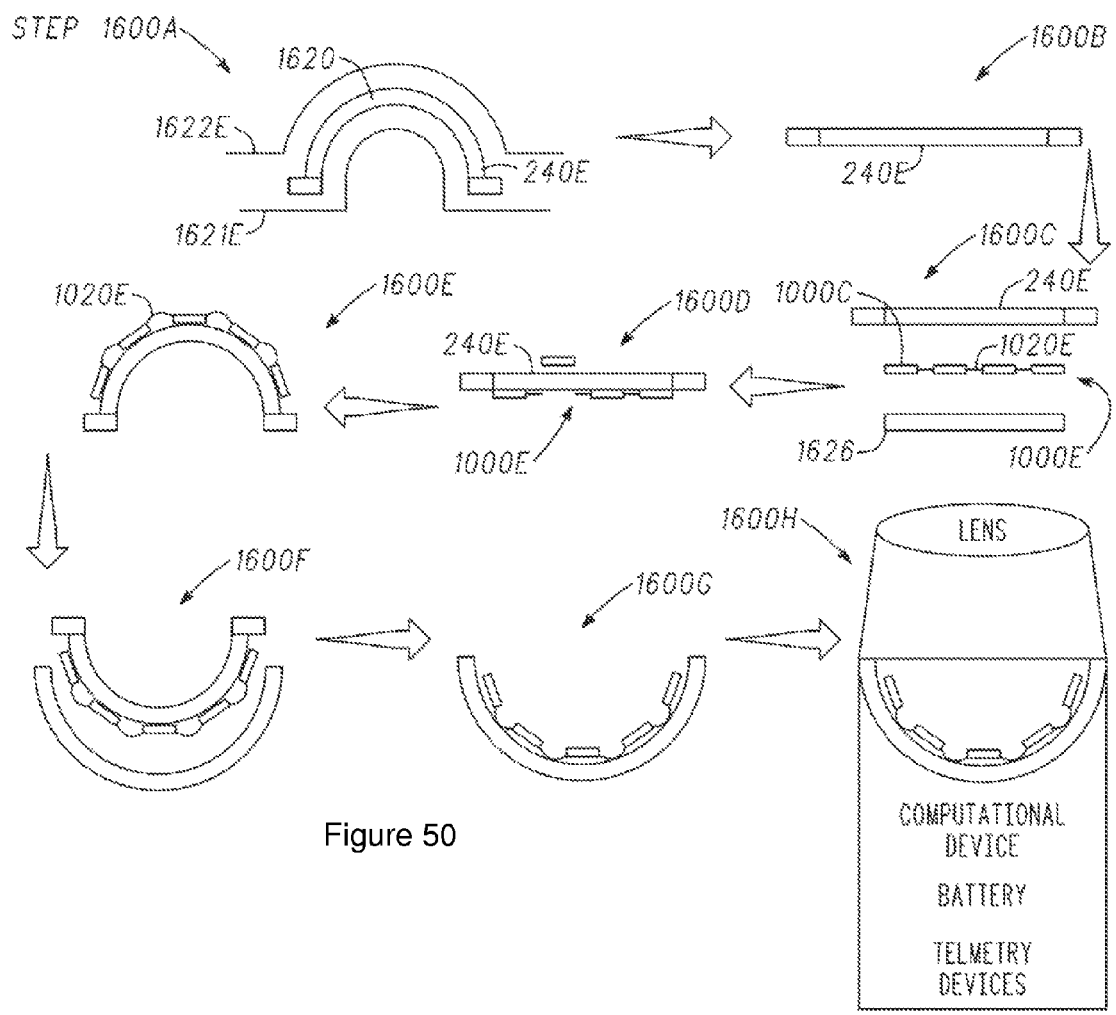
FIG. 50 depicts a process for assembling curvilinear circuitry according to an embodiment of the invention.

FIG. 50 illustrates the process of making a such focal plane array. The first step is fabricating the necessary circuitry 1000E, which in this embodiment is a focal plane array, is the creation of a suitable geometric transfer stamp to facilitate this process. In this embodiment, the circuitry is represented herein as 1000E (although it should be understood that is contemplated that this circuitry 1000E relates to and may be used with other circuitry embodiments described herein).

At Step 1600A, an appropriate stamp (also referred to as transfer element) 240E is created by casting and curing poly (dimethylsiloxane) (PDMS) in the gap between opposing convex and concave lenses with matching radii of curvature (1621E and 1622E respectively). The radius of curvature should reflect the optimal parabolic curvature useful for a non-coplanar imager. At step 1600B, the cured curved transfer element 240E (the removal of which from lenses stamping mechanism not shown) can be stretched using a specially designed mechanism which provides outward radial forces (in embodiments equal outward forces) along the rim of the stamp to create the planar pre-strained geometric transfer element. The transfer element should return to its initial size when relaxed. Transfer element 240E should also be large enough in its planar configuration to contact the entire area of electronic device islands on the donor substrate.

A component of the circuitry 1000E in this embodiment is the processed electronic devices joined by interconnects 1020E. At step 1600C, the circuitry 1000E is brought into contact with the planar transfer element 240E, which adheres to the former via sufficiently strong van der Waals interactions. The transfer element 240E is peeled back, thereby removing the focal plane array, i.e., circuitry 1000E, from its handle wafer 1626, shown at 1600D. After the focal plane array 1000E is removed from the handle wafer, the tension in the stamp is released and the contacting layers, i.e., the focal plane array and the stamp, both take initial geometric form of the stamp (shown at 1600E). The focal plane array 1000E compresses and the networked interconnects 1020E of the array buckle to accommodate the strain. The buckled focal plane array 1000E is then transferred to its final substrate (shown in steps 1600F-H) which has a matching radius of curvature and is also in communication with the battery, antenna and a radio transmitter via electrical contacts. This transfer occurs by contacting both surfaces and is aided by the use of a photocurable adhesive. The adhesive provides sufficient attraction such that when the PDMS stamp is removed, it releases the curvilinear array of photodetectors onto the imaging system port. The curved focal plane array is then connected to the rest of the imaging electronic components via electrode contact pads on the outer perimeter of the array.

Figure 51:
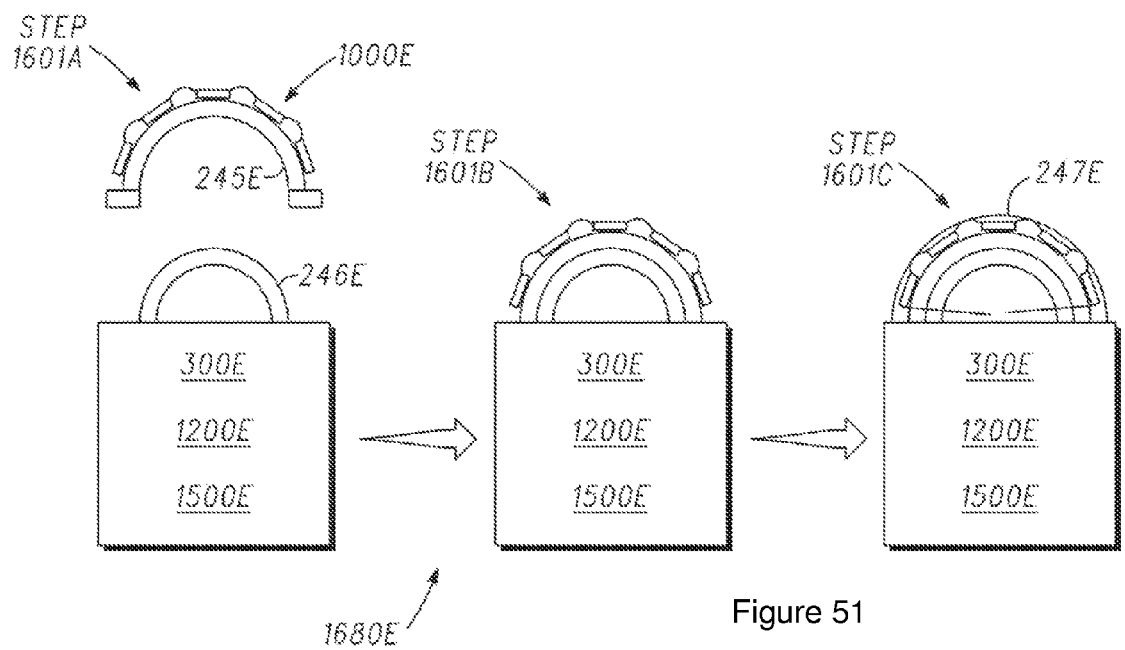
FIG. 51 depicts an example of a process for applying a curvilinear array of circuitry to an endoscopic device according to an embodiment of the invention.

In another embodiment shown in FIG. 51, and endoscopy device 1680E comprising power 300E in the form of a battery, processing facility 1200E, and data transmission facility 1500E is shown. Step 1601A shows convex focal plane array 1000E that is adhered to the outer shell of the endoscopy device 1680E by, for example, a geometric transfer stamp 245E. After lifting the focal plane array off the handle wafer with the planar pre-strained PDMS (as described in connection with previous FIG. 50), it can be relaxed and directly deposited onto the distal end of the endoscopy device 1680E, which is provided with a receiving substrate 246E having, for example, a photocurable adhesive. After deposition onto the endoscopy device 1680E (status shown as 1601B), electrical contacts are made from the array 1000E to the internal circuitry of the endoscopy device 1680E. At 1601C, all of the exposed circuitry can be sealed with a suitable polymer and/ or metal layer (e.g. parylene, polyurethane, platinum, gold) 247E.

Micro-lens arrays may be required for such optical array systems. However, with proper illumination and negligible distance between the optical array and the surface being imaged (e.g. near field imaging), this requirement may be nullified.

In yet another embodiment, a focal plane array, also referred to as circuitry 1000E (as described above) is conformally wrapped around an endoscopy device such that it points in an outward radial direction from the long axis of the device. This is achieved by completing the same planar stretchable processing steps mentioned above and transferring the circuit with a different specialized polymeric stamp. The transfer stamp may take the form of a planar rectangular strip. Each polymeric strip is pre-strained by thermal expansion (heat to around 160° C.) or by applying uniform radial strain. This pre-strained polymer is then positioned in direct contact with the processed focal array. The elastomer is subsequently peeled back to release the array from its handle wafer. The stamp is then relaxed via cooling to room temperature or gradual release of the mechanically induced strain. Release of this strain causes the elastomer to return to its initial shape, which in turn forces the device islands of the array to draw closer. In embodiments, the interconnects are forced to buckle, enabling stretching and bending characteristics. In embodiments, the area upon which the array is meant to adhere is pre-treated with a photo-curable adhesive. Alternatively, a layer of PDMS may be used to enhance adhesion.

Figure 52:
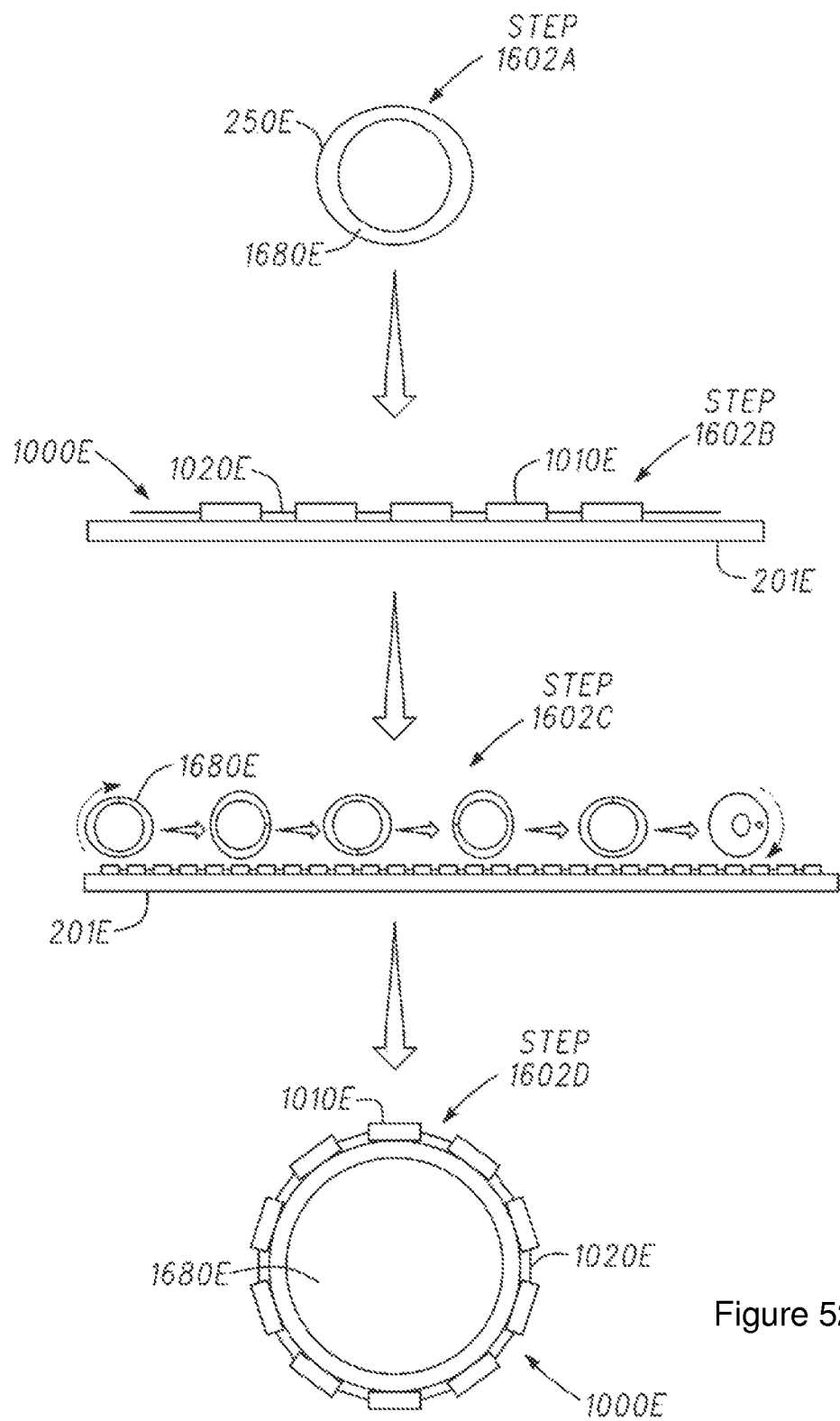
FIG. 52 depicts another example of a process for applying a curvilinear array of circuitry to an endoscopic device according to another embodiment of the invention.

FIG. 52 details an embodiment of the process for transferring circuitry to the endoscopy device. The transfer is achieved by stamping the planar array of device islands and interconnects onto a curvilinear surface such as an endoscopic device 1680E. 1602A shows the endoscopy device having a thin PDMS shell or adhesive outer layer 250E. 1602B shows the circuitry 1000E on a carrier substrate 201E. 1602C shows the step of rotating the endoscopic device 1680E around a single revolution over the substrate 201E containing planar array of device islands, the array of photodetectors and interconnects will preferentially adhere to the surface of the endoscopy device 1680E in a curvilinear manner as shown in Step 1602D.

In another embodiment, micro-lens arrays may be required for optimal focusing and image quality. However, with proper illumination and negligible distance between the optical array and the surface being imaged, this requirement may be nullified. In the case where micro-lens arrays are required, they may be created directly as the encapsulating layer of the photodetector arrays during stretchable processing. They may also be stamped on after the endoscopic devices are made. This optical array is then encapsulated and electronically integrated with the rest of the endoscopic device in the following manner: electronic devices which have been processed for stretching, can be picked up with a planar pre-strained PDMS stamp. The pre-strained PDMS stamp is then relaxed and brought into contact with the acceptor substrate for transfer printing. This acceptor surface may be the surface of the endoscopy device, said surface coated with a thin PDMS layer, or a separate thin appropriately shaped PDMS layer that may later be wrapped around the endoscope. In the case where the devices are facing outwards on the endoscopy device substrate, they may be encapsulated (while in their compressed state) with another layer of PDMS, or a liquid layer of PDMS followed by an upper layer of solid PDMS to make a fluid encapsulation. Other materials/methods may also be applied. In the case where the devices are facing outwards on the endoscopy device substrate, they may be electrically externally interfaced at conductive pads that should be designed to be located at a convenient location. Anisotropic conductive film (ACF) connectors can be used to interface to these conductive pads, by pressing and heating the film onto the pads.

In the case where the devices are fully encapsulated or facing inwards, they may be electrically externally interfaced by first removing part of the encapsulating polymer over the conductive pads through wet or dry chemical etching, or physical mechanical removal of material, including but not limited to drilling. At this point, the ACF may be incorporated. Alternatively, the stretchable electronics may be electrically interfaced to an ACF prior to the transfer or encapsulation process.

Figure 53:
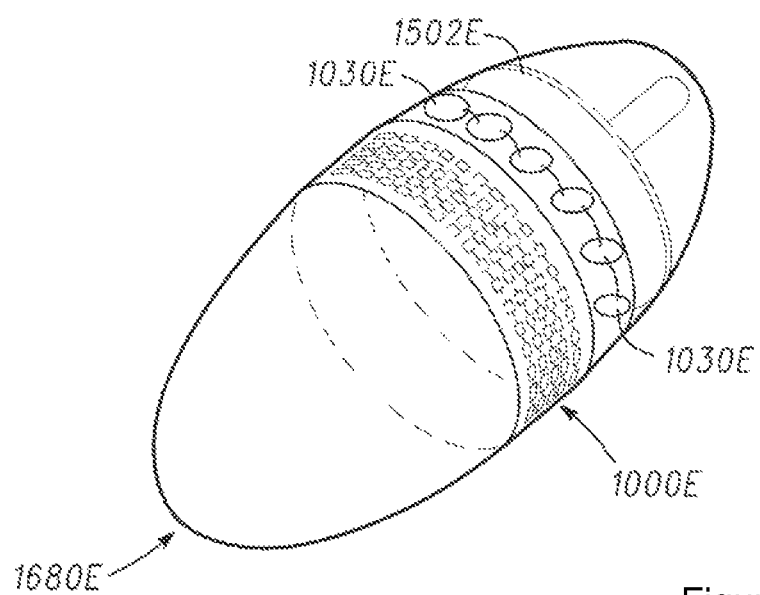
FIG. 53 depicts an embodiment of an endoscopic device according to the present invention.

In embodiments, circuitry 1000E may include a flexible LED array on the outer surface of the endoscopy device 1680E, as shown in FIG. 53. Such an array provides illumination required for optical image capture. A representative process for creating a flexible LED system is as follows:

LEDs are made from quantum well (QW) structures on a GaAs substrate. In between the GaAs substrate and the QW structure is an AlAs sacrificial layer. The QW structure is etched with reactive ion etching (RIE) to down to the sacrificial layer to form isolated square islands which may be in the range of, for example, 10-1000 μm on an edge. A partial release/undercut of the islands with HF etching is performed. Photoresist is spun onto the substrate and patterned to form squares around the corners of the islands, to serve as anchors. A full HF release etch is performed to free the islands from the GaAs bulk substrate; the photoresist anchors prevent the islands from floating away during etch, rinse and dry steps. An elastomeric stamp (for example PDMS) is used to pick up the islands and transfer them to another substrate. The transfer may be done in multiple steps, picking up a fraction of the GaAs islands at a time, to rearrange them geometrically. The substrate onto which the islands are transferred for further processing may be a layer of PET (polyethylene plastic) on a glass substrate that can be later peeled off, or a layer of polyimide on top of a PMMA (polymethylmethacrylate) sacrificial layer, or a layer of PDMS etc. Parts of the LED islands are then patterned and wet etched so that the bottom n-type contact is exposed; this may be done with, for example, a H3PO4+H2O2 combination. Parts of the islands are unetched so that the upper p-type material can be contacted electrically as well. Next, a planarization layer of polyimide is spun on, patterned so that vias extend down to the p and n type contact regions of the device. Thin film wires are deposited and patterned such that the wires to the p-type regions run in one direction, and the wires to the n-type regions run in an orthogonal direction. One of the other wires should have a gap so as not to cross-circuit. This gap is bridged by spinning another planarization layer thereover and patterning it with vias to each side of the gap, and metal is patterned over the planarization layer to make the connection. Another passivation layer is spun on top, and the entire stack is etched so that the bridges and islands remain encapsulated with polymer but the intervening areas are completely etched away. This allows the bridges to be flexible. The PMMA sacrificial layer is undercut, or the PET layer is peeled off, and the entire sheet with circuits may be picked up again by PDMS stamp, and flipped over. The backside of the lower polyimide, or bottom of the circuits, is coated with Cr/SiO2; coating of the bridges is avoided by using a shadow mask evaporation procedure. The samples are subjected to a UV ozone treatment to impart dangling bonds to the SiO2, facilitating formation of covalent bonds with the next substrate to which the circuits are transferred. This final substrate may be thermally or mechanically pre-strained PDMS, such that after transfer, the strain is relaxed and the devices move closer together and the bridges pop up and buckle to accommodate the strain.

The stretchable LED array is transferred to the endoscopy device in a manner similar to that of the cylindrical optical sensor array. It is then encapsulated and integrated at the device level according to the methods described herein in connection with the micro-lens array. FIG. 53 shows an endoscopy device 1680E wherein circuitry 1000E comprises and array of photodetector and array of LED's (individually shown as 1030E. The LED array may utilize processing 1200E in the form of a logic device so that it only illuminates areas of interest during the operation and can be turned off when not in use as a power-saving mechanism. Device also includes a data transmission facility which includes RF antenna 1502E to wireless communicate with external devices.

In another embodiment of the present invention, the endoscopy device is equipped with an array of sensors which can be selected from those herein including those in connection with the discussion of 1100. Said sensors working in conjunction with circuitry 1000E to monitor pH, the presence of chemicals, and/or enzyme activity. In embodiments, the data collected by this sensor array is processed by local computing devices and transmitted via RF antenna or wired telemetry to an external receiver for further analysis.

At least some of the sensors in the array may comprise an ion-sensitive field effect transistor (ISLET), which generate data relating to changes in ion concentration. The output signals are typically a voltage and/or current difference, the magnitude of which varies with the change of sensed ion (e.g. hydronium) and/or enzyme. Other types of chemical sensors may be also or alternatively be utilized.

Another embodiment of the present invention relates to a capsule endoscopy device with a plurality of electronic components conformally fitted to the inside and/or outside walls of the capsule shell in order to conserve space. Conformal components are created by first performing stretchable processing on suitable materials as described herein. The basic components of such an endoscopy device include a passive or active matrix focal plane array, lens, illuminating LEDs, battery and telemetry devices (antenna and a radio transmitter). Optional components may include sensors described herein including ultrasound transducers, pressure sensors (e.g. silicon-based devices utilizing piezo-resistive or capacitive sensing mechanism, polymer-based sensors, and/or optically based sensors that measure physical deflections), temperature sensors (e.g. silicon band-gap temperature sensors, Pt resistance temperature devices), Ph/enzymatic/chemical sensors (e.g. Islets, as discussed above), targeted drug delivery components, electrocautery devices, biopsy devices, lasers, and heating devices. Components that benefit from contact with the GI wall and fluids (e.g. chemical sensors, LED, optical arrays) are situated in such a manner as to communicate fluidly or optically with the outer environment. This may be accomplished, for example, by placing the devices conformally on the outer surface of the capsule or through the use of electrodes which relay information from the outer region to the inside of the capsule. The remaining components (e.g. battery, telemetry devices) are preferably located on the inside of the capsule.

Methods for creating stretchable focal plane arrays and incorporating them into a desired substrate are described above. The same methods used to process and transfer focal plane arrays (stretchable processing) may be employed for various single-crystal silicon based electronic devices (e.g. antenna, RF transmitter, ISFET), with circuits being laid out (e.g. using CAD tools) in a manner that accommodates mechanical deformation and stretching.

In embodiments where it is desired to incorporate heterogeneous integrated circuits (non-silicon based devices), a slightly different approach may be employed. When creating a device that requires heterogeneous integration (e.g. LEDs), circuits are typically created on different substrates. After stretchable processing, the electronic devices are combined onto the same substrate using stamping methods previously described. This substrate may be the final destination of the devices (product integration) or may instead be intermediate (i.e. a rigid, flexible or stretchable material which will be incorporated into the product at a later time). At this point interconnects may be required to keep all of the heterogeneous components in electrical communication. These may be provided using soft lithography or another low-impact, low-temperature-processing (<400° C.) method with accurate alignment (<5 µm). The integrated circuit is then appropriately encapsulated and system/device interconnect integration can be executed as described above in connection with the micro-lens array.

As mentioned above, materials for the substrate used in the embodiments herein may be biocompatible. Such is the case with substrates including outer coatings of endoscopy device. In addition to biocompatibility, any part of the device housing that comes between the imager array and the object being monitored is preferably transparent. Further, the material in the outer shell of the endoscopy device facilitates easy travel through the GI tract. Examples of suitable biocompatible materials are given above.

It is to be understood that the housing of the device described above may also be the substrate and vice verse. Therefore, the skilled artisan will appreciate that certain discussions related to the substrate's material may—in certain embodiments—be understood as to apply to said housing.

It has been described herein in connection with embodiments of the invention that substrate can be fitted with circuitry comprising an array sensors and that said sensors could comprise pressure sensors. Circuitry can also comprise processing 1200 and 1200A, data collection 1300, amplifiers 1400, and data transmission 1500, among other capabilities. Therefore, another embodiment will be described that facilitates a quantitative examination of tissue based on palpation. In embodiments, the device is configured for self examination. The device is particularly suited for breast self-examinations; however, it will be appreciated that notwithstanding the following disclosure of an exemplary embodiment, the device and methods disclosed in connection with this exemplary embodiment apply to examinations of a variety of tissues and areas of the body, and such examination need not only be based on palpation.

Such an apparatus comprises a conformable and stretchable polymer fitted with an array of pressure transducers which remain operative notwithstanding stretching and bending of the body. The polymer substrate may cover a portion or the entire surface of the tissue and is used to measure the mechanical stiffness of the tissue at multiple discrete points. Pressure transducers coupled with processing facility can measure the mechanical stiffness of the tissue in response to known strains exerted on the surface of the tissue during palpation. As with other embodiment of the invention, the electronic devices of the circuitry may apparatus may comprise multiplexors, data acquisition and microprocessor circuits, which are connected via electronics wiring to the sensory circuitry covering the polymer substrate. Detection of abnormally hard regions of the tissue begins by first pressing the array of pressure transducers to the surface of the body part, for example, a breast. In embodiments, the device is fitted over the entire surface area of the body part (for example the breast) and as such a profile of the body-part stiffness can be mapped with high spatial resolution.

Embodiments of the present invention determine the presence and spatial extent of abnormally stiff legions of biological tissue, discriminate between relative stiffness of healthy and cancerous tissue, and facilitate immediate and localized therapeutic measures if appropriate. Because the mechanical properties of breast tissue are intrinsically heterogeneous, the present invention may be used regularly over time to precisely map the healthy state of the examined tissue thereby enabling the detection of structural abnormalities and/or deviations over time.

Embodiments of the present invention involve an instrumented polymer membrane fitted with flexible and stretchable electronic sensor and imaging arrays for measuring the material, mechanical, and/or optical properties of biological tissue. The invention utilizes flexible and stretchable circuitry suited for measuring parameters such as temperature, pressure and electrical conductivity of biological tissues. More specifically, the breast region is one area of interest for such tissue interrogation. The electronic components may be arranged in islands, which house required circuitry and are interconnected mechanically and electronically via interconnects. The interconnects, in turn, preferentially absorb strain and therefore enable the sensor arrays to withstand extreme stretching and conform to non-uniform shapes of biological tissues. The device islands and interconnects may be integrated into the device by transfer printing, as described below. Encapsulation of electronic devices and system/device interconnect integration can be performed at a number of stages in this process.

As decried amply herein, the arrays of devices, which may include one or more electronic devices and/or device components described herein (e.g. pressure, light and radiation sensors, biological and/or chemical sensors, amplifiers, A/D and D/A converters, optical collectors, electro-mechanical transducers, piezo-electric actuators), connected to a buffer and also to an amplifier are laid out in a device "island" arrangement. The device islands are ~50 µm×50 µm2 squares, most of which. Some islands accommodate active matrix switches and A/D converters, and some islands accommodate logic circuitry capable of reading in digital signals and processing them, and are capable of outputting data or storing data in memory cells. The circuits on these islands are configured and designed such that preferably only about one, but not more than about 100 electrical interconnections are required between any two device islands. Circuitry is made and applied according the methods described above, including in the manner described for a device island arrangement of devices.

Figure 54:
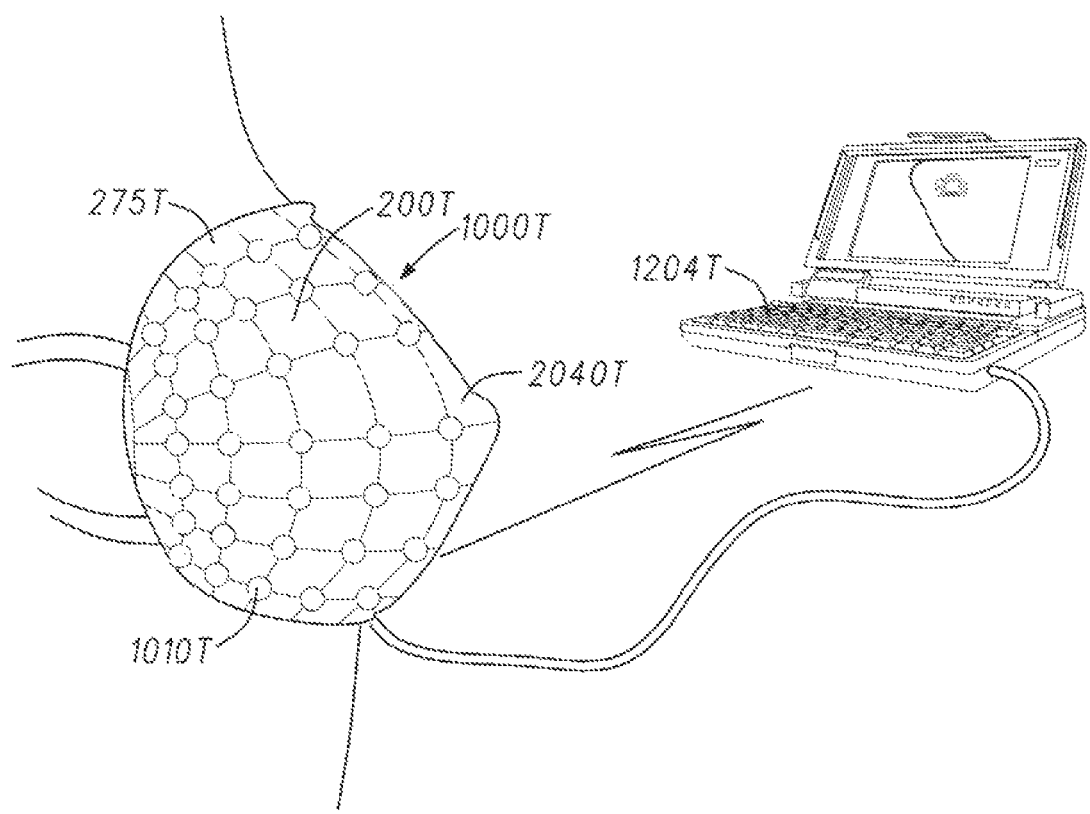
FIG. 54 depicts a tissue-screening device according to an embodiment of the invention.

FIG. 54 shows an embodiment of the invention adapted for the human breast. In embodiments of the invention, a conformable polymeric membrane 200T in the shape of a single human breast 2040T. Applied to the membrane 200T is circuitry 1000T comprising sensor and/or imaging arrays based on, for example, complementary metal-oxide semiconductor (CMOS) technology. In embodiments, the array(s) 1000T are physically integrated into the surface of the polymeric breast-shaped membrane 200T such as (poly)dimethylsiloxane (PDMS). This stamping procedure may be done by a transfer printing process defined herein. As described herein, arrays 1000T can be made of CMOS devices, which offer a variety of sophisticated sensing, imaging, and therapeutic functions, including (but not limited to) pressure sensing, light imaging, and trans-dermal drug delivery. The device arrays 1000T are designed to withstand stretching and bending by the use of effective circuit layout and interconnect designs as described herein.

In embodiments, the tissue screener may be created in the form of a bra 275T or integrated into a bra.

Embodiments may include circuitry/array 1000T that comprises arrayed pressure sensors. As such electronic devices 1010T can include pressure sensor. Each pressure sensor island comprises a flexible diaphragm membrane, which can record changes in capacitance in response to deflection. The pressure sensors can be made of a series of piezoresistive strain gauges, and/or conductive polymers. Each electronic device may contain an amplifier and A/D transistors to provide local signal processing on each island. The sensor islands are encapsulated with a thin layer of polymer (~100 µm thick) to protect the interconnects and the circuitry. The surface containing the thin layer is positioned in direct contact with the breast tissue during the procedure. The surface opposite the sensors can be fitted with an additional polymer layer (300-500 µm thick) that forms as an enclosure with an air-filled gap. Inflating this air-filled space by a known amount (with a peristaltic pump) facilitates the application of known strains to the breast tissue. Therefore, breast tissue can be depressed by a fixed amount over its entire surface by inflating the air-filled space, and the pressure at each location is recorded with pressure sensors.

In another embodiment, each device 1010T includes on-off switch transistors that are coupled to said pressure sensors and activated once pressure is applied. Using this on-off mechanism, the device can determine which sensors have been pressed during sensing and communicate such to the user, via for example, a graphical user interface on an external device, or visual means such as lighted areas were sensors have been either activated or not activated, or tactile indicators of actuation. One key advantage of using a sensor array with on-off feedback is that it alerts the user if any part of the sensor array has not been depressed in the case of manual force exertion onto the breast. Therefore, it eliminates the possibility of overlooking regions of the breast during a manual examination. Thus in embodiments, each electronic device can provide feedback if the pressure sensing mechanism was not properly activated during breast examination.

In another embodiment of the invention, the devices are anchored to the breasts with straps similar to those of a 275T. Thus in use, the user can wear the apparatus like a bra. In embodiments, the device has a port (not shown) for connecting to an external processing facility 1200A, which in FIG. 54 is depicted as residing in a laptop computer 1204T. Wireless communication is also possible and depicted in the figure. The external device can provide power and also receives data during screening. In embodiments, processing facility 1204T, is in electronic communication with the circuitry and is configured to detect that the bra is worn and prompts the user to start the breast exam. The outer surface of the device on the side opposite to the breast can be covered with a thin encapsulating layer of polymer as described in previous embodiments. The space between this outer surface and the surface of the apparatus can be air-sealed and filled with air using a peristaltic air pump. Filling this space with air enables uniform pressure to be applied along the entire surface of the breast, which in turn provides control over how much strain is applied to the breast.

In another embodiment of the invention, the stretchable material 200T comprises circuitry 1000T having an array of ultrasound transducers (e.g. piezoelectric crystals). Each device 1010T comprises a receiver that senses acoustic reflections generated by a source emitter that sends acoustic waves through the tissue at megahertz frequencies. This embodiment can be combined with other sensors mentioned herein, including, pressure sensors to further locate and image abnormal regions of breast tissue. As with all embodiments herein, the sensors can be in electronic communication with the other facilities, electronic devices, components, and elements of the circuitry or external devices including processing facilities that receive the data from said sensors and process it according to the methods described herein, and further cause output devices to generate the output as described herein.

Circuitry 1000T could also comprise an array of infrared emitters and detectors (e.g. bolometer). The infrared wavelength is chosen to minimize the ratio of healthy tissue absorption to cancerous tissue absorption. The emitters illuminate the breast and the detectors image the radiation. This embodiment can be combined and integrated with any of the aforementioned sensing concepts for increased accuracy.

Circuitry 1000T could also comprise an array of stimulating and recording electrodes to produce a spatial map of electrical impedance of the tissue. The electrical conductivity and dielectric properties of cancerous tissue may differ from those of healthy tissue. To detect changes in electrical impedance induced by the presence of local cancer tissue, a known AC current can be injected at a known location, and voltage is recorded at a number of points defined by the array of recording electrodes. In this embodiment, the encapsulating layer of polymer covers everything except the contact regions of the electrodes. A photo-patternable polymer can be used to achieve this step.

Electrical impedance scanning provides data to enable a 3-D spatial map of complex impedance and permittivity over a range of frequencies, which can be used as a sensing tool to predict the presence of abnormal cancerous cells deep within breast tissue. This embodiment can be combined and integrated with any of the aforementioned methods and concepts for increased accuracy.

The data collected by the array of sensors can be stored for retrieval and/or transmitted to an external system for time-based tracking of tissue health.

In embodiments, the sensor data from the array 1000T of pressure transducers can amplified and converted to digital form at the level of each sensor and then transmitted to a multiplexor. Alternatively, the analog circuitry can be included at the level of each device 1010T and the digital processing circuits can be housed off of the polymer. Once the data is collected from each point and transmitted to a computer terminal, the user may prompted that the examination is complete. The user may examine the data herself and/or send it to her doctor for further review (as an example).

Thus, in embodiments it will be apparent that the circuitry of the device is in electronic communication with a processing facility configured to accept data from the device and cause output facility (previously discussed in connection with FIG. 1A as 300) to generate a graphical or otherwise visual presentation of data related to the examination. For example, tissue maps as described herein may be created from all sensor data disclosed herein and presented on output facility (as shown on 1204T). Textual and graphical data relating to the data generated by the circuitry may be presented to the user. The processing facility may be configured to cause historical data generated by the circuitry to be stored, aggregated, and presented in a variety of ways including daily, weekly, monthly, or any other useful interval readings, charts, reports, and the like.

Returning to the physical characteristics of the device itself, the device may be opaque such that the woman's breasts are not visible. This feature can be achieved by adding opaque (e.g., black) dye to the elastomer prior to curing. In this embodiment, the array of sensors remains in close contact with the breast without having to expose her bare breasts. Because of the biocompatibility of polymers like PDMS, this type of device can be fitted within a normal bra for convenience.

In one embodiment of the invention the electronics are integrated into an elastomeric material which contours a breast. This shape is reproducible in different sizes depending on the breast size of the intended user. The process of creating the breast shaped device begins with the creation of a first breast shaped mold. A second negatively shaped mold is then made to match the curvature of the first. An elastomeric material such as PDMS is poured between the two moulds to create a thin film (less than 2 mm). This layer is cured to create a solid breast shaped film of elastomeric material upon which the electronics will be stamped by the transfer printing process described above. In order to accomplish this printing step, the elastomeric material is stretched into a flat plane and placed in contact with the already "stretch processed" electronics. The electronics preferentially adhere to the surface of the elastomer either by Van der Waal forces or by chemical aided means. Subsequently, the elastomer with embedded electronics is relaxed and buckling occurs within the interconnects of the electronics array, enabling stretchability.

Further encapsulation and device integration may be required. This may be done by connecting (manually or by electronic automation) anisotropic conductive films (ACF) to bond pads which are designed to be in an easily accessible area on the stretchable electronic array (for example on its outer perimeter). This ACF connects the electronics embedded elastomer to a device which is responsible for supplying power, relaying information of other tasks that require electrical contact.

In accordance with one or more embodiments, the stretchable electronics are integrated directly onto a bra-like substrate. This may be achieved by coating a bra-like article with an elastomeric substrate (e.g. PDMS) and adhering the above described stretchable electronic array to the newly coated bra-like article.

In a similar vein to the embodiments described above in connection with FIG. 54, the substrate of the invention may comprise a conformal sheet or tape to wrap conformally fit on the body and thus to prove information regarding the body part of interest or underlying tissue of interest. It should be noted that sensor tape may be used in nonmedical applications such as the monitoring may have applications in a wide variety of fields including structural monitoring of vehicles and civil structures. Such embodiments may be referred to herein as "sensor tape"; however it should be recognized that tape can include any of the flat, conformal substrates described herein. Sensor tape may be equipped with any of the herein-described functionality of the circuitry including any type of sensor or manner of sensor configuration, which may be used for medical and nonmedical applications.

For integration of these sensor tapes into complex shapes, a degree of stretchability is required. In addition, certain high performance applications (vital sign monitoring) need to employ materials capable of reliable performance. The combination of strain tolerance and performance are non-trivial challenges that have not completely been resolved by the prior art.

In addition to comprising sensors, the devices may communicate with remote units such as a power source, telemetry unit, processor facility, or actuators. One embodiment of the invention refers to an sensor tape used for the purpose of measuring human vital signs. Wounds and trauma inflicted on the battlefield, in a car accident, or even in a fire emergency require rapid and accurate assessment of a person's health prior to evacuation and transport to hospital care. Monitors capable of measuring electrocardiographs (ECGs) represent one of the most powerful technologies for this purpose. Devices that exploit polymer or organic electronic materials have some potential for low cost, bendable devices. Their poor electrical performance, however, prohibits the use of modern signal amplification methods or radio frequency functionality. In addition, an unproven ability to achieve basic circuits and the uncertain reliability of existing organic electronics technologies lead to significant risk. Amorphous or laser annealed polycrystalline silicon provide alternatives, but the moderate levels of device uniformity and limited ability to achieve integrated circuits with realistic levels of functionality pose significant challenges.

Thus, such embodiments may include sensor arrays that can provide a data on surface topology, temperature, pressure, electrical conductivity, pH, chemical, and/or enzymatic activity—among others herein described. In embodiments of the invention, the sensor tape can be fitted with dense array of photodetectors (as disclosed herein) used to image either a flat or curved surface. The direct contact between the surface being imaged and photodetectors can preclude the need for lens arrays for focusing purposes. However, if required, microlens arrays may be included in the circuit design. Additional light sources may be required. Imagining facility 1600 described herein may be used.

In embodiments of the invention, the stretchable tape-like substrate is covered with an array of ultrasound transducers (e.g. piezoelectric crystals). Each device island comprises a receiver that senses acoustic reflections generated by a source emitter that sends acoustic waves through the tissue at megahertz frequencies. Such embodiments embodiment can be combined with pressure sensors to further locate or image abnormal regions of tissue (or structures and vehicles in nonmedical embodiments). The detection of structure shift or movement is also contemplated in nonmedical embodiments of the sensor tape.

In embodiments, the sensor tape is a wearable vital sign monitor. In addition to or alternatively to the stretch circuitry described herein, ultrathin ASICs (~5 µm) may be integrated into thin deformable substrates (polymeric, paper based ~50 µm) in neutral mechanical plane layouts. Densely packed arrays of ASICs on an SOI wafer (0.6 µm process) are formed. Lithographic processing and vertical trench etching, followed by removal of the buried oxide will yield isolated chiplets (~0.5×0.5 mm2, and ~5 µm thick) that remain tethered to the SOI wafer through 'anchor' structures strategically located around the periphery. This process will yield ASICs referred to as 'printable' due to their ability to be removed and placed onto a target substrate with a soft, elastomeric stamp. Methods for transfer printing described above may be used with these flexible ASICs. The attractive features of this approach include efficient utilization of the CMOS SOI wafer for reduced cost, ultrathin circuit layouts for mechanical flexibility and compatibility with metallization formed by conventional, planar processing for interconnect. It should be noted that the above processing techniques may be used with any embodiment described herein wherein a conformal sensing/therapeutic device is desired.

The wearable sensor tape includes such an IC, together with magnetically coupled receiver and transmitter circuits. As such, it offers medical-grade performance. The measured properties satisfy the diagnostic requirements outlined in the ANSI/AAMI EC-13 standard and safety parameters described in EC 60601-1. The circuitry additionally meets requirements for defibrillation and leakage tests; these anti-crosstalk features ensure patient safety during mission-critical applications, such as resuscitation procedures. The entire circuit draws ~300 µA at 3V, suggesting that it has the capacity to function nearly 3 days on 14 mA/hr Li thin-film batteries, such as those manufactured by Solicore Inc.

The ASIC connects to RF inductive coil components and passive filters (resistors, capacitors) on the plastic tape substrate to optimize the signal to noise ratio. This strategy of moving the passive components 'off-chip' reduces the size and cost of the ASIC.

Figure 55:
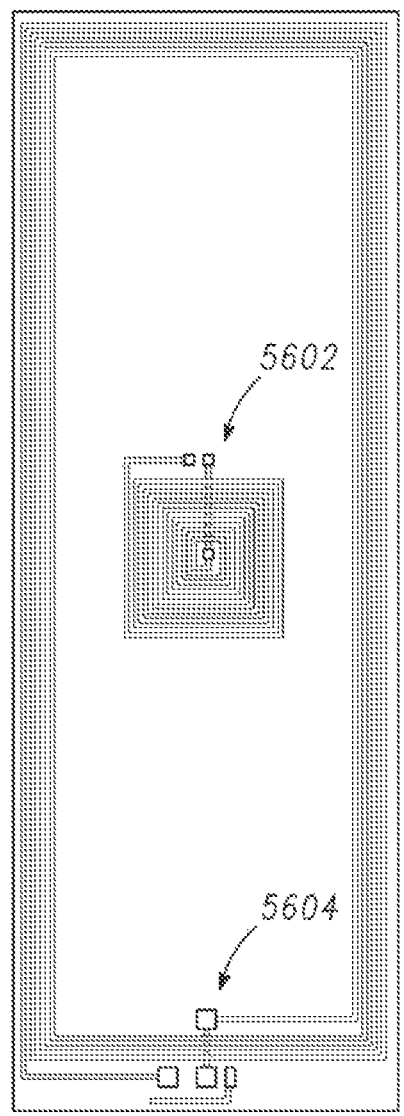
FIG. 55 is a schematic drawings of wireless RF modules that may form a part of an embodiment of the invention.

FIG. 55 is a schematic drawing of the wireless RF modules which shows the receiver and transmitter circuits (5602 and 5604 respectively). These components collectively make up the sensor tape embodiment, which can receive and transmit signals in a wireless mode.

Figure 56:
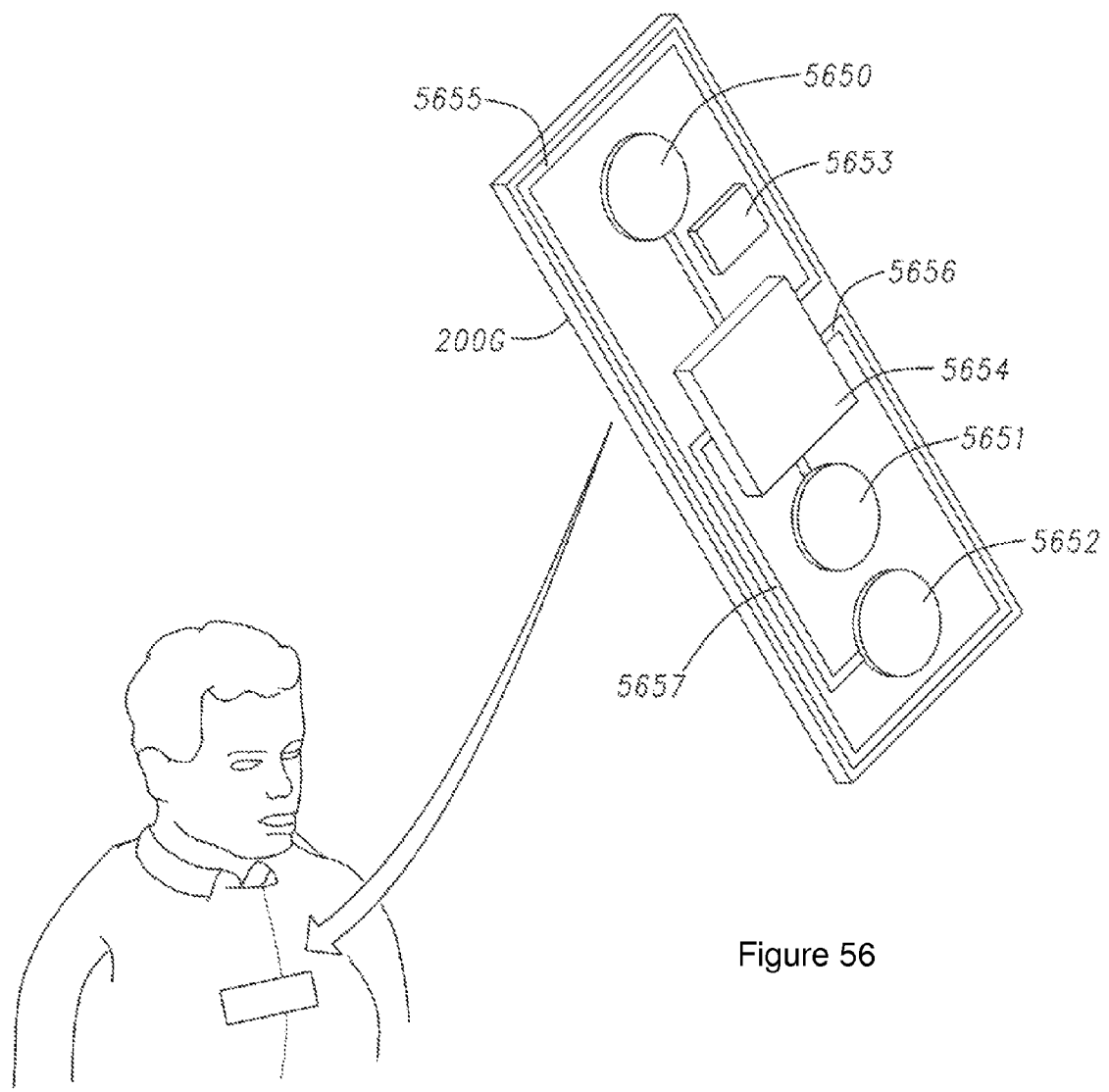
FIG. 56 depicts another embodiment of the invention configured for use as an ECG monitor.

In embodiments, the sensor tape includes an inductive coupling transceiver; a simple radio frequency circuit consisting of inductor-based receiver and transmitter coils. The design features a pair of inductor coils and passive components, for minimal cost. The active components—microprocessor, display driver, and memory—all reside in the remote unit. Inductive coupling is appealing as a mode of transmission for embodiments such as EGC monitors because soldiers often carry multiple layers of armor and clothing, which can reduce signal transmission to and from a device located on the bare chest. Short distance inductive coupling has the capacity and signal strength to transmit through metal layers and thereby overcomes signal transmission limitations where other forms of radio signals may fail. High-frequency AC current (<50 MHz) in the form of an RF signal is fed into a resonant network consisting of an inductive coil and a capacitor to induce a sizeable magnetic field. This field in turn couples energy into a transmitting coil. The receiver coil contains a 56 AWG spiral conductor with 19.5 turns (square diameter: 2.5 cm) and an inductance of 20 pH. The transmitter coil has an inductance of 220 μH with 16 turns and rectangular layout (9×3 cm2). The large size of the transmitter coil places important size constraints on the tape. This particular antenna design spans along the outer perimeter of the sensor tape (which is shown in FIG. 56) thereby providing sufficient size and number of turns.

A smaller coil located in the remote unit featuring a capacitor wired in parallel forms a resonant receiver circuit. Adequate power levels can be transmitted when the smaller receiver coil is within 5-10 feet of the sensor tape's transmitter. After rectification and filtering within the remote monitor, the receiver RF signal can be turned back into a DC voltage, which can then be digitized with 16-bit resolution and analyzed accordingly with a conventional microprocessor (e.g., the Atmel ARM9). Laboratory experiments with a prototype circuit indicate that 94% of power at 6 volts, 22 mA can be transferred over a relatively short distance of about 1 cm. Simulations indicate that this efficiency can be maintained over a distance of 5-10 feet by actively powering the circuit with an on-board battery, such as the Li battery described above.

Assembly of ultrathin ASIC is accomplished with a transfer printing technique discussed above and in the appendices cited in U.S. Provisional Application Ser. No. 61/164,920 entitled "Stretchable and Flexible Thin Film Electronic Devices" filed Mar. 31, 2009, the entirety of which is hereby incorporated herein by reference.

This process involves parallel, high speed transfer of ultrathin ASICs from an SOI wafer to a plastic sheet for the sensor tape. In each transfer step, thousands of individual ASIC chips are moved from an SOI wafer to sparse arrays on a plastic sheet (FIG. 2). Cutting this sheet to form and integrating with other elements will complete the tapes. Adhesion to the stamps in the transfer process is provided by van der Waals forces. Thin adhesive layers (e.g., polyimide) on the receiving substrates facilitate transfer. The critical features of this approach are that it makes efficient usage of the CMOS, for reduced cost; it is compatible for ultrathin chiplets; it can be used with low cost, flexible sheets of plastic substrates.

FIG. 56 provides a schematic illustration of an sensor tape configured to be an ECG monitor and which will be referred to as "ECG Tape", consisting of an ultrathin ASIC together with passive components and inductive coupling circuitry printed on a plastic substrate, which in embodiments in Kapton®. In embodiments, an encapsulation layer of polyimide helps achieve a neutral mechanical plane design that will minimize bending induced changes in the operation of the ASIC. In embodiments, the tape may be ~300-500 μm thick, dominated in thickness by the flexible Li battery, plastic substrate, and top encapsulation layers. In FIG. 56, 5656 is a transmitter antenna and 5657 are the interconnects between components. In an exemplary embodiment, the overall dimensions are determined to allow a spacing (~8 cm) between the Ag/AgCl sensor electrodes (5650 is the positive, 5651 is the negative, 5652 is ground) sufficient to capture strong electrical signals passing through the heart conduction pathway from the atria to the ventricles. To conserve surface area around the electrodes, the large transmitter antenna 5655 (in embodiments, ~3×9 cm2 rectangle layout) is positioned around the perimeter of the tape. The tape may also carry an ultra-thin Li battery 5653 having a minimum battery-powered life of approximately 24 hours with potential of up to 3 days. The key off-chip components of the sensor tape are described in greater detail below. Li Battery: Thin-film 3V Li ion batteries (made by Solicore Inc.) have dimensions (0.38 mm×26 mm×29 mm) and power outputs that are suitable for the ECG tape systems proposed here. These batteries are flexible and therefore, can be co-located on the tape substrate. Printed metal lines provide the electrical connections from the inductive coupling circuitry, and the ASIC to the battery anode (metallic lithium) and cathode (MnO2) contacts.

Passives: The passive filters built around the TL062 Op-Amps in the ECG circuit must have low RC time constants with large capacitances (values significantly larger than picofarads). To minimize the size of the ASIC, thereby increasing the mechanical flexibility and reducing the cost of the ECG tape, the passive filters are formed on the tape substrate. Such components may be formed either using thin film processing directly, or inexpensive off-the-shelf components (0402 size made by Venkel Ltd.) can be attached with conventional surface-mount technology. Resistors with 10Ω-1 MΩ resistances (typ. dimensions 1 mm×0.5 mm×0.35 mm) and capacitors with 0.1 pF-100 μF capacitances (typ. dimensions 1 mm×0.5 mm×0.3-0.5 mm) are compatible with the form-factor of the tape. Alternatively, thin film passive filters based on copper and benzocyclobutene (BCB) may be used.

Metal interconnects, RF antenna, and electrodes: The off-chip metal interconnects, antenna, and electrodes may be deposited on the flexible substrate. The metal conductive layers (as shown in FIG. 57) comprise of three-layers of patterned metal (chromium:gold:chromium; 3:150:3 nm) deposited on thin layers of polyimide (1-1.5 μm thick). These metal layers may be deposited on the plastic substrate using conventional metal evaporation techniques. The RF antenna coils may comprise copper metal evaporated on the plastic substrate with trace thickness and width of 18 μm and 200 μm, respectively. Similarly, three Ag/AgCl thin-film electrode disks (~10 μm thickness; ~1.5 cm diameter) can also be deposited on the plastic substrate. An adhesion layer of chromium (~500 nm) promotes attachment of the thin-film electrodes to the underlying substrate. To ensure low impedances (<10 kΩ) at the electrode-skin interfaces and to minimize junction potentials, the electrode disks will each be coated with a thin layer (~0.5 mm) of non-irritating 3M NaCl gel after processing and packaging. This thin salt gel layer minimizes the junction potentials at the electrodes and thereby improves electrical signal-to-noise.

Certain of the methods and systems described in connection with the invention described (hereinafter referred to as the "Subject Methods and Systems") may be deployed in part or in whole through a machine that executes computer software, program codes, and/or instructions on a processor integrated with or separate from the electronic circuitry described herein. Said certain methods and systems will be apparent to those skilled in the art, and nothing below is meant to limit that which has already been disclosed but rather to supplement it.

The active stretchable or flexible circuitry described herein may be considered the machine necessary to deploy the Subject Methods and System in full or in part, or a separately located machine may deploy the Subject Methods and Systems in whole or in part. Thus, "machine" as referred to herein may be applied to the circuitry described above, a separate processor, separate interface electronics or combinations thereof.

The Subject Methods and Systems invention may be implemented as a method on the machine, as a system or apparatus as part of or in relation to the machine, or as a computer program product embodied in a computer readable medium executing on one or more of the machines. In embodiments, the processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like. Nothing in this paragraph or the paragraphs below is meant to limit or contradict the description of the processing facility described herein and throughout.

A processor may include one or more cores that may enhance speed and performance of a multiprocessor. In embodiments, the process may be a dual core processor, quad core processors, other chip-level multiprocessor and the like that combine two or more independent cores (called a die).

The Subject Methods and Systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

If the Subject Methods and Systems are embodied in a software program, the software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The Subject Methods and Systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions pertaining to the Subject Methods and Systems described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, program codes, and instructions pertaining to the Subject Methods and Systems described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions pertaining to the Subject Methods and Systems may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The Subject Methods and Systems described herein may transform physical and/or or intangible items from one state to another. The methods and systems described herein may also transform data representing physical and/or intangible items from one state to another.

The elements described and depicted herein and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The Subject Methods and Systems, and steps associated therewith, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above in connection with the Subject Systems and Methods and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been described in connection with certain preferred embodiments, other embodiments would be understood by one of ordinary skill in the art and are encompassed herein.

All documents referenced herein are hereby incorporated by reference.

What is claimed is:

1. A method to determine parameters of a tissue comprising the steps of:
    placing a device in at least partial contact with said tissue, the device comprising circuitry of a stretchable array of sensors;
    determining a subset of sensors in said array of sensors that are in conformal contact with said tissue; and
    activating one or more sensors in said subset of sensors that are in conformal contact with said tissue by applying one or more multiplexing techniques to enable selected portions of the circuitry corresponding to the one or more sensors.

2. The method as recited in claim 1, wherein the activating of the one or more sensors includes dynamically selecting the one or more sensors in said subset that are to be activated.

3. The method as recited in claim 2, wherein the activating of the one or more sensors includes at least one of selecting and changing a spatial pattern of sensors in said subset of sensors that are to be activated by dynamically selecting the one or more sensors in said subset that are activated.

4. The method as recited in claim 1, wherein the determining of the subset of sensors in said array of sensors that are in conformal contact with said tissue includes determining at least one sensor that is not in direct physical contact with said tissue.

5. The method as recited in claim 4, wherein the determining of the subset of sensors in said array of sensors that are in conformal contact with said tissue includes determining at least one sensor in said subset of sensors that is in electrical contact with said tissue.

6. The method as recited in claim 4, wherein the determining of the subset of sensors in said array of sensors that are in conformal contact with said tissue includes determining at least one sensor in said subset of sensors that is oriented relative to said tissue such that consistent detection of parameters of said tissue can be obtained.

7. The method as recited in claim 1, wherein the activating of the one or more sensors includes detecting data indicative of a parameter of said tissue from the one or more sensors in said subset of sensors that are in conformal contact with said tissue.

8. The method as recited in claim 7, wherein said data is indicative of thermal properties of said tissue.

9. The method as recited in claim 7, wherein said data is indicative of electrical conductance of said tissue.

10. The method as recited in claim 7, further comprising generating a map that indicates measurements of the parameter of said tissue at locations in said tissue.

11. The method as recited in 10, wherein said data is indicative of electrical conductance of said tissue and said map comprises a map of electrical activity of said tissue.

12. The method as recited in claim 7, wherein said tissue is an inner surface of a lumen, and further comprising determining an occlusion of the lumen by the device using the data indicative of a parameter of said tissue detected from the one or more sensors in said subset of sensors that are in conformal contact with said tissue.

13. The method as recited in claim 12, wherein determining the occlusion of the lumen includes determining a force applied to the inner surface of the lumen by the device using the data indicative of a parameter of said tissue.

14. A method to determine parameters of a tissue comprising the steps of:
    placing a device in at least partial contact with said tissue, the device comprising circuitry of a stretchable array of contact sensors and an array of sensors to detect data indicative of a parameter of said tissue;
    using said contact sensors to determine a portion of said device that is in conformal contact with said tissue; and
    activating one or more sensors in said array of sensors of the circuitry, according to one or more multiplexing techniques, to detect data indicative of a parameter of said tissue, wherein said one or more sensors are determined to be in said portion of said device that is in conformal contact with said tissue.

15. The method as recited in claim 14, wherein the determining of said portion of said device that is in conformal contact with said tissue includes determining at least one sensor in said array of sensors that is oriented relative to said tissue such that consistent detection of parameters of said tissue can be obtained.

16. The method as recited in claim 14, wherein the activating of the one or more sensors includes dynamically selecting the one or more sensors in said array of sensors that are to be activated so as to at least one of select and change a spatial pattern of sensors in said array of sensors that are to be activated.

17. The method as recited in claim 14, wherein the determining of said portion of said device that is in conformal contact with said tissue includes determining at least one sensor in said array of sensors that is not in direct physical contact with said tissue.

18. The method as recited in claim 17, further comprising determining at least one sensor in said array of sensors that is in electrical contact with said tissue.

19. The method as recited in claim 14, wherein said data is indicative of at least one of thermal properties of said tissue and electrical properties of said tissue.

20. The method as recited in claim 19, wherein said data is indicative of electrical conductance of said tissue, and further comprising generating a map that indicates electrical activity at locations in said tissue.

* * * * *